United States Patent
Penders et al.

(10) Patent No.: US 11,576,622 B2
(45) Date of Patent: Feb. 14, 2023

(54) SYSTEMS AND METHODS FOR MONITORING UTERINE ACTIVITY AND ASSESSING PRE-TERM BIRTH RISK

(71) Applicant: Bloom Technologies NV, Genk (BE)

(72) Inventors: Julien Penders, San Francisco, CA (US); Michiel Rooijakkers, Eindhoven (NL); Eric Dy, San Francisco, CA (US); Marco Altini, San Francisco, CA (US)

(73) Assignee: BLOOM TECHNOLOGIES NV, Genk (BE)

(*) Notice: Subject to any disclaimer, the term of this patent is extended or adjusted under 35 U.S.C. 154(b) by 125 days.

(21) Appl. No.: 16/632,341

(22) PCT Filed: Jul. 19, 2018

(86) PCT No.: PCT/IB2018/055394
§ 371 (c)(1),
(2) Date: Jan. 18, 2020

(87) PCT Pub. No.: WO2019/016759
PCT Pub. Date: Jan. 24, 2019

(65) Prior Publication Data
US 2020/0196958 A1     Jun. 25, 2020

Related U.S. Application Data

(60) Provisional application No. 62/548,094, filed on Aug. 21, 2017, provisional application No. 62/534,586, filed on Jul. 19, 2017.

(51) Int. Cl.
*A61B 5/00* (2006.01)
*G16H 40/67* (2018.01)
(Continued)

(52) U.S. Cl.
CPC .......... *A61B 5/7275* (2013.01); *A61B 5/0002* (2013.01); *A61B 5/0205* (2013.01);
(Continued)

(58) Field of Classification Search
CPC ... A61B 5/7275; A61B 5/0002; A61B 5/0205; A61B 5/4836; A61B 5/486;
(Continued)

(56) References Cited

U.S. PATENT DOCUMENTS

| 5,042,503 A | 8/1991 | Torok et al. |
| 5,623,939 A | 4/1997 | Garfield et al. |

(Continued)

FOREIGN PATENT DOCUMENTS

| CA | 2608497 A1 | 8/2006 |
| CA | 2754721 A1 | 9/2010 |

(Continued)

OTHER PUBLICATIONS

Bakris, "A practical approach to achieving recommended blood pressure goals in diabetic-patients", Archives of Internal Medicine, vol. 161, Issue 22, 2001, pp. 2661-2667.
(Continued)

*Primary Examiner* — Carl H Layno
*Assistant Examiner* — Aya Ziad Bakkar
(74) *Attorney, Agent, or Firm* — Aurora Consulting LLC; Kristen J. Hansen; Ashley Sloat

(57) ABSTRACT

A method for uterine activity monitoring may include: acquiring a plurality of signals from a plurality of sensors during uterine activity; processing the plurality of signals to extract a plurality of uterine electrical activity characteristics; analyzing the plurality of uterine electrical activity characteristics; and classifying the uterine activity as one of: a preterm labor contraction, a labor contraction, a Braxton-Hicks contraction, and a state of no contraction. A method of
(Continued)

assessing over time a pre-term birth risk of a pregnant female may include: calculating a baseline pre-term birth risk score based on a user input; acquiring, over time, a signal from a sensor; analyzing the signal to extract a parameter of interest, such that the parameter of interest comprises a physiological parameter; and calculating an instant pre-term birth risk score based, at least in part, on the parameter of interest and the user input.

21 Claims, 44 Drawing Sheets

(51) Int. Cl.
| | |
|---|---|
| G16H 50/30 | (2018.01) |
| A61B 5/0205 | (2006.01) |
| A61B 5/021 | (2006.01) |
| A61B 5/024 | (2006.01) |
| A61B 5/08 | (2006.01) |
| A61B 5/107 | (2006.01) |
| A61B 5/11 | (2006.01) |
| A61B 5/145 | (2006.01) |
| A61B 5/01 | (2006.01) |
| A61B 5/0533 | (2021.01) |
| A61B 5/16 | (2006.01) |
| A61B 8/08 | (2006.01) |

(52) U.S. Cl.
CPC ............ *A61B 5/486* (2013.01); *A61B 5/4836* (2013.01); *A61B 5/7203* (2013.01); *A61B 5/7267* (2013.01); *A61B 5/7425* (2013.01); *G16H 40/67* (2018.01); *G16H 50/30* (2018.01); *A61B 5/01* (2013.01); *A61B 5/021* (2013.01); *A61B 5/02405* (2013.01); *A61B 5/02411* (2013.01); *A61B 5/0533* (2013.01); *A61B 5/0816* (2013.01); *A61B 5/1072* (2013.01); *A61B 5/1118* (2013.01); *A61B 5/14532* (2013.01); *A61B 5/14542* (2013.01); *A61B 5/165* (2013.01); *A61B 5/4356* (2013.01); *A61B 5/4362* (2013.01); *A61B 5/4815* (2013.01); *A61B 5/4845* (2013.01); *A61B 5/4848* (2013.01); *A61B 5/4866* (2013.01); *A61B 5/6804* (2013.01); *A61B 5/6823* (2013.01); *A61B 5/6831* (2013.01); *A61B 5/6833* (2013.01); *A61B 8/0866* (2013.01)

(58) Field of Classification Search
CPC ....... A61B 5/7267; A61B 5/7425; A61B 5/01; A61B 5/021; A61B 5/02405; A61B 5/02411; A61B 5/0816; A61B 5/1118; A61B 5/14532; A61B 5/14542; A61B 5/165; A61B 5/4356; A61B 5/4362; A61B 5/4848; A61B 5/6823; A61B 5/6831; A61B 8/0866; G16H 50/30
See application file for complete search history.

(56) References Cited

U.S. PATENT DOCUMENTS

| | | | |
|---|---|---|---|
| 5,776,073 A | 7/1998 | Garfield et al. | |
| 5,954,663 A | 9/1999 | Gat | |
| 6,134,466 A | 10/2000 | Rosenberg | |
| 6,171,263 B1 | 1/2001 | Sullivan | |
| 6,556,977 B1* | 4/2003 | Lapointe | G16H 50/20 706/45 |
| 6,816,744 B2 | 11/2004 | Garfield et al. | |
| 7,285,090 B2 | 10/2007 | Andre | |
| 7,532,923 B1 | 5/2009 | Hayes-Gill et al. | |
| 8,116,855 B2 | 2/2012 | James et al. | |
| 8,229,550 B2 | 7/2012 | James et al. | |
| 8,255,238 B2 | 8/2012 | Powell et al. | |
| 8,398,546 B2 | 3/2013 | Andre | |
| 8,734,296 B1 | 5/2014 | Brumback | |
| D717,674 S | 11/2014 | Vu et al. | |
| 8,880,140 B2 | 11/2014 | Hayes-Gill et al. | |
| D739,284 S | 9/2015 | Vu et al. | |
| D739,775 S | 9/2015 | Vu et al. | |
| D739,776 S | 9/2015 | Vu et al. | |
| D739,777 S | 9/2015 | Vu et al. | |
| D739,778 S | 9/2015 | Vu et al. | |
| D740,706 S | 10/2015 | Vu et al. | |
| D743,819 S | 11/2015 | Golnik et al. | |
| D752,764 S | 3/2016 | Peters | |
| 9,307,923 B2 | 4/2016 | Peters et al. | |
| 9,314,203 B2 | 4/2016 | Peters | |
| 9,392,952 B1 | 7/2016 | Oz et al. | |
| 9,572,504 B2 | 2/2017 | Oz et al. | |
| D781,568 S | 3/2017 | Workman | |
| 9,642,544 B2 | 5/2017 | Oz et al. | |
| 9,713,430 B2 | 7/2017 | Oz et al. | |
| 9,717,412 B2 | 8/2017 | Roham et al. | |
| 9,763,583 B2 | 9/2017 | Oz et al. | |
| 9,999,367 B2 | 6/2018 | Vullings et al. | |
| 10,064,566 B2 | 9/2018 | Atallah et al. | |
| 11,324,437 B2 | 5/2022 | Mhajna | |
| 2001/0039503 A1 | 11/2001 | Chan | |
| 2003/0004403 A1 | 1/2003 | Drinan et al. | |
| 2004/0087840 A1 | 5/2004 | Main | |
| 2005/0267376 A1 | 12/2005 | Marossero et al. | |
| 2007/0191728 A1 | 8/2007 | Shennib | |
| 2007/0255184 A1 | 11/2007 | Shennib | |
| 2007/0260133 A1 | 11/2007 | Meyer | |
| 2008/0029333 A1 | 2/2008 | Oz | |
| 2008/0089184 A1 | 4/2008 | Palmer | |
| 2008/0275309 A1 | 11/2008 | Andre | |
| 2008/0275316 A1 | 11/2008 | Fink et al. | |
| 2009/0036787 A1 | 2/2009 | James et al. | |
| 2009/0143650 A1 | 6/2009 | Guion-Johnson et al. | |
| 2009/0177068 A1 | 7/2009 | Andre | |
| 2009/0192396 A1 | 7/2009 | Hayes-Gill et al. | |
| 2009/0259133 A1 | 10/2009 | Wolfberg | |
| 2009/0299212 A1 | 12/2009 | Principe et al. | |
| 2010/0211594 A1 | 8/2010 | Penders et al. | |
| 2010/0235782 A1 | 9/2010 | Powell et al. | |
| 2010/0274145 A1 | 10/2010 | Tupin, Jr. et al. | |
| 2011/0137913 A1 | 6/2011 | Bhatti | |
| 2011/0172504 A1 | 7/2011 | Wegerich | |
| 2011/0190652 A1 | 8/2011 | Fink et al. | |
| 2011/0237972 A1* | 9/2011 | Garfield | A61B 5/4356 600/546 |
| 2011/0251512 A1 | 10/2011 | Fink et al. | |
| 2011/0251817 A1 | 10/2011 | Burns et al. | |
| 2011/0270118 A1 | 11/2011 | Garfield et al. | |
| 2011/0306893 A1 | 12/2011 | Harrold et al. | |
| 2012/0075103 A1 | 3/2012 | Powell et al. | |
| 2012/0150010 A1 | 6/2012 | Hayes-Gill et al. | |
| 2012/0232398 A1 | 9/2012 | Roham et al. | |
| 2012/0245439 A1 | 9/2012 | Andre | |
| 2012/0265090 A1 | 10/2012 | Fink et al. | |
| 2012/0289789 A1 | 11/2012 | Jain et al. | |
| 2013/0006132 A1 | 1/2013 | Brody et al. | |
| 2013/0030831 A1 | 1/2013 | Powell et al. | |
| 2013/0090538 A1 | 4/2013 | Garfield et al. | |
| 2013/0102857 A1 | 4/2013 | Wolfberg | |
| 2013/0158367 A1 | 6/2013 | Andre | |
| 2013/0245436 A1 | 9/2013 | Tupin | |
| 2013/0275152 A1 | 10/2013 | Moore et al. | |
| 2013/0316313 A1 | 11/2013 | Darrow | |
| 2014/0045156 A1 | 2/2014 | Alessandri | |
| 2014/0135631 A1 | 5/2014 | Brumback et al. | |
| 2014/0142403 A1 | 5/2014 | Park | |
| 2014/0156228 A1 | 6/2014 | Park | |
| 2014/0163927 A1 | 6/2014 | Molettiere et al. | |
| 2014/0180169 A1 | 6/2014 | Peters et al. | |
| 2014/0221791 A1 | 8/2014 | Andre | |
| 2014/0235166 A1 | 8/2014 | Park | |

(56) References Cited

U.S. PATENT DOCUMENTS

| | | |
|---|---|---|
| 2014/0164611 A1 | 9/2014 | Park |
| 2014/0249436 A1 | 9/2014 | Serguei et al. |
| 2014/0276244 A1 | 9/2014 | Kamyar |
| 2014/0357961 A1 | 12/2014 | Natarajan |
| 2014/0379273 A1 | 12/2014 | Mason |
| 2015/0004912 A1 | 1/2015 | Diamond et al. |
| 2015/0022366 A1 | 1/2015 | Vu et al. |
| 2015/0105646 A1 | 4/2015 | Peters |
| 2015/0190087 A1* | 7/2015 | Shinar ................. A61B 5/01 600/595 |
| 2015/0374328 A1 | 12/2015 | Ginestet et al. |
| 2016/0015315 A1 | 1/2016 | Auphan et al. |
| 2016/0058363 A1 | 3/2016 | Hayes-Gill et al. |
| 2016/0066827 A1 | 3/2016 | Workman et al. |
| 2016/0103590 A1 | 4/2016 | Vu et al. |
| 2016/0139787 A1 | 5/2016 | Heo |
| 2016/0157717 A1 | 6/2016 | Gaster et al. |
| 2016/0256132 A1 | 9/2016 | VandeLaar et al. |
| 2016/0262649 A1 | 9/2016 | Hayes-Gill et al. |
| 2016/0262687 A1 | 9/2016 | Vaidyanathan |
| 2016/0331299 A1 | 11/2016 | Cline |
| 2016/0374608 A1* | 12/2016 | Dugan ................. A61B 5/746 600/301 |
| 2017/0086709 A1 | 3/2017 | Khine |
| 2017/0156594 A1 | 6/2017 | Andre |
| 2017/0224268 A1 | 8/2017 | Dy |
| 2017/0319087 A1 | 11/2017 | Van De Laar |
| 2018/0296156 A1 | 10/2018 | Dy |
| 2019/0200916 A1 | 7/2019 | Hyde et al. |
| 2020/0085365 A1 | 3/2020 | McDonald et al. |
| 2020/0146614 A1 | 5/2020 | Cline et al. |
| 2020/0155027 A1 | 5/2020 | Lau et al. |
| 2020/0214618 A1 | 7/2020 | Vullings |
| 2022/0167911 A1 | 6/2022 | Brooker |

FOREIGN PATENT DOCUMENTS

| | | |
|---|---|---|
| CA | 2765124 A1 | 12/2010 |
| CA | 2870560 A1 | 10/2013 |
| EP | 1220640 B1 | 5/2008 |
| EP | 1941830 A2 | 7/2008 |
| EP | 1941832 A1 | 7/2008 |
| EP | 1680018 B1 | 11/2008 |
| EP | 2451345 A2 | 1/2011 |
| EP | 1952760 B1 | 4/2012 |
| EP | 2745774 A1 | 6/2014 |
| EP | 3011464 A1 | 12/2014 |
| EP | 2862511 A1 | 4/2015 |
| EP | 2328471 B1 | 9/2015 |
| EP | 2997892 A1 | 3/2016 |
| EP | 2185068 B1 | 9/2016 |
| WO | 2005110236 A1 | 11/2005 |
| WO | 2009013245 A1 | 1/2009 |
| WO | 2009150440 A1 | 12/2009 |
| WO | 2010105063 A1 | 9/2010 |
| WO | 2010144413 A1 | 12/2010 |
| WO | 2011004147 A2 | 1/2011 |
| WO | 2011094609 A2 | 8/2011 |
| WO | 2011119757 A2 | 9/2011 |
| WO | 2011130291 A2 | 10/2011 |
| WO | 2011130295 A2 | 10/2011 |
| WO | 2012061827 A1 | 5/2012 |
| WO | 2012131171 A1 | 10/2012 |
| WO | 2012142241 A2 | 10/2012 |
| WO | 2013052612 A2 | 4/2013 |
| WO | 2013158625 A1 | 10/2013 |
| WO | 2014035836 A1 | 3/2014 |
| WO | 2014162135 A1 | 10/2014 |
| WO | 2014205201 A1 | 12/2014 |
| WO | 2015013163 A1 | 1/2015 |
| WO | 2015020886 A1 | 2/2015 |
| WO | 2015056027 A1 | 4/2015 |
| WO | 2015063520 A1 | 5/2015 |
| WO | 2016131630 A1 | 8/2016 |

OTHER PUBLICATIONS

Faurholt-Jepsen, et al., "Electronic monitoring of psychomotor activity as a supplementary objective measure of depression severity", Nordic Journal of Psychiatry, vol. 69.

Haakstad et al., "Stages of change model for participations in physical activity during pregnancy", Journal of Pregnancy, vol. 2013, 2013, 7 pgs.

Hjortskov, et al., "The effect of mental stress on heart rate variability and blood pressure during computer work", European Journal of Applied Physiology, vol. 92, Issue 1.

Intille, S., "Ubiquitous Computing Technology for Just-in-Time Motivation of Behavior Change", Studies in Health Technology and Informatics, vol. 107, 2004, pp. 1434-1437.

Kenny, et al., "Novel biomarkers for pre-edampsia detected using metabolomics and machine learning", Metabolomics, vol. 1, Issue 3, 2005, pp. 227-234.

Lathia et al., "Smart phones for large-scale behavior change interventions", Proceedings of IEEE Pervasive Computing, 2013, pp. 2-9.

MacMahon, et al., Blood pressure, stroke, and coronary heart disease: part 1, prolonged differences in blood pressure: prospective observational studies corrected for the reg.

Moriya, et al., "Weekly averaged blood pressure is more important than a single-point blood pressure measurement in the risk stratification of dialysis patients", Clinical Jou.

Pickering, et al., "Ambulatory Blood-Pressure Monitoring", New England Journal of Medicine, vol. 354, 2006, pp. 2368-2374.

Rodriquez-Roisin, "Toward a Consensus Definition for COPD Exacerbations", Chest, vol. 117, Issue 5, Suppl 2, 2000, pp. 398S-401S.

Salah et al., "Human Behavior Understanding for Inducing Behavioral Change: Application Perspectives", Human Behavior Understanding, Lecture Notes in Computer Science, Volume.

Woolf, S.H., "The power of prevention and whatIt requires", Journal of the American Medical Association, vol. 299, 2008, pp. 2437-2439.

Zhou et al., "Getting Clinicians Involved: Testing Smartphone Applications to Promote Behavior Change in Health Care", May 31, 2012, Retrieved from Internet: URL:http://citenpl.

Dovetail Care, "Pregnansi", SimilarWeb Ltd, 2016, 7 pages.

Shulgin et al., "Electrohysterographic Signals Processing for Uterine Activity Detection ad Characterization", IEEE XXXIV International Scientific Conference Electronics and Nanotechnology, 2014, pp. 269-272.

Horoba, et al., "Statistical Approach to Analysis of Electrohysterographic Signal", Proceedings of the First Joint BMES/EMBS Conference, Atlanta, GA, 1999, pp. 887.

International Search Report dated Dec. 24, 2014 from International Application PCT/US2014/049280, 4 pgs.

Written Opinion of International Search Report dated Dec. 24, 2014 from International Application PCT/US2014/049280, 15 pgs.

De Lau Hinke et al., "Towards improving uterine electrical activity modeling and electrohysterography: ultrasonic quantification of uterine movements during labor.", Nordic Federation of Societies of Obstetrics and Gynecology, Acta Obstetricia et Gynecologica Scandinavica, 2013, 1323-1326, 92 (11).

Zimmer et al., "The relationship between uterine contractions, fetal movements and fetal heart rate patterns in the active phase of labor", Elsevier Science Publishers B.V. (Biomedical Division), 1987, 89-95, 25 (2).

International Search Report dated May 6, 2016 from International Application PCT/IB2015/002194, 7 pgs.

Written Opinion of International Search Report dated May 6, 2016 from International Application PCT/IB2015/002194, 11 pgs.

European Search Report and Written Opinon of European Search Report for Belgium National Application BE201505056, 18 pgs.

Supplementary European Search Report dated Feb. 17, 2017 for EP 14834450.0, 7 pgs.

Written Opinion of International Search Report dated Dec. 19, 2018 from International Application PCT/IB2018/055394, 12 pgs.

(56) References Cited

OTHER PUBLICATIONS

International Search Report dated Dec. 19, 2018 from International Application PCT/IB2018/055394, 8 pgs.
Lange, L. et al. "Velocity and Directionality of the Electrohysterographic Signal Propagation," Plos One, vol. 9, No. 1, Jan. 21, 2014, pp. 1-6.
Maner, W. et al. "Identification of Human Term and Preterm Labor using Artificial Neural Networks on Uterine Electromyography Data," Annuals of Biomedical Engineering, Kluwer Academic Publishers-Plem Publishers, NE, vol. 35, No. 3, Jan. 17, 2007, pp. 465-473.
Penders, J. et al. "Wearable Sensors for Healthier Pregnancies," IEEE, Proceedings of the IEEE, 2015, http://www.ieee.org/publications_standards/publications/rights/index.html.
"Altini et al. Combining wearable accelerometer and physiological data and energy expenditure estimation. Wireless Health, vol. 13, Nov. 1-3, 2013, 8 pages."
"Altini et al. Personalized Energy expenditure estimation using physiological signals normalization during activities of daily living. Physiological Measurement, vol. 35, Aug. 13, 2014, pp. 1797-1811."
"Chiuve et al, Healthy Lifestyle Factors in the Primary Prevention of Coronary Heart Disease Among Men: Benefits Among Users and Nonusers of Lipid-Lowering and Antihypertensive Medications, Circulation Journal of the American Heart Association, vol. 114, 160-167, Jul. 2006, 9 pages."
"Luoto et al., Pregnancy and Lifestyle: Short-and Long-Tem1 Effects on Mother's and Her Children's Health, Journal of Pregnancy, Hindawi Publishing Corporation, vol. 2013, 2 pages, May 2013."
"Hodsden, S. "GE Healthcare Expands Digital Offerings With Maternal-Infant Monitoring Acquisition" Med Device Online. Mar. 16, 2017 <https://www.meddeviceonline.com/doc/ge-healthcare-expands-digital-offerings-with-maternal-infant-monitoring-acquisition-0001> (Year 2017)".
"Internet Archive, Bloomlife.com, "How Bloomlife Works" Sep. 25, 2018. <https://web.archive.org/web/20180925151005/http://www.bloomlife.com/how-it-works/> (Year: 2018)".
"Jo, Young Chang, et al. "Wearable patch device for uterine EMG and preterm birth monitoring applications." TENCON 2018-2018 IEEE Region 10 Conference. IEEE, 2018. (Year: 2018)".
"NS Medical "Philips secures CE mark for new Avalon obstetrical care solution" NS Medical Devices. Sep. 14, 2018. <https://www.nsmedicaldevices.com/news/philips-ce-mark-avalon/> (Year: 2018)".

\* cited by examiner

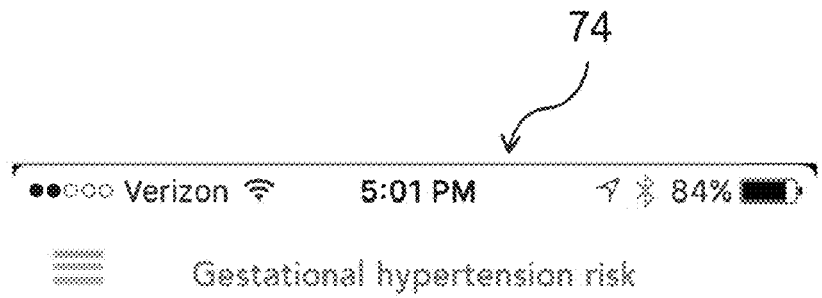

Entire U.S. population

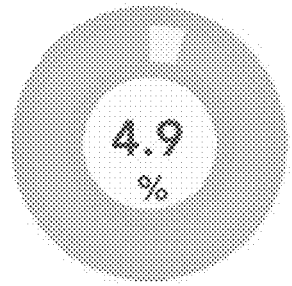

4.9% of women in the United States were diagnosed with gestational hypertension between 2012 and 2014

People similar to you

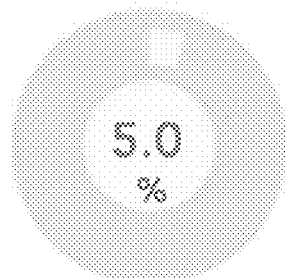

Among women with characteristics similar to yours, about 5.0% were diagnosed with gestational hypertension In this page you can see how your background data and previous pregnancies influence your overall risk of gestational hypertension with respect to other people You

Risk breakdown

You

Plurality

| You | +32.9% | +81.4% |
| One baby | Twins | Triplets |

Expecting twins, triplets or other multiple pregnancies are associated with higher risk of preterm birth

Height & weight before pregnancy

| +1.4% | You | -0.2% |
| Underweight | Normal weight | Overweight |

Studies shown that underweight women are at higher risk of preterm birth

Age

| +0.6% | You | +0.6% |

FIG. 29

SYSTEMS AND METHODS FOR MONITORING UTERINE ACTIVITY AND ASSESSING PRE-TERM BIRTH RISK

CROSS-REFERENCE TO RELATED APPLICATION

This application is the U.S. National Stage Application under 35 U.S.C. 371 for International PCT Patent Application PCT/IB2018/055394, filed Jul. 19, 2018, which claims priority benefits to U.S. Provisional Application Ser. No. 62/534,586, titled "Systems and Methods for Monitoring Uterine Activity", filed on Jul. 19, 2017, and U.S. Provisional Application Ser. No. 62/548,094, titled "Systems and Methods for Assessing Pre-Term Birth Risk", filed on Aug. 21, 2017, both of which are herein incorporated by reference in their entireties.

BACKGROUND

1. Field

This invention relates generally to the field of obstetrics, and more specifically to new and useful systems and methods for monitoring uterine activity and assessing pre-term birth risk.

2. Description of the Related Art

Pregnancy is an incredibly stressful time for an expectant mother. As her body changes in many ways during the pregnancy process, she must begin to discern between bodily changes that insinuate that her body is preparing for labor (e.g., Braxton Hicks contractions) versus changes that indicate true labor (e.g., real labor inducing contractions). Differentiating Braxton-Hicks contractions from real labor-inducing contractions can be very difficult for an expectant mother, especially a first-time mother. For example, an expectant mother may not feel or notice Braxton-Hicks contractions so when labor-inducing contractions start, she may not be able to determine if she is in labor or experiencing Braxton-Hicks contractions. Further for example, an expectant mother may experience painful or regular Braxton-Hicks contractions causing increased stress since she may repeatedly worry that she is in labor. Alternatively, an expectant mother may wrongly conclude that her contractions are Braxton-Hicks contractions when in reality they are true pre-term labor contractions or term labor-inducing contractions.

Early contraction monitoring devices, for example Home Uterine Activity Monitors, were cumbersome and required the patient to remember to wear the device daily for short periods of time, collect the data, and transmit the data to a center. In addition, such devices did not provide any feedback to the pregnant woman and could therefore create additional anxiety with regards to the outcome of the monitoring. Home Uterine Activity Monitors were intended for patients at risk of preterm labor, in order to monitor preterm labor onset from home. However, multiple studies have showed that these monitors did not improve outcomes. Such devices are no longer covered by most health insurance providers and the American College of Obstetrics and Gynecology has cast doubt on the efficacy of such devices. Other devices that sought to remedy these shortcomings focused on more continuous monitoring of uterine muscle contractions and frequency-based algorithms to detect aberrant uterine activity but failed to definitively detect and differentiate Braxton-Hicks and labor-inducing contractions.

Other systems for monitoring labor include invasive probes or devices inserted into the uterus (post membrane rupture) or on the cervix to monitor uterine contractions. Such systems are not safe for continuous use and are not suitable for in-home and/or personal use (i.e., without a healthcare provider).

Additional systems and methods in current use are the bishop score, cervical length measurement, and tocodynamometry (TOCO). The bishop score combines cervical dilation, cervical effacement, cervical consistency, cervical position, and fetal station measured during a vaginal examination. Cervical length measurements (e.g., using transvaginal sonography) use vaginal ultrasound imaging to approximate the length of the cervix, where a short cervix indicates a higher risk for preterm labor. Lastly, TOCO uses an external pressure probe to measure contractions. TOCO is typically used to measure contraction frequency and length but fails to capture information about the amplitude of a contraction. TOCO is also very susceptible to probe positioning and measurement artifacts such as fetal movements. While these systems and methods may be useful in a clinical setting to give an approximate labor or contraction status when performed by a healthcare provider, they completely fail to capture the real physiological phenomenon behind contractions, that is the electrical activity of the uterine muscle. Consequently, they fail to distinguish Braxton-Hicks contractions from labor inducing contractions, pre-term or term.

In other additional situations, a baby born prematurely may experience a lifetime of intellectual and developmental disabilities or delays and/or health problems and conditions. For example, a premature baby may experience disabilities or delays related to: physical development, learning, and social skills. Long-term disabilities or conditions caused by premature birth may include: behavior problems, anxiety, neurological disorders (e.g., cerebral palsy), autism, lung or breathing disorders, asthma, bronchopulmonary dysplasia, intestinal disorders, decreased immunity (e.g., to infections), vision problems (e.g., retinopathy of prematurity), hearing loss, and dental problems (e.g., delayed tooth growth, changes in tooth color, or teeth that grow crooked or out of place). Thus, to improve neonatal health and wellbeing and reduce future healthcare costs, assessing and managing pre-term birth risk is crucial.

Current systems and methods for assessing pre-term birth risk include: measuring biomarkers of the pregnant female, assessing the pregnant female's health history and/or lifestyle, and monitoring for contractions indicative of pre-term labor, among other systems and methods. These systems and methods focus on substantially fixed parameters that a pregnant female cannot alter to improve her pre-term birth risk score. These systems and methods do not allow or enable the pregnant female to change different physiological, behavioral, and/or biological characteristics to improve her pre-term birth risk or provide feedback to the pregnant female or healthcare provider to adapt therapy and/or consultation.

Thus, there is a need for systems and methods for detecting contractions, and more specifically, for differentiating Braxton-Hicks contractions from labor-inducing contractions and assessing pre-term birth risk, outside of supervised laboratory or clinical settings.

SUMMMARY

The following is a non-exhaustive listing of some aspects of the present techniques. These and other aspects are described in the following disclosure.

Some aspects include a system for uterine activity monitoring, the system including: a plurality of sensors coupled to a belly region of a pregnant female; a processor communicatively coupled to the plurality of sensors; and a computer-readable medium having non-transitory, processor-executable instructions stored thereon, wherein execution of the instructions causes the processor to perform a method including: acquiring a plurality of signals from the plurality of sensors during uterine activity, processing the plurality of signals to extract a plurality of uterine electrical activity characteristics, analyzing the plurality of uterine electrical activity characteristics, and classifying the uterine activity as one of: a preterm labor contraction, a labor contraction, a Braxton-Hicks contraction, and a state of no contraction, based at least in part on the plurality of uterine electrical activity characteristics.

In some embodiments, the plurality of uterine electrical activity characteristics includes at least two of: a uterine electrical activity frequency, a uterine electrical activity amplitude over time, a uterine electrical activity duration over time, a directionality of uterine electrical activity, and a velocity of uterine electrical activity.

In some embodiments, the directionality or velocity of uterine electrical activity is determined by sensing a uterine electrical activity movement or propagation over time between at least three sensors.

In some embodiments, analyzing the plurality of uterine electrical activity characteristics is performed using machine learning techniques.

In some embodiments, the method performed by the processor further includes: processing the plurality of signals to extract a maternal characteristic during the uterine activity; and correlating the maternal characteristic with the plurality of uterine electrical activity characteristics, wherein the uterine activity is classified as one of: a preterm labor contraction, a labor contraction, a Braxton-Hicks contraction, or a state of no contraction, based at least in part on the plurality of uterine electrical activity characteristics and the maternal characteristic.

In some embodiments, the maternal characteristic includes one or more of: a maternal heart rate, a maternal heart rate variability, a maternal respiration rate, a maternal respiration intensity, a maternal galvanic skin response, and a maternal skin or body temperature.

In some embodiments, the method performed by the processor further includes: analyzing the plurality of uterine electrical activity characteristics over time to identify one or more changes; and correlating the maternal characteristic with the one or more changes in the plurality of uterine electrical activity characteristics.

In some embodiments, the method performed by the processor further includes: processing the plurality of signals to extract a deformation of the belly region of the pregnant female; and correlating the deformation of the belly region with the plurality of uterine electrical activity characteristics, wherein the uterine activity is classified as one of: a preterm labor contraction, a labor contraction, a Braxton-Hicks contraction, and a state of no contraction, based at least in part on the plurality of uterine electrical activity characteristics and the deformation of the belly region.

In some embodiments, the deformation of the belly region is measured by one of: an inertial sensor, a piezo-electric sensor, a piezo-resistive sensor, a capacitive sensor, a pressure sensor, and a stretch sensor.

In some embodiments, the method performed by the processor further includes: analyzing the plurality of uterine electrical activity characteristics over time to identify one or more changes; and correlating the deformation of the belly region with one or more changes in the plurality of uterine electrical activity characteristics.

In some embodiments, the plurality of sensors is coupled to a wearable accessory.

In some embodiments, the wearable accessory is one of: a belly patch and a belly belt.

In some embodiments, the plurality of sensors is positioned on or in a portable and wearable sensor module, the sensor module further including an electronic circuit and a wireless antenna, and wherein the sensor module is in wireless communication with a computing device including the processor and the computer-readable medium.

In some embodiments, the computing device is a mobile computing device.

In some embodiments, the mobile computing device is selected from a group consisting of: a smartphone, a smart watch, smart glasses, smart contact lenses, other wearable computer, a tablet, a laptop, and a personal computer.

In some embodiments, the method performed by the processor further includes: generating an alert.

In some embodiments, the method performed by the processor further includes: notifying a user of the uterine activity or a classification of the uterine activity as one of: the preterm labor contraction, the labor contraction, the Braxton-Hicks contraction, and the state of no contraction.

In some embodiments, the method performed by the processor further includes: recommending a course of action to a user based on the detected uterine activity and a classification of the uterine activity.

In some embodiments, the user is one or more of: a partner, a pregnant female, a healthcare provider, a doula, a midwife, a friend, a family member, an emergency service provider, and a transportation service provider.

In some embodiments, the method performed by the processor further includes: determining a probability that the pregnant female is experiencing one of: preterm labor contractions, term labor contractions, Braxton-Hicks contractions (i.e., non-labor inducing), and no contractions.

In some embodiments, the method performed by the processor further includes: determining a degree of certainty around the determined probability.

In some embodiments, the method performed by the processor further includes: displaying on a computing device communicatively coupled to the processor a visual representation of the uterine activity or a series of uterine activities.

Some aspects include a system for uterine activity monitoring, the system including: a plurality of sensors coupled to a belly region of a pregnant female; a processor communicatively coupled to the plurality of sensors; and a computer-readable medium having non-transitory, processor-executable instructions stored thereon, wherein execution of the instructions causes the processor to perform a method including: acquiring a plurality of signals from the plurality of sensors during a series of uterine activities, processing the plurality of signals to extract a plurality of uterine electrical activity characteristics of the series of uterine activities, analyzing the plurality of uterine electrical activity characteristics of the series of uterine activities to identify a pattern, and classifying the pattern as one of: a preterm labor contraction, a labor contraction, a Braxton-Hicks contraction, and a state of no contraction.

In some embodiments, the pattern of the plurality of uterine electrical activity characteristics includes at least one of: a time interval between uterine electrical activities, a change in uterine electrical activity frequency, a change in uterine electrical activity amplitude, a change in uterine electrical activity duration, a change in uterine electrical activity directionality, and a change in uterine electrical activity velocity.

In some embodiments, the method performed by the processor further includes: processing the plurality of signals to extract a maternal characteristic during, in-between, before, or after the series of uterine activities; and correlating the maternal characteristic with the plurality of uterine electrical activity characteristics, wherein the uterine activity is classified as one of: a preterm labor contraction, a labor contraction, a Braxton-Hicks contraction, and a state of no contraction, based at least in part on the plurality of uterine electrical activity characteristics and the maternal characteristic.

Some aspects include a method of uterine activity monitoring, the method including: acquiring a plurality of signals from a plurality of sensors during uterine activity, wherein the plurality of sensors is coupled to a belly region of a pregnant female; processing the plurality of signals to extract a plurality of uterine electrical activity characteristics; analyzing the plurality of uterine electrical activity characteristics; and classifying the uterine activity as one of: a preterm labor contraction, a labor contraction, a Braxton-Hicks contraction, and a state of no contraction, based at least in part on the plurality of uterine electrical activity characteristics.

In some embodiments, the method includes processing the plurality of signals to extract a maternal characteristic during, before, or after the uterine activity.

In some embodiments, the method includes correlating the maternal characteristic with the plurality of uterine electrical activity characteristics to identify the uterine activity as one of: a preterm labor contraction, a labor contraction, a Braxton-Hicks contraction, and a state of no contraction.

In some embodiments, the method further includes analyzing the plurality of uterine electrical activity characteristics over time to identify one or more changes; and correlating the maternal characteristic with the one or more changes in the plurality of uterine electrical activity characteristics.

In some embodiments, the maternal characteristic includes one or more of: a maternal heart rate, a maternal heart rate variability, a maternal respiration rate, a maternal respiration intensity, a maternal galvanic skin response, and a maternal skin or body temperature.

In some embodiments, the plurality of uterine electrical activity characteristics includes at least two of: a uterine electrical activity frequency, a uterine electrical activity amplitude over time, a uterine electrical activity duration over time, a directionality of uterine electrical activity, and a velocity of uterine electrical activity.

In some embodiments, the method further includes processing the plurality of signals to extract a deformation of the belly region of the pregnant female.

In some embodiments, the method further includes analyzing the plurality of uterine electrical activity characteristics over time to identify one or more changes; and correlating the deformation of the belly region with one or more changes in the plurality of uterine electrical activity characteristics.

In some embodiments, wherein the uterine activity includes a series of uterine activities.

In some embodiments, the method further includes analyzing the plurality of uterine electrical activity characteristics of the series of uterine activities to identify a pattern, and classifying the pattern as one of: a preterm labor contraction, a labor contraction, a Braxton-Hicks contraction, and a state of no contraction.

Some aspects include a system for assessing over time a pre-term birth risk of a pregnant female, the system including a sensor configured to be worn on a belly region of the pregnant female; a processor communicatively coupled to the sensor; and a computer-readable medium having non-transitory, processor-executable instructions stored thereon, wherein execution of the instructions causes the processor to perform a method including: calculating a baseline pre-term birth risk score based on a user input; acquiring, over time, a signal from a sensor; analyzing the signal to extract a parameter of interest, wherein the parameter of interest includes a physiological parameter; and calculating an instant pre-term birth risk score based, at least in part, on the parameter of interest and the user input.

In some embodiments, the system further includes a computing device communicatively coupled to the processor, wherein the method performed by the processor further includes: receiving the user input with the computing device.

In some embodiments, the computing device is one of: a laptop, a desktop, a netbook, a notebook, a mobile device, a personal digital assistant, a smart phone, a smart watch, and a wearable device.

In some embodiments, the system further includes an antenna, wherein the antenna functions as a receiver to receive the user input from a computing device communicatively coupled to the processor.

In some embodiments, the system further includes an antenna, wherein the antenna functions as a transmitter to transmit one or more of the baseline pre-term birth risk score and the instant pre-term birth risk score to a computing device communicatively coupled to the system.

In some embodiments, the method performed by the processor further includes: receiving the user input, wherein the user input includes of one or more of: a health history of the pregnant female, one or more demographics of the pregnant female, a lifestyle of the pregnant female, and a number of fetuses being carried by the pregnant female.

In some embodiments, the lifestyle of the pregnant female includes one or more of: an exercise schedule of the pregnant female, a medical drug regimen of the pregnant female, an alcohol consumption metric of the pregnant female, a smoking habit of the pregnant female, a recreational drug use habit of the pregnant female, a coitus schedule of the pregnant female, an eating habit of the pregnant female, and a frequency of traveling of the pregnant female.

In some embodiments, the method performed by the processor further includes: providing a recommendation to the pregnant female to maintain or improve the instant pre-term birth risk score.

In some embodiments, the recommendation includes one or more of: a change in an activity level, reduce or stop smoking, reduce or stop alcohol consumption, increase an amount of rest, decrease a stress level (e.g., breathing exercise, meditation, mindfulness session, etc.), drink more water, increase an amount of sleep, increase an amount of healthy foods consumed, reduce or stop drug use, a change in caloric intake, and a change in a medication regimen.

In some embodiments, the method performed by the processor further includes: providing one or more of: the baseline pre-term birth risk score and the instant pre-term birth risk score to a healthcare provider.

In some embodiments, the method performed by the processor further includes: categorizing a group of pregnant females according to one or more of: their baseline pre-term birth risk score and their instant pre-term birth risk score.

In some embodiments, the method performed by the processor further includes: varying a treatment based on one or more of: the baseline pre-term birth risk score and the instant pre-term birth risk score.

In some embodiments, the method performed by the processor further includes: adapting prenatal care based on one or more of: the baseline pre-term birth risk score and the instant pre-term birth risk score.

In some embodiments, the method performed by the processor further includes: receiving a biological data input; and calculating the instant pre-term birth risk score based, at least in part, on the biological data input.

In some embodiments, the biological data input includes one or more of: a biological test result, a blood test result, an ultrasound screening result, a vaccination record, proteomics data, genetic data, serum test results, and an amniocentesis result.

In some embodiments, calculating includes using Bayesian linear regression.

In some embodiments, calculating is performed using machine learning techniques.

In some embodiments, the physiological parameters include one or more of: a contraction wave amplitude, a contraction wave frequency over time, a directionality of a contraction wave, a velocity of contraction wave propagation, a contraction wave duration over time, a resting heart rate, a resting heart rate variability, a blood pressure level, a blood glucose level, an oxygen saturation level, a weight, a heartbeat of a fetus, a heart rate of a fetus, a heart rate variability of a fetus, a position of a fetus, and a weight of a fetus.

In some embodiments, the method performed by the processor further includes: comparing the parameter of interest to one or more references, wherein the one or more references identify individual characteristics of a population associated with pre-term birth; calculating a probability that the parameter of interest of the pregnant female is associated with pre-term birth based on the one or more references; and calculating the instant pre-term birth risk score based, at least in part, on the calculated probability.

In some embodiments, the one or more references include one or more of: a database, a publication, a presentation, and a website.

In some embodiments, the method performed by the processor further includes: displaying one or more of: the baseline pre-term birth risk score and the instant pre-term birth risk score to the pregnant female or another user.

In some embodiments, the method performed by the processor further includes: displaying a series of factors that influence one or more of: the baseline pre-term birth risk score and the instant pre-term birth risk score to the pregnant female.

In some embodiments, the signal includes a plurality of signals.

In some embodiments, the sensor includes a plurality of sensors.

In some embodiments, the parameter of interest includes a plurality of parameters of interest.

In some embodiments, the physiological parameters include a plurality of physiological parameters.

In some embodiments, the method performed by the processor further includes: determining a behavioral parameter based one or more physiological parameters; and calculating the instant pre-term birth risk score based, at least in part, on the behavioral parameter.

In some embodiments, the behavioral parameter includes one or more of: a stress level of the pregnant female, a sleep quality of the pregnant female, an activity level of the pregnant female, a calorie expenditure of the pregnant female, a cardiorespiratory fitness level of the pregnant female, an activity level of a fetus, and a wellbeing of a fetus.

In some embodiments, the method performed by the processor further includes: displaying the behavioral parameter to the pregnant female or another user.

In some embodiments, the method performed by the processor further includes: when the instant pre-term birth risk score differs from the baseline pre-term birth risk score, updating the baseline pre-term birth risk score with the instant pre-term birth risk score.

In some embodiments, the system further including a patch or belt coupled to the sensor and configured to position the sensor against a skin surface of the belly region of the pregnant female.

Some aspects include a method of assessing over time a pre-term birth risk of a pregnant female, the method including: calculating a baseline pre-term birth risk score based on a user input; acquiring, over time, a signal from a sensor; analyzing the signal to extract a parameter of interest, wherein the parameter of interest includes a physiological parameter; and calculating an instant pre-term birth risk score based, at least in part, on the parameter of interest and the user input.

In some embodiments, the method further includes receiving the user input, wherein the user input includes of one or more of: a health history of the pregnant female, one or more demographics of the pregnant female, a lifestyle of the pregnant female, and a number of fetuses being carried by the pregnant female.

In some embodiments, the lifestyle of the pregnant female includes one or more of: an exercise schedule of the pregnant female, a medical drug regimen of the pregnant female, an alcohol consumption metric of the pregnant female, a smoking habit of the pregnant female, a recreational drug use habit of the pregnant female, a coitus schedule of the pregnant female, an eating habit of the pregnant female, and a frequency of traveling of the pregnant female.

In some embodiments, the method further includes providing a recommendation to the pregnant female to maintain or improve the instant pre-term birth risk score.

In some embodiments, the recommendation includes one or more of: a change in an activity level, reduce or stop smoking, reduce or stop alcohol consumption, increase an amount of rest, decrease a stress level (e.g., breathing exercise, meditation, mindfulness session, etc.), drink more water, increase an amount of sleep, increase an amount of healthy foods consumed, reduce or stop drug use, a change in caloric intake, and a change in a medication regimen.

In some embodiments, the method further includes providing one or more of: the baseline pre-term birth risk score and the instant pre-term birth risk score to a healthcare provider.

In some embodiments, the method further includes categorizing a group of pregnant females according to one or more of: their baseline pre-term birth risk score and their instant pre-term birth risk score.

In some embodiments, the method further includes varying a treatment based on one or more of: the baseline pre-term birth risk score and the instant pre-term birth risk score.

In some embodiments, the method further includes adapting prenatal care based on one or more of: the baseline pre-term birth risk score and the instant pre-term birth risk score.

In some embodiments, the method further includes receiving a biological data input; and calculating the instant pre-term birth risk score based, at least in part, on the biological data input.

In some embodiments, biological data input includes one or more of: a biological test result, a blood test result, an ultrasound screening result, a vaccination record, proteomics data, genetic data, serum test results, and an amniocentesis result.

In some embodiments, calculating includes using Bayesian linear regression.

In some embodiments, calculating is performed using machine learning techniques.

In some embodiments, the physiological parameters include one or more of: a contraction wave amplitude, a contraction wave frequency over time, a directionality of a contraction wave, a velocity of contraction wave propagation, a contraction wave duration over time, a resting heart rate, a resting heart rate variability, a blood pressure level, a blood glucose level, an oxygen saturation level, a weight, a heartbeat of a fetus, a heart rate of a fetus, a heart rate variability of a fetus, a position of a fetus, and a weight of a fetus.

In some embodiments, the method further includes comparing the parameter of interest to one or more references, wherein the one or more references identify individual characteristics of a population associated with pre-term birth; calculating a probability that the parameter of interest of the pregnant female is associated with pre-term birth based on the one or more references; and calculating the instant pre-term birth risk score based, at least in part, on the calculated probability.

In some embodiments, the one or more references include one or more of: a database, a publication, a presentation, and a website.

In some embodiments, the method further includes displaying one or more of: the baseline pre-term birth risk score and the instant pre-term birth risk score to the pregnant female or another user.

In some embodiments, the method further includes displaying a series of factors that influence one or more of: the baseline pre-term birth risk score and the instant pre-term birth risk score to the pregnant female.

In some embodiments, the signal includes a plurality of signals.

In some embodiments, the sensor includes a plurality of sensors.

In some embodiments, the parameter of interest includes a plurality of parameters of interest.

In some embodiments, wherein the physiological parameters include a plurality of physiological parameters.

In some embodiments, the method further including: determining a behavioral parameter based one or more physiological parameters; and calculating the instant pre-term birth risk score based, at least in part, on the behavioral parameter.

In some embodiments, the behavioral parameter includes one or more of: a stress level of the pregnant female, a sleep quality of the pregnant female, an activity level of the pregnant female, a calorie expenditure of the pregnant female, a cardiorespiratory fitness level of the pregnant female, an activity level of a fetus, and a wellbeing of a fetus.

In some embodiments, the method further includes displaying the behavioral parameter to the pregnant female or another user.

In some embodiments, the method further includes when the instant pre-term birth risk score differs from the baseline pre-term birth risk score, updating the baseline pre-term birth risk score with the instant pre-term birth risk score.

Some aspects include a system for assessing over time a pre-term birth risk of a pregnant female, the system including: a first sensor configured to be worn on a belly region of the pregnant female; a second sensor coupled to or housed within a health monitoring device; a processor communicatively coupled to the first and second sensors; and a computer-readable medium having non-transitory, processor-executable instructions stored thereon, wherein execution of the instructions causes the processor to perform a method including: acquiring, over time, a first signal from the first sensor and a second signal from the second sensor; analyzing the first and second signals to extract one or more parameters of interest, wherein the one or more parameters of interest include one or more physiological parameters; and calculating an instant pre-term birth risk score based, at least in part, on the one or more parameters of interest.

In some embodiments, the health monitoring device is one of: an activity tracker, a weight scale, a blood pressure monitor, a blood glucose monitor, a thermometer, and a pacemaker.

BRIEF DESCRIPTION OF THE DRAWINGS

The above-mentioned aspects and other aspects of the present techniques will be better understood when the present application is read in view of the following figures in which like numbers indicate similar or identical elements.

FIG. 28 illustrates one embodiment of a graphical user interface configured to display a breakdown of a user's pre-term birth risk score.

FIG. 29 illustrates one embodiment of a graphical user interface configured to display a breakdown of a user's pre-term birth risk score.

Figure 1:
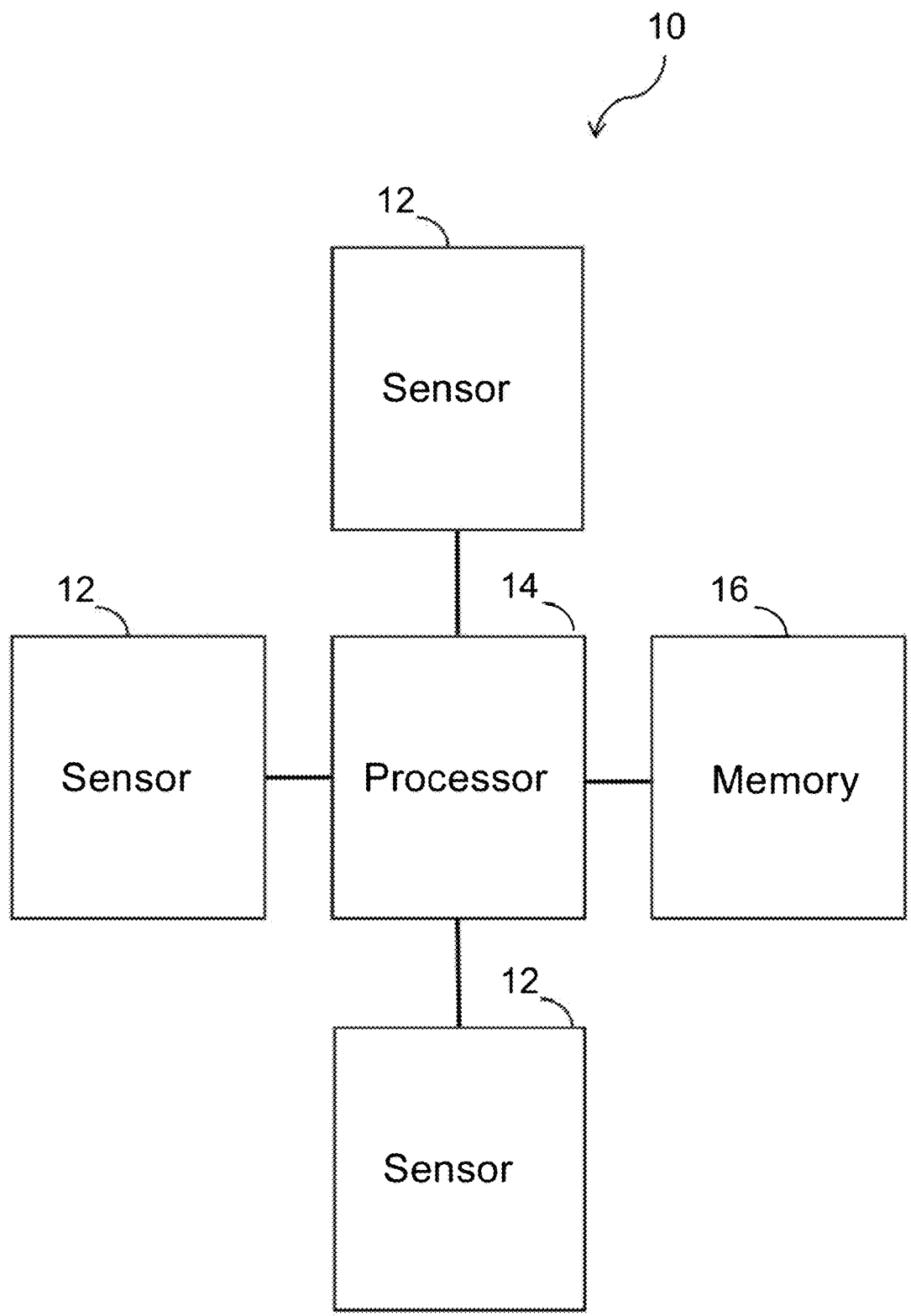
FIG. 1 depicts a block diagram of one embodiment of a system for uterine activity monitoring.

While the present techniques are susceptible to various modifications and alternative forms, specific embodiments thereof are shown by way of example in the drawings and will herein be described in detail. The drawings may not be to scale. It should be understood, however, that the drawings and detailed description thereto are not intended to limit the present techniques to the particular form disclosed, but to the contrary, the intention is to cover all modifications, equivalents, and alternatives falling within the spirit and scope of the present techniques as defined by the appended claims.

DETAILED DESCRIPTION OF CERTAIN EMBODIMENTS

To mitigate the problems herein, the inventors had to both invent solutions and, in some cases just as importantly, reorganize problems overlooked (or not yet foreseen) by others in the field of fetal health. Indeed, the inventors wish to emphasize the difficulty of recognizing these problems that are nascent and will become more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

Contractions are the periodic tightening and relaxing of the uterine muscle, the largest muscle in a woman's body. During a contraction, the abdomen becomes hard to the touch. In the childbirth process, the work of labor is done through a series of contractions called labor contractions. These contractions cause the upper part of the uterus (fundus) to tighten and thicken while the cervix and lower portion of the uterus stretch and relax, helping the baby pass from inside the uterus and into the birth canal for delivery. Contractions occur early in pregnancy but are generally weak, irregular, and often unfelt until the seventh or eighth month of pregnancy. Little or no change occurs in the cervix during these pre-labor contractions, sometimes referred to as false labor or Braxton-Hicks contractions.

Current methods for detecting contractions or diagnosing true labor depend on time-related (e.g., duration of uterine EMG 'bursts'), amplitude-related (e.g., uterine EMG signal power, EMG signal energy, power spectrum peak amplitude), and/or frequency-related (e.g., power spectrum median frequency, power spectrum peak frequency) electromyography (EMG) parameters. Although these EMG parameters are interesting, their predictive power for identifying labor-inducing contractions versus Braxton-Hicks contractions is limited (Lucovnik et al. 2011. 90(2): 150-157. *Acta Obstet Gyencol Scand*).

Some research in the area of contraction monitoring has focused on using conduction velocity of uterine contractions to predict preterm labor or to monitor fetal and maternal wellbeing. While this research has elucidated interesting insights, the findings fail to provide applicable systems and methods for differentiating different types of contractions. For example, Lucovnik and colleagues (Lucovnik et al., 2011. "Noninvasive Uterine Electromyography for Prediction of Preterm Delivery." *Am J Obstet Gynecol*, 204(3)) describe using conduction velocity to predict preterm labor. However, their findings were limited since using two electrodes overestimated the conduction velocity and their techniques could not discern the direction of propagation or discern the influence of propagation direction on conduction velocity.

Rabotti and colleagues (Rabotti et al., 2010. "Modeling and Identification of the Electrohysterographic Volume Conductor by High-Density Electrodes." *IEEE Trans Biomed Eng*, 57(3): 519-527) attempted to resolve the inadequacies of the Lucovnik study by including conduction velocity and wave propagation direction in their study using a 64-channel high-density grid to assess uterine electrical activity. While the results of Rabotti and colleagues were able to accurately detect conduction velocity, the application of this technology for non-clinical use and to discern between contraction types is unlikely. For example, if a velocity and/or directionality of Braxton-Hicks contractions were similar to that of true labor contractions, the device of Rabotti and colleagues would be unable to differentiate Braxton-Hicks from true labor contractions. Further, current methods to measure conduction velocity (described above and in other studies not described herein) require a grid of monopolar electrodes, assume a single wave, suffer from high noise in the signal especially early in pregnancy, and require automatic detection and matching.

Accordingly, a need exists for systems and methods that can be used by a pregnant woman in any environment to monitor her uterine activity, for example to determine the type of contraction(s) she is experiencing. In particular, a need exists for systems and methods that can monitor and analyze contractions and other physiological signs to determine whether a woman is, or soon will be, in labor or is experiencing Braxton-Hicks contractions. At least some of the systems and methods disclosed herein fill this need.

Additionally, premature birth is a huge concern during a pregnancy. Pre-term labor is defined as labor before 37 weeks gestation and is the most common obstetric complication. It occurs in about 20% of pregnant worldwide and is a major cause of perinatal illness and death. Increased uterine contractions may be a sign of pre-term labor, and tocolytic therapy can inhibit the onset of labor, or prolong the pregnancy, giving time for treatment to improve the baby's health. However, many women do not recognize these contractions in time for treatment. If such situations could be identified in the home, free-living environment, with different monitoring tools, clinical personnel, such as obstetrician, could intervene in a timely fashion and possibly improve health outcomes.

Many factors that may promote premature birth are unknown, however, there are factors, such as the following, that have been linked to premature birth: having a previous premature birth; pregnancy with twins, triplets or other multiples; an interval of less than six months between pregnancies; conceiving through in vitro fertilization; problems with the uterus, cervix or placenta; smoking cigarettes or using illicit drugs; poor nutrition; not gaining enough weight during pregnancy; some infections, particularly of the amniotic fluid and lower genital tract; some chronic conditions, such as high blood pressure and diabetes; being underweight or overweight before pregnancy; stressful life events, such as the death of a loved one or domestic violence; multiple miscarriages or abortions; and physical injury or trauma.

Current systems and methods may monitor a subset of these known risk factors but are unable to monitor all of these risk factors consistently and over time. Further, additional risk factors that are less well characterized or that can be extrapolated from population data are currently not part of the monitoring process. Thus, there exists a need for systems and methods for monitoring pre-term birth risk over time, for example pre-conception and throughout pregnancy.

Currently, one of the keys to treating preterm labor is early detection or prediction. As mentioned above, hospitals often use pressure transducers (TOCO) placed on the abdomen for basic noninvasive monitoring of uterine activity. However, TOCO is not a reliable technique and is unable to determine if labor is approaching.

A promising noninvasive marker of labor and pre-term labor is the electrical activity of the uterus, or electrohysterogram (EHG). EHG is a very promising tool for different applications, from per-term prediction to contraction and labor detection. One of the earliest signs of labor is a change in uterine activity, typically reflected as an increase in frequency and regularity of uterine contractions. Recent developments in wearable sensor technology, as well as signal processing and machine learning have made it possible to detect changes in uterine activity and contractions non-invasively. Analysis of the electrical activity of the uterus, or electrohystergraphy (EHG), reflects the source of the contractions.

Uterine contractions are generated by the electrical activity originating from the depolarization-repolarization of smooth muscle myometrial cells, thus, creating intermittent bursts of spike-like action potentials. This electrical activity is low and uncoordinated early in gestation, but becomes intense and synchronized later in pregnancy, peaking at term, hence motivating the use of EHG measurements to detect changes.

Changes in uterine activity that may be measured using EHG are only part of a multitude of alterations in physiology and anatomy occurring during pregnancy. Dramatic changes in cardiac output may be detected, with an increase up to 12% between contractions and 24% closer to delivery, which might derive from increased stroke volume already starting during the first phase of labor. Additionally, maternal heart rate (HR) accelerations result in high amplitude and duration and are synchronized with uterine contractions, making maternal cardiac activity another non-invasive parameter well representative of physiological changes with labor onset.

Together with changes in EHG, consistent changes in cardiac activity during labor are detected, therefore, making maternal heart rate (HR) a useful predictor in detection of labor from physiological data. However, it has been difficult to investigate such changes in EHG and HR outside of supervised laboratory or clinical settings.

Measuring and collecting data in unsupervised free-living conditions, e.g., at home, has become more common as wearable sensors are being used by expecting mothers. While many of these devices are customer gadgets, several are clinically validated tools and have been released to market. Such devices and sensors that have been validated rigorously under supervised laboratory conditions, it can be challenging to trust data acquired in free-living conditions, as use and misuse of the system is outside of the supervision of researchers.

Wearable sensors are able to acquire physiological data noninvasively and, together with recent advances in signal processing and machine learning techniques provided herein, are a way to passively and safely investigate changes in EHG and HR during labor and potentially provide pregnant women with a tool having the ability to detect labor outside of hospital settings.

Recent efforts have focused on trying to discriminate between term and pre-term deliveries using EHG recordings collected early in pregnancy. While reported results are promising, issues on methodology and oversampling techniques have been raised, as datasets were overfitted. Other studies have shown that the analysis of the propagation, or synchronization, of the uterine electrical activity is a powerful tool to characterize and discriminate pregnancy and labor contractions, after contractions have been manually isolated. Currently, no such systems and methods exist to address the issue of classifying physiological measurements (EHG and HR) collected non-invasively during pregnancy in labor and non-labor classes.

As mentioned above, currently there is no such systems and methods that can monitor the three phases of labor (i.e., early labor phase, the time of the onset of labor until the cervix is dilated to 3 cm; active labor phase, cervix is dilated from 3 cm until the cervix is dilated to 7 cm; and transition phase, cervix is dilated from 7 cm until the cervix is fully dilated to 10 cm), going from more regular contractions to delivery. The ability to detect labor non-invasively, outside of a hospital environment, may help expecting mothers avoid unnecessary visits, receive better care, as well as improve detection and management of pregnancy contractions, such as pre-term birth.

Some embodiments mitigate some or all of the problems discussed above by developing artifact and labor probability estimation models using data collected under supervised laboratory settings, for example, by combining EHG and HR data acquired at different gestational ages in a sample of pregnant women, respectively. This may allow the ability to identify artifacts and labor with high accuracy.

Some embodiments mitigate some or all of the problems discussed above by deploying artifact and labor probability estimation models in free-living environments where no data was collected during model development. This may allow the ability to identify high quality data and show that the probability of being in labor for recordings during the last 24 hours of a pregnancy is consistently higher than the probability during any other pregnancy week.

Some embodiments mitigate some or all of the problems discussed above by providing outside clinical diagnosis and labor detection systems and methods that provide just in time care, reduce healthcare costs, and provide better care by avoiding unnecessary antenatal visits. In addition, preterm birth and early contractions may be better diagnosed, therefore improving prenatal care and treatment for pre-term labor.

Some embodiments mitigate some or all of the problems disclosed above by combining EHG and HR data for labor detection to provide higher accuracy in detecting labor to analyze physiological signal properties over long periods of time.

Some embodiments mitigate some or all of the problems discussed above by combining time and frequency domain features extracted from EHG and HR signals in order to discriminate labor and non-labor recordings acquired with a single wearable device, analyzing different feature sets, including gestational age (GA), EHG and HR data, showing optimal results, for an overall accuracy of approximately 87%.

Disclosed herein are systems and methods for assessing a labor condition and/or pre-term birth risk. The systems and methods described herein are configured for use by a user. A user may include: a female pre-conception, a pregnant female, a partner of a pregnant female, a healthcare provider, gynecologist, obstetrician, a doula, a birth coach, a midwife, a nurse, or any person involved in pregnancy health management.

In general, the systems and methods described herein include a sensor module used to monitor contractions, determine contraction types, and assess pre-term birth risk in a pregnant woman (i.e., a pregnant female human) or other pregnant female animal. Results of the monitoring may be provided to the pregnant woman being monitored and/or to another user, for example a gynecologist; obstetrician; other physician; nurse practitioner; veterinarian; other healthcare provider; doula; midwife; other birthing specialist; spouse; partner; parent; sibling; other family member; friend; a healthcare facility administrator; a service provider who may provide ride-sharing, taxi, childcare, or other services to a woman in labor; an emergency service; or any other individual with whom the pregnant woman wishes to share such information.

As used herein, "pregnant woman" and "pregnant female" may be used interchangeably. It will be appreciated by one skilled in the art that each of the embodiments described herein may be used to monitor and detect a contraction type in any pregnant mammal regardless of species.

As described herein, "a Braxton-Hicks contraction" refers to generally less painful, irregular, low amplitude uterine electrical activity not leading to labor and delivery.

As described herein, "a true labor inducing contraction" refers to generally painful, high amplitude uterine electrical activity inducing cervical dilatation, labor, and delivery (despite treatment). Following widely accepted clinical definitions, labor is qualified as preterm labor if the gestational age is less than 37 weeks and as term labor if the gestational age is equal to or greater than 37 weeks.

As used herein, a "physiological parameter" may include: a contraction wave amplitude, a contraction wave frequency over time, a directionality of a contraction wave, a velocity of contraction wave propagation, a contraction wave duration over time, a resting heart rate, a resting heart rate variability, a blood pressure level, a blood glucose level, an oxygen saturation level, a weight, a heart beat of a fetus, a heart rate of a fetus, a heart rate variability of a fetus, a position of a fetus, and a weight of a fetus.

As used herein, a "biological data input" may include: a biological test result, a blood test result, an ultrasound screening result, a vaccination record, proteomics data, genetic data, serum test results, an amniocentesis result, a biomarker result, or any other test, screening, or health history result.

As used herein, a "behavioral parameter" includes: a stress level of the pregnant female, a sleep quality of the pregnant female, an activity level of the pregnant female, a calorie expenditure of the pregnant female, a cardiorespiratory fitness level of the pregnant female, an activity level of a fetus, and a wellbeing of a fetus calculated from one or more physiological parameters.

As used herein, a "lifestyle" of a pregnant female refers to an exercise schedule of the pregnant female, a medical drug use schedule or regimen of the pregnant female, an alcohol consumption metric of the pregnant female, a smoking frequency of the pregnant female, a recreational drug use frequency of the pregnant female, a coitus frequency of the pregnant female, an eating frequency and/or quality of the pregnant female, a traveling frequency of the pregnant female, or any other regular or random activity of the pregnant female.

Uterine Activity Monitoring Systems, Devices, and Methods

As shown in FIG. 1, in various embodiments, a system 10 for uterine activity monitoring includes at least three sensors 12 in electrical communication with a processor 14 and a computer-readable medium (i.e., memory) 16. FIG. 1 illustrates a functional block diagram, and it is to be appreciated that the various functional blocks of the depicted system 10 need not be separate structural elements. For example, in some embodiments, the processor 14 and memory 16 may be embodied in a single chip or two or more chips.

The sensors 12 may sense one or more biopotential signals. In some embodiments, the sensors 12 are configured to measure one or more of: a maternal heart rate, a maternal heart rate variability, a maternal respiration rate, a maternal respiration intensity, a deformation of a belly region of the pregnant woman, a maternal skin or body temperature, a maternal skin conductance (i.e., galvanic skin response), and an electrohysterography (EHG) or electromyography (EMG) signal. In some embodiments, the system comprises at least three sensors. In one non-limiting example, the sensors 12 comprise a measurement electrode and a reference electrode. In some embodiments, the system comprises more than three sensors, for example four, five, six, or seven sensors. In some such embodiments, the sensors 12 include at least one reference electrode and a plurality of measurement electrodes. In one non-limiting embodiment, the sensors 12 may include: an EHG sensor, an electrocardiogram (ECG) sensor, an accelerometer, a gyroscope, an inertial sensor, a piezo-electric sensor, a piezo-resistive sensor, a capacitive sensor, a pressure sensor, and/or a stretch sensor.

The sensors 12 of various embodiments are configured for placement on an outer surface of a woman's body. In some embodiments, the sensors 12 are reusable; in other embodiments, the sensors 12 are disposable. In some embodiments, the sensors 12 are configured for placement over the belly or abdominal region of a pregnant woman. In some embodiments, the sensors 12 form a portion of a sensor module. Various sensor module embodiments are described in more detail below with reference to FIGS. 2-7.

As shown in FIG. 1, a system for uterine activity monitoring includes a processor 14. The processor functions to perform a method of uterine activity monitoring. The processor 14 may be a general purpose microprocessor, a digital signal processor (DSP), a field programmable gate array (FPGA), an application specific integrated circuit (ASIC), or other programmable logic device, or other discrete computer-executable components designed to perform the functions described herein. The processor may also be formed of a combination of computing devices, for example, an analog front-end and a microprocessor, an analog front-end and DSP, a DSP and a microprocessor, an analog front-end, a DSP and a microprocessor, a plurality of microprocessors, one or more microprocessors in conjunction with a DSP core, or any other suitable configuration.

In some embodiments, the processor 14 is coupled, via one or more buses, to the memory 16 in order to read information from, and optionally write information to, the memory 16. The memory 16 may be any suitable computer-readable medium that stores computer-readable instructions for execution by a processor 14. For example, the computer-readable medium may include one or more of RAM, ROM, flash memory, EEPROM, a hard disk drive, a solid state drive, or any other suitable device. In some embodiments, the computer-readable instructions include software stored in a non-transitory format. The software may be programmed into the memory 16 or downloaded as an application onto the memory 16. The software may include instructions for running an operating system and/or one or more programs or applications. When executed by the processor 14, the programs or applications may cause the processor 14 to perform a method of uterine electrical activity monitoring. Some such methods are described in more detail elsewhere herein.

Figure 2:
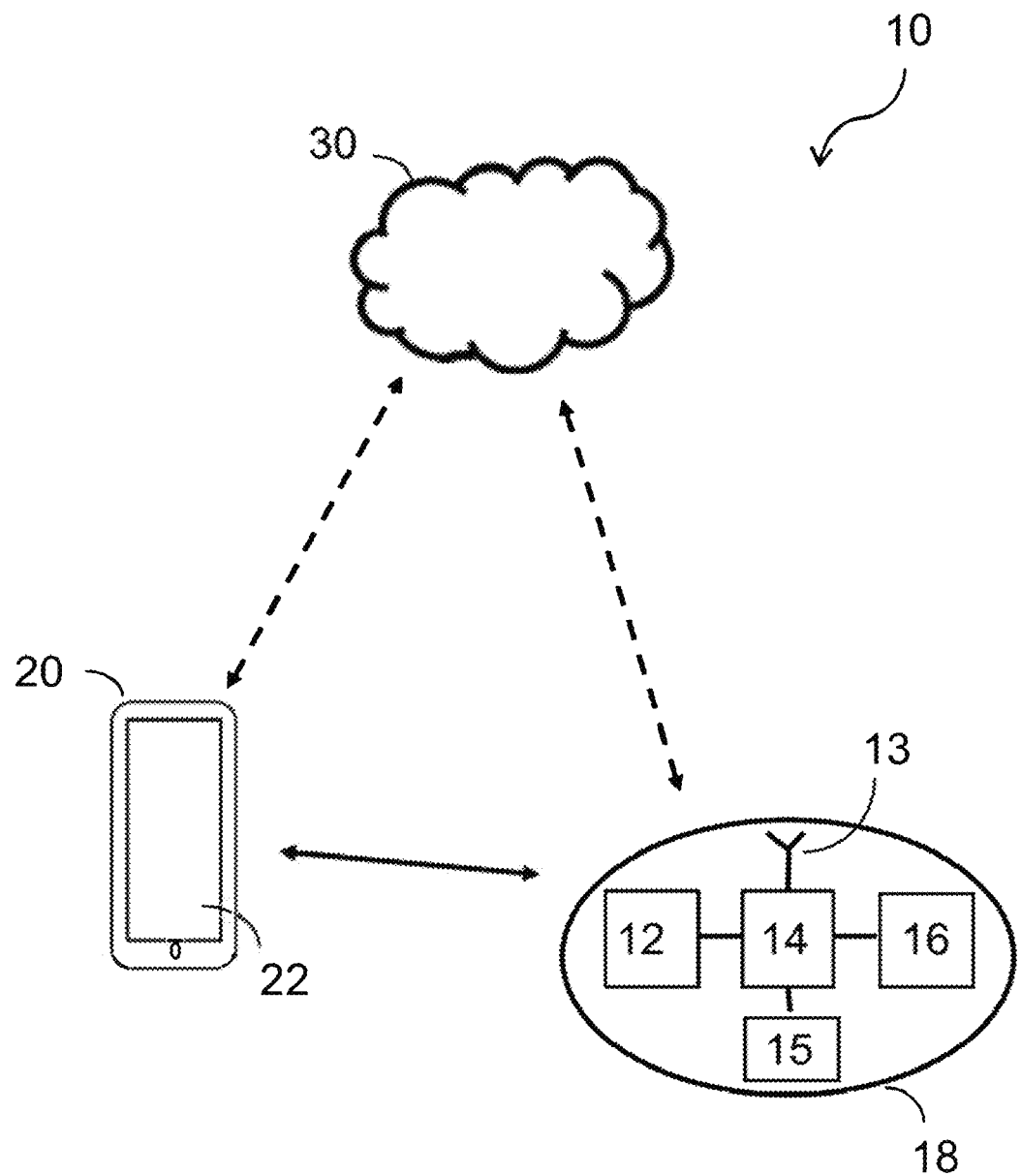
FIG. 2 depicts a schematic of one embodiment of a system for uterine activity monitoring.
Figure 3:
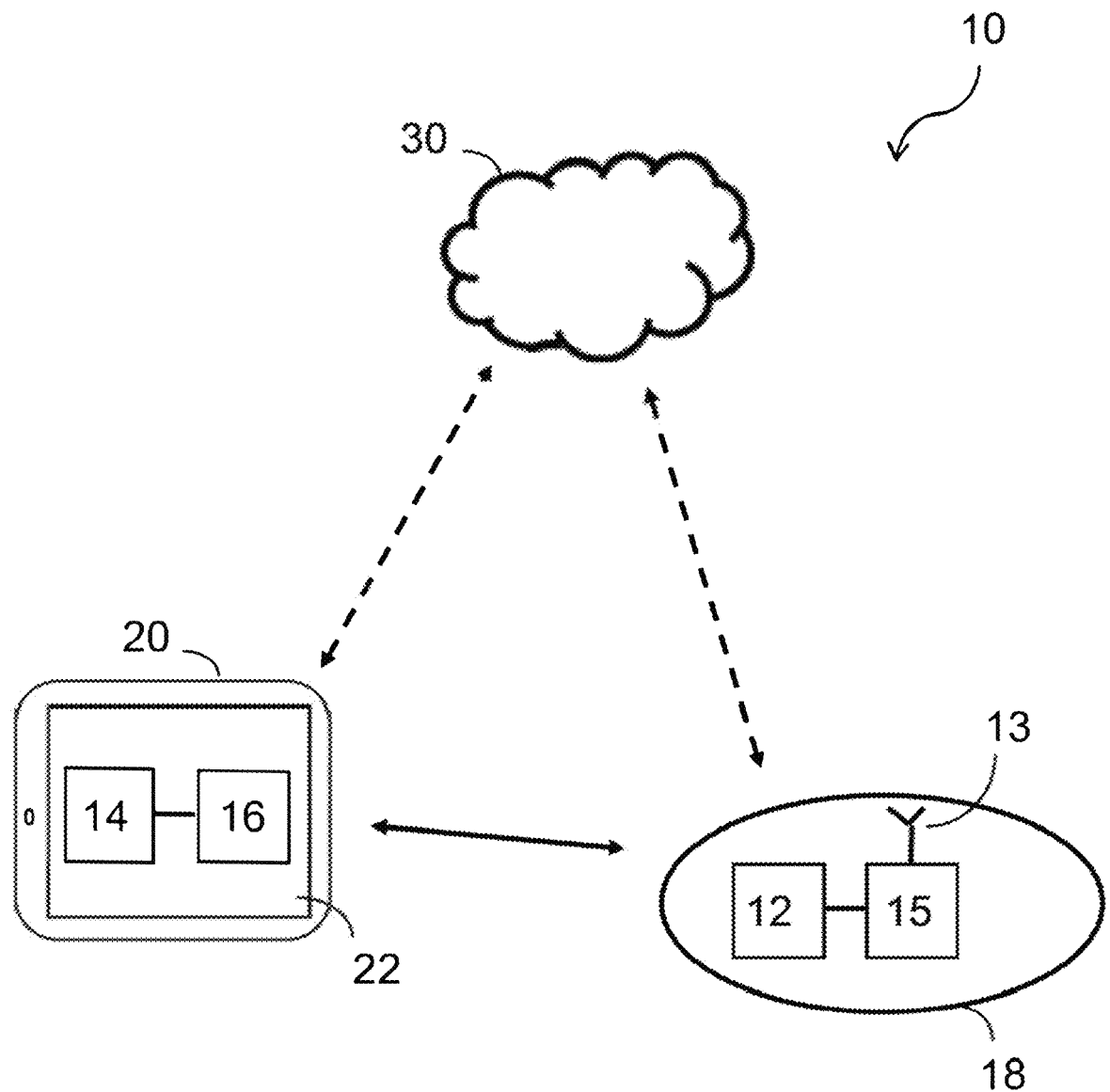
FIG. 3 depicts a schematic of one embodiment of a system for uterine activity monitoring.

As shown in FIG. 2, a system 10 for uterine activity monitoring includes a sensor module 18. In some embodiments, as shown in FIGS. 2-3, the system further includes a computing device 20 having a display 22, and a server 30. In some embodiments, such as the embodiment of FIG. 2, the sensors 12, processor 14, and memory 16 are each positioned on or in the sensor module 18. An electronic circuit 15 and wireless antenna 13 may also be provided on or in the sensor module 18. In such embodiments, signals are: sensed by the sensors 12; amplified, filtered, digitized and/or otherwise processed by the electronic circuit 15; and analyzed by the processor 14. Execution of instructions stored in memory 16 causes the processor 14 on the sensor module 18 to perform one or more of the methods of uterine activity monitoring described elsewhere herein. Analyzed data may be transmitted via the antenna 13 to one or both of the computing device 20 and the server 30 for visual or audio presentation to a user, additional analysis, and/or storage.

In other embodiments, such as the embodiment of FIG. 3, the sensors 12 are positioned on or in the sensor module 18 with the electronic circuit 15 and wireless antenna 13, while a computing device 20 having a display 22 houses the processor 14 that performs a method of uterine activity monitoring and the memory 16 that stores instructions for performing the method. In such embodiments, signals are sensed by the sensors 12 and amplified, filtered, digitized and/or otherwise processed by the electronic circuit 15, and the processed signals are transmitted via the antenna 13 to the computing device 20. The processor 14 of the computing device 20 analyzes the processed signals and determines a type of contraction experienced by the pregnant woman, as described elsewhere herein. The analyzed data may be saved, shared with contacts, or presented to a user via the computing device 20. In some such embodiments, some of or all the analyzed data may be transmitted from the computing device 20 to a server 30 for storage.

In some embodiments, the electronic circuit 15 includes an operational amplifier; a low-pass, high-pass, or band-pass filter; an analog-to-digital (AD) converter; and/or other signal processing circuit components configured to amplify, filter, digitize, and/or otherwise process the signals. The electronic circuit 15 may additionally include a power supply or power storage device, such as a battery or capacitor to provide power to the other electronic components. For example, the electronic circuit 15 may include a rechargeable (e.g., lithium ion) or disposable (e.g., alkaline) battery.

In some embodiments, the antenna 13 includes one or both of a receiver and a transmitter. The receiver receives and demodulates data received over a communication network. The transmitter prepares data according to one or more network standards and transmits data over a communication network. In some embodiments, a transceiver antenna 13 acts as both a receiver and a transmitter for bi-directional wireless communication. As an addition or alternative to the antenna 13, in some embodiments, a databus is provided within the sensor module 18 so that data can be sent from, or received by, the sensor module 18 via a wired connection.

In some embodiments, there is one-way or two-way communication between the sensor module 18 and the computing device 20, the sensor module 18 and the server 30, and/or the computing device 20 and the server 30. The sensor module 18, computing device 20, and/or server 30 may communicate wirelessly using Bluetooth, low energy Bluetooth, near-field communication, infrared, WLAN, Wi-Fi, CDMA, LTE, other cellular protocol, other radiofrequency, or another wireless protocol. Additionally or alternatively, sending or transmitting information between the sensor module 18, the computing device 20, and the server 30 may occur via a wired connection such as IEEE 1394, Thunderbolt, Lightning, DVI, HDMI, Serial, Universal Serial Bus, Parallel, Ethernet, Coaxial, VGA, or PS/2.

In some embodiments, the computing device 20 is a computational device wrapped in a chassis that includes a visual display with or without touch responsive capabilities (e.g., Thin Film Transistor liquid crystal display (LCD), in-place switching LCD, resistive touchscreen LCD, capacitive touchscreen LCD, organic light emitting diode (LED), Active-Matrix organic LED (AMOLED), Super AMOLED, Retina display, Haptic/Tactile touchscreen, or Gorilla Glass), an audio output (e.g., speakers), a central processing unit (e.g., processor or microprocessor), internal storage (e.g., flash drive), n number of components (e.g., specialized chips and/or sensors), and n number of radios (e.g., WLAN, LTE, WiFi, Bluetooth, GPS, etc.). In some embodiments, the computing device 20 is a mobile or portable computing device, such as a mobile phone, smartphone, smart watch, smart glasses, smart contact lenses, or other wearable computing device, tablet, laptop, netbook, notebook, or any other type of mobile computing device. In some embodiments, the computing device 20 is a stationary computing device, such as a desktop computer or workstation.

In some embodiments, the server 30 is a database server, application server, internet server, or other remote server. In some embodiments, the server 30 may store user profile data, historical user data, historical community data, algorithms, machine learning models, software updates, or other data. The server 30 may share this data with the computing device 20 or the sensor module 18, and the server 30 may receive newly acquired user data from the sensor module 18 and/or the computing device 20.

Figure 4:
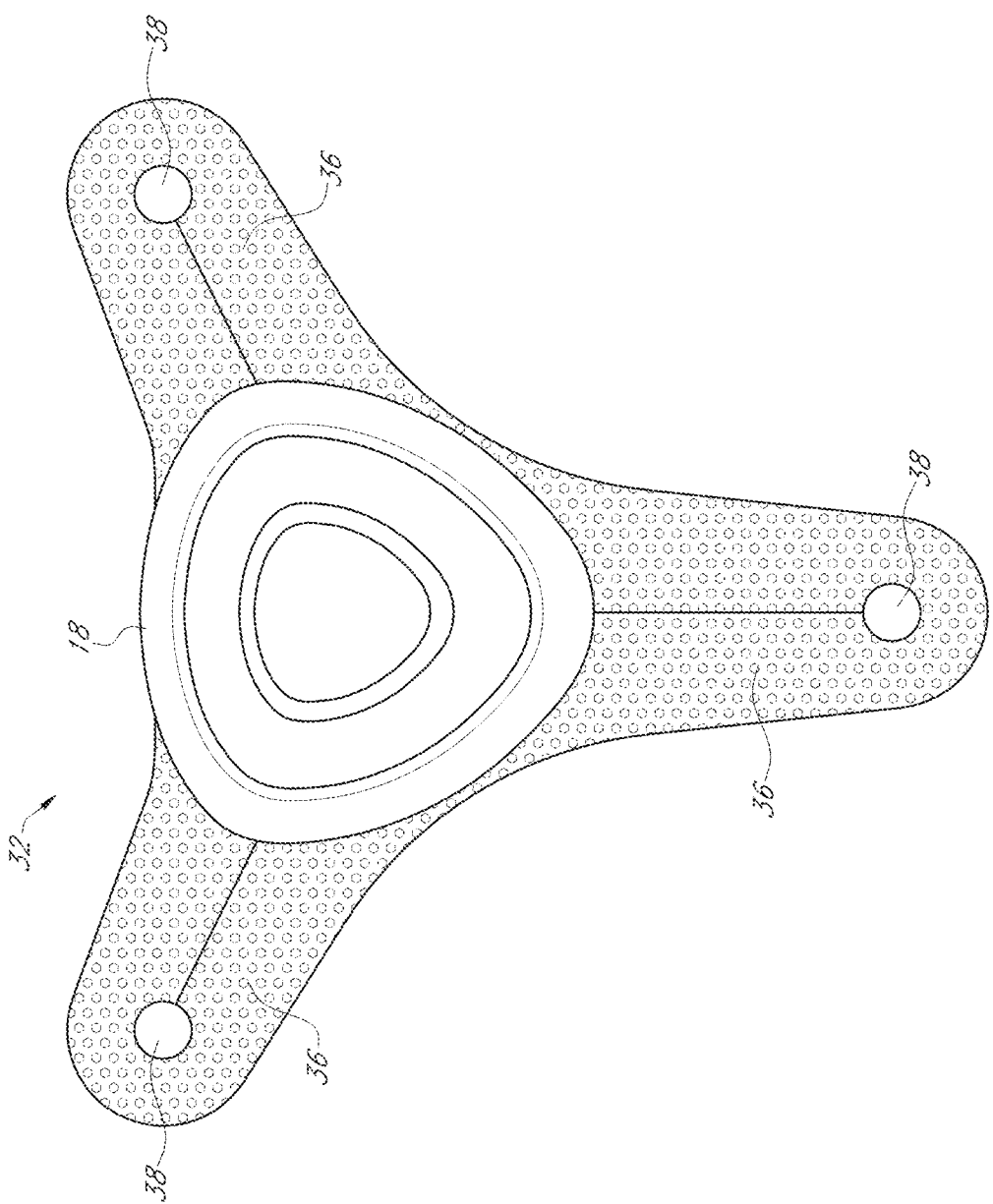
FIG. 4 depicts a top view of one embodiment of a sensor module coupled to a belly patch.

A few non-limiting examples of sensor modules 18 are depicted in FIGS. 4-7. By comparing the sensor modules of FIGS. 4-7, one can easily understand that the sensor module 18 can take many different form factors. In one embodiment, as shown in FIG. 4, the sensor module 18 of various embodiments has many different shapes, sizes, colors, materials, and levels of conformability to the body. The sensor module 18 may connect to, be embedded within, or form a portion of: a patch 32 (e.g., FIGS. 4-6); a strap, belt, or band 34 (e.g., FIG. 7); a blanket/cover; t-shirt; pants; underwear; or other article of clothing or wearable accessory. In some embodiments, the device is attached to the body using an adhesive layer. In another embodiment, the adhesive layer can be replaced by the user. In another exemplary embodiment, the device can be attached to the body using a strap or a piece of textile that can maintain the device in contact with the body.

Figure 5:
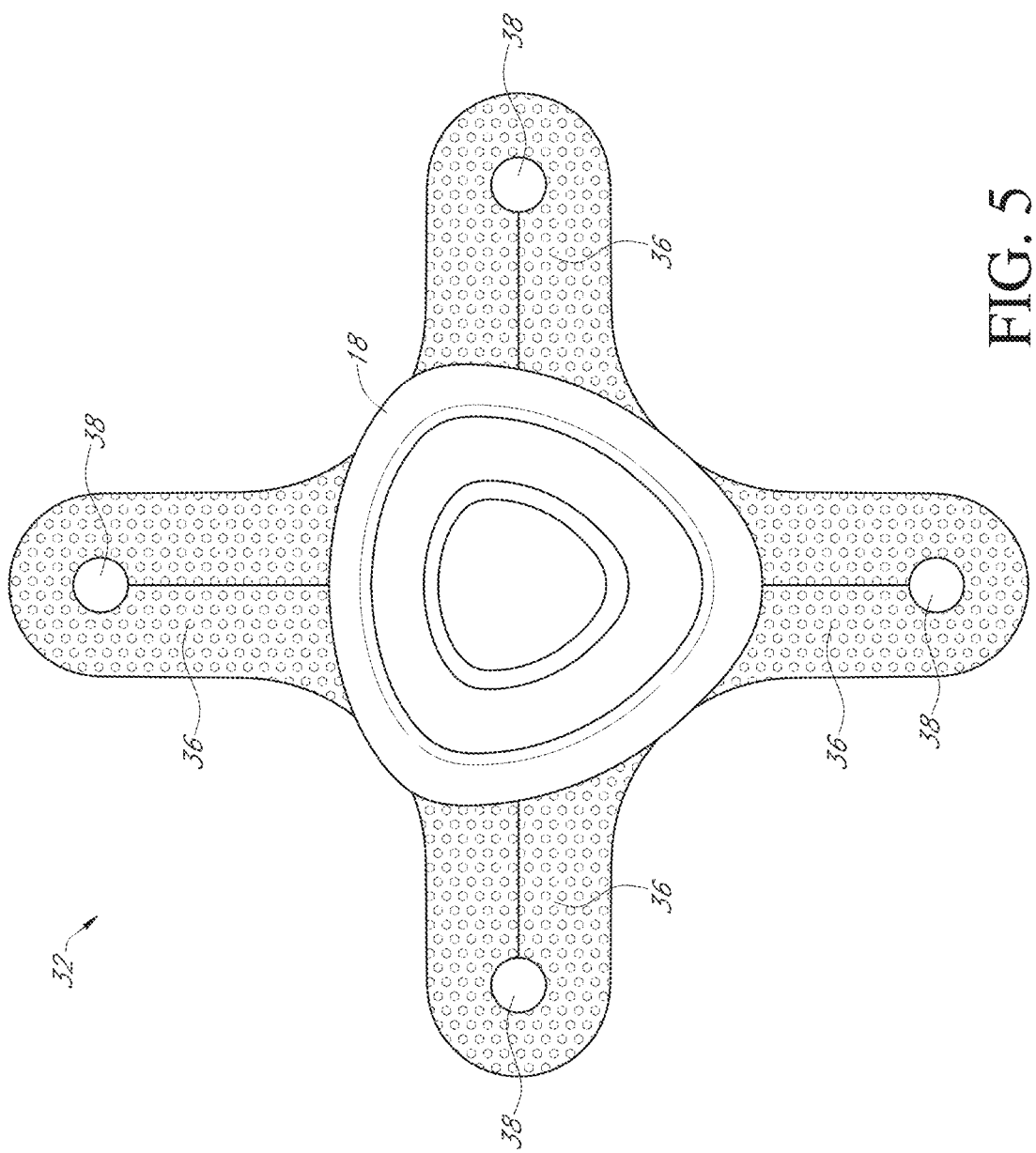
FIG. 5 depicts a top view of one embodiment of a sensor module coupled to a belly patch.
Figure 6:
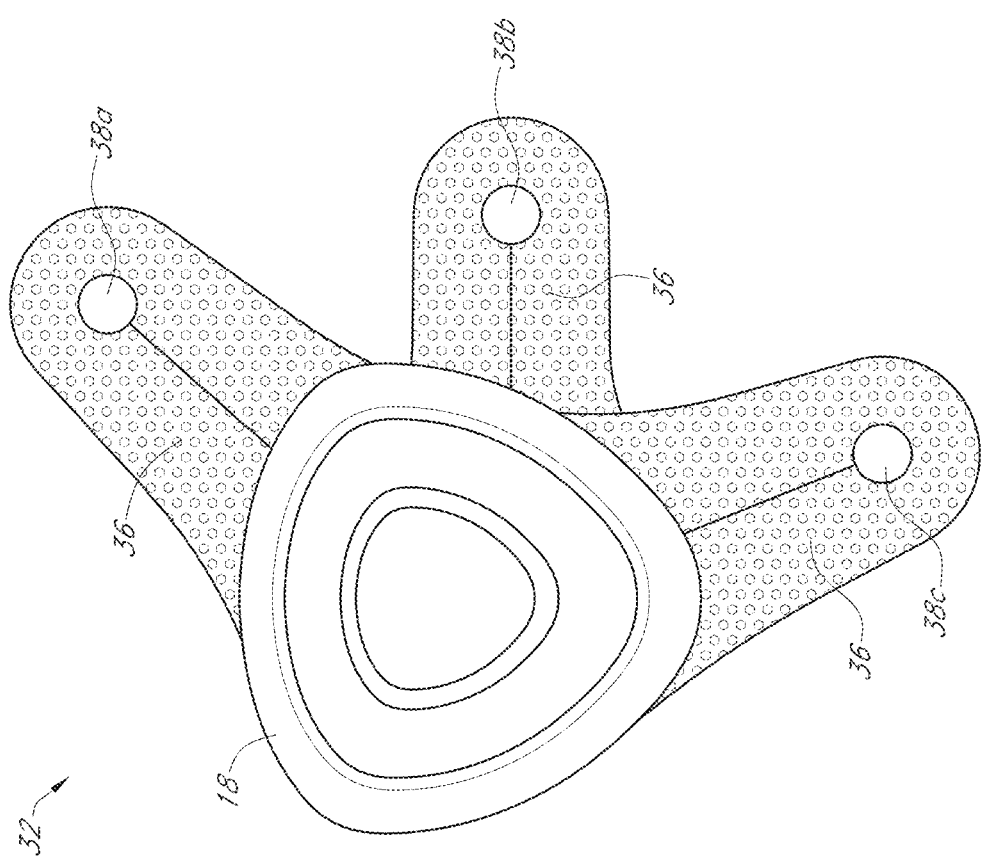
FIG. 6 depicts a top view of one embodiment of a sensor module coupled to a belly patch.
Figure 7:
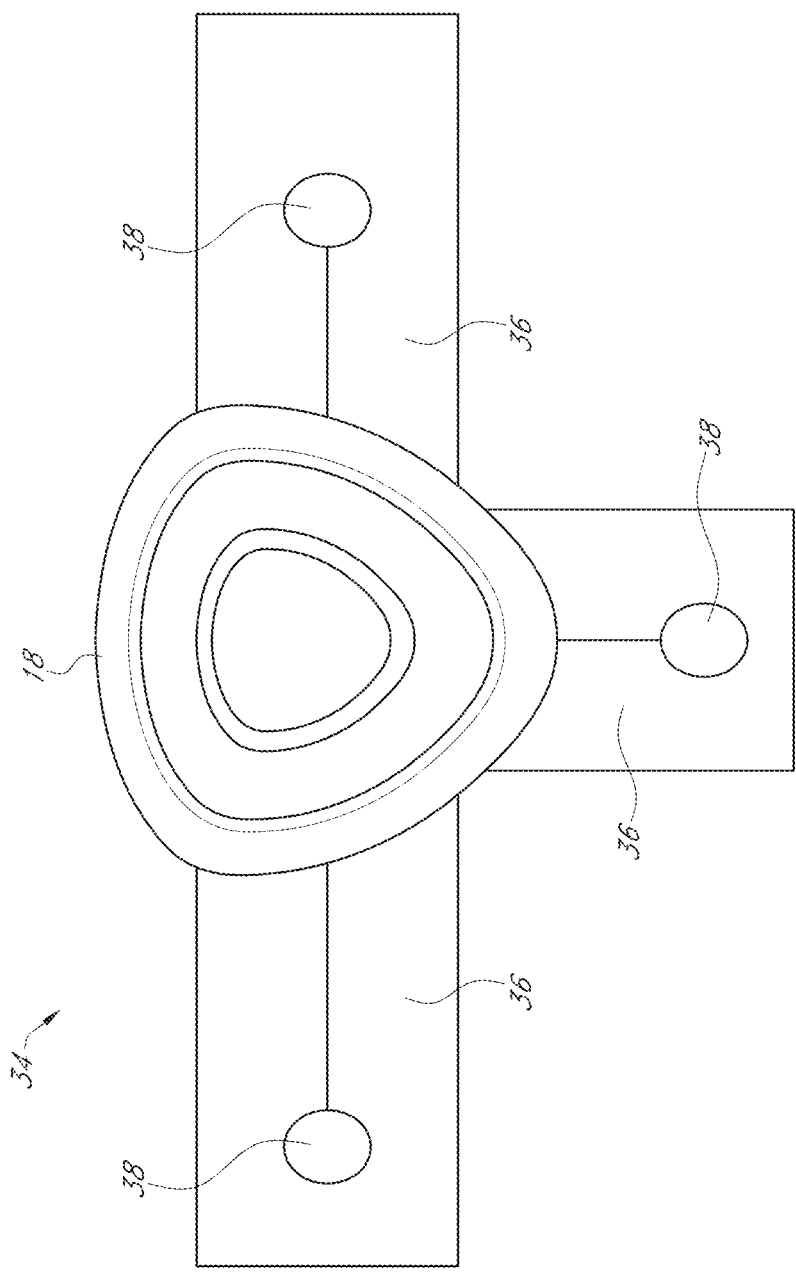
FIG. 7 depicts a top view of one embodiment of a sensor module coupled to a belly belt.

The sensor module 18 may detect uterine electrical activity, maternal heart electrical activity, maternal respiration activity, maternal skin conductance, maternal skin or body temperature, and/or maternal belly deformation using two, three, four, or a plurality of sensors 38 electrically connected to the sensor module 18 via electrical contacts 36, as shown in FIGS. 4-7. In some embodiments, patch 32 has extremities or lobes, each including an electrical contact 36; in other embodiments, additional sensors are disposed throughout a middle section of the electrode patch 32. In some embodiments, the electrical contacts 36 may be substantially distributed around a perimeter of the sensor module 18, for example as shown in FIG. 5. In other embodiments, the electrical contacts 36 may be extending substantially from one side of the sensor module, for example as shown in FIG. 6. The patch 32 and the sensor module 18 may be in one part or may be made of two separate parts. The two separate parts can be provided with a mechanical and electrical system for attaching one to the other, such as a clipping system or a magnet.

Figure 9:
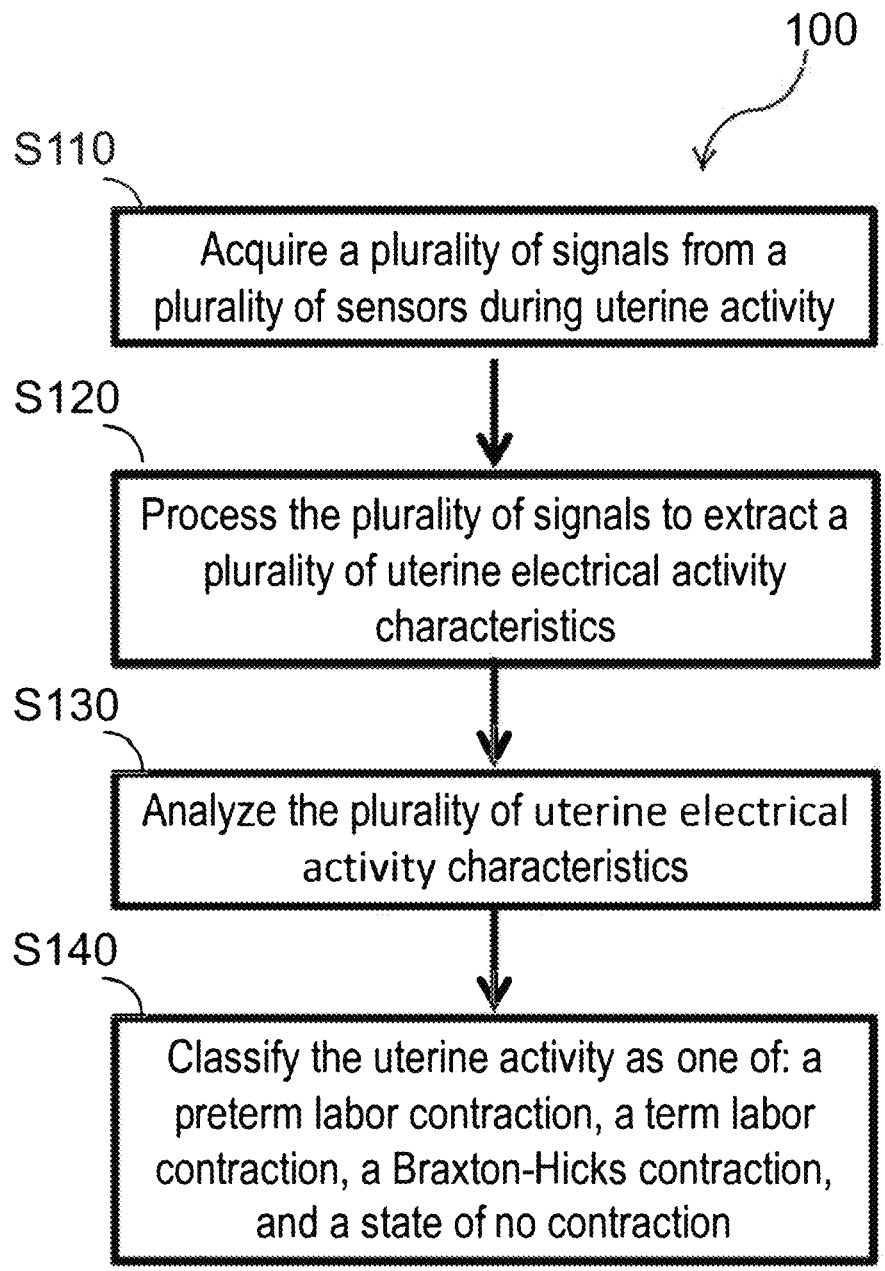
FIG. 9 depicts a flow chart of one embodiment of a method of uterine activity monitoring.

As shown in FIG. 9, one embodiment of a method 100 for uterine activity monitoring includes acquiring a plurality of signals from a plurality of sensors during uterine activity in block S110, processing the plurality of signals to extract a plurality of uterine electrical activity characteristics in block S120, analyzing the plurality of uterine electrical activity characteristics of the uterine activity in block S130, and classifying the uterine activity as one of: a preterm labor contraction, a term labor contraction, a Braxton-Hicks contraction, and a state of no contraction S140. The method 100 functions to detect and analyze uterine activity to determine a type of contraction or identify a state of no contraction. In some embodiments, the method 100 functions to notify or alert a user to the detected uterine activity or to the classification of the detected uterine activity.

As shown in FIG. 9, one embodiment of a method 100 for uterine activity monitoring includes block S110, which recites acquiring a plurality of signals from a plurality of sensors during uterine activity. In some embodiments, block S110 functions to detect uterine electromyogram (EMG) or electrohysterography (EHG) signals, ECG signals, heart rate (HR) signals, heart rate variability (HRV) signals, respiration signals, belly deformation or movement signals, temperature signals, and/or galvanic skin response signals instantaneously or over time. In some embodiments, the plurality of signals is collected from three or more regions of the belly of the pregnant woman. For example, as shown in FIG. 6, a first sensor 38a may be positioned near a fundus of the uterus, a second sensor 38b near a cervix of the user, and a third 38c on a right or left side of the belly region. However, any sensor configuration may be used to measure uterine activity, as shown in FIGS. 4-7. Additionally or alternatively, in some embodiments, one or more additional signals (e.g., heart rate, heart rate variability, activity, stress level, etc.) are collected from another location on the pregnant woman (e.g., wrist, chest, etc.), as described in co-pending U.S. patent application Ser. No. 15/200,500 to Bloom Technologies NV, the disclosure of which is herein incorporated by reference in its entirety.

As shown in FIG. 9, one embodiment of a method 100 for uterine activity monitoring includes block S120, which recites processing the plurality of signals to extract a plurality of uterine electrical activity characteristics. Block 120 functions to amplify, filter, digitize, and/or process a plurality of signals collected with the plurality of sensors to determine a plurality of characteristics, features, or parameters of uterine activity. In some embodiments, block S120 processes uterine electrical activity signals, uterine electromyography signals, or uterine electrohysterography signals. The plurality of uterine electrical activity characteristics may include at least two of: a uterine electrical activity frequency, a uterine electrical activity amplitude over time, a uterine electrical activity duration over time, a directionality of uterine electrical activity, and a velocity of uterine electrical activity. The directionality and/or velocity of uterine electrical activity is determined by sensing a uterine electrical activity movement or propagation over time between at least two sensors, for example as shown in FIGS. 8A-8B.

Figure 8A:
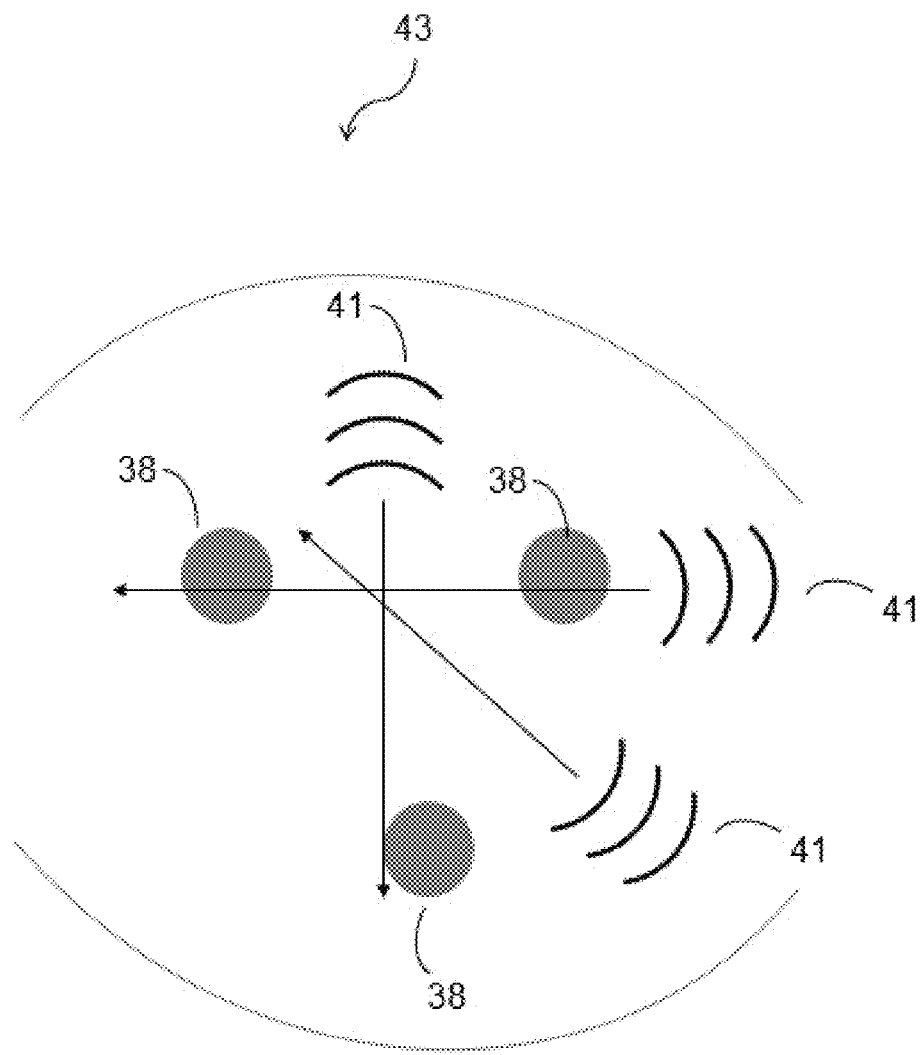
FIG. 8A schematically depicts a method of detecting a plurality of sequential or concomitant uterine electrical activities using a system for uterine activity monitoring.
Figure 8B:
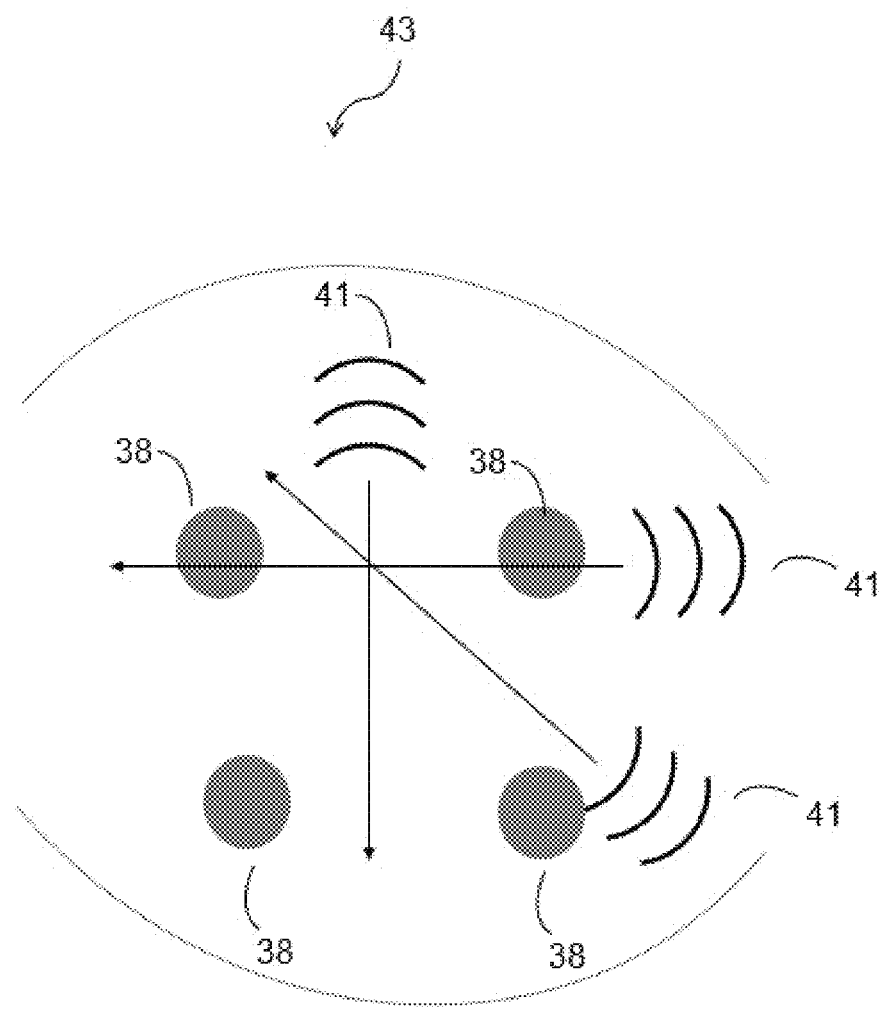
FIG. 8B schematically depicts a method of detecting a plurality of sequential or concomitant uterine electrical activities using a system for uterine activity monitoring.

As shown in FIGS. 8A-8B, an abdominal region 43 of a pregnant woman is depicted with a plurality of sensors 38 positioned thereon. A direction and/or velocity (indicated by arrows) of uterine electrical activity 41 can be detected as it passes through at least a subset of the sensors 38. In such embodiments, each sensor 38 has a defined position or orientation relative to the other sensors 38, such that the processor determines which sensor(s) a uterine electrical activity is contacting at each point in time. In some embodiments, as a uterine electrical activity 41 passes between or over at least two sensors 38, a direction or velocity of the uterine electrical activity can be discerned. In some embodiments, as a uterine electrical activity 41 passes between or over at least three sensors 38, a direction and velocity of the uterine electrical activity 41 can be detected.

In some embodiments, the plurality of signals is further processed to extract a deformation of the belly region of the pregnant female. In some such embodiments, the deformation may be measured by an inertial sensor (e.g., a gyroscope, an accelerometer), a piezo-electric sensor, a piezo-resistive sensor, a capacitive sensor, a pressure sensor, or a stretch sensor. In one non-limiting example, as uterine electrical activity moves from the top of the belly (e.g., fundus region) to the bottom of the belly (e.g., cervix region), the belly may temporarily deform at the location or position of the uterine electrical activity as the uterine electrical activity propagates. Such deformation may be detected and measured by an inertial sensor and correlated with additional uterine electrical activity characteristics (e.g., frequency, amplitude, etc.).

In some embodiments, the method includes processing the plurality of signals to extract a maternal characteristic, for example a heart electrical activity, a belly movement activity, and/or an autonomic nervous system response (e.g., variability of heart electrical activity, respiration activity, a maternal galvanic skin response, a maternal skin or body temperature, etc.). In such embodiments, the maternal characteristic may include an RR interval duration; an RR interval frequency; a mean electrical axis; a belly region starting location or position; a belly region ending location or position; an acceleration of a belly region; a body or skin temperature before, during, or after the uterine activity; a degree of skin conductance before, during, or after the uterine activity; or any other characteristics.

As shown in FIG. 9, one embodiment of a method 100 for uterine activity monitoring includes block S130, which recites analyzing the plurality of uterine electrical activity characteristics. Block S130 functions to interpret the sensor data and provide meaningful information about uterine activity to a user of the system. In some embodiments, analyzing comprises using machine learning techniques. In some such embodiments, machine learning techniques include pattern recognition, classification, support vector machines, random forest, hierarchical model, artificial neural networks, Bayesian statistics, or any other machine learning technique. In some embodiments, analyzing comprises using thresholding or regression model algorithms. In some embodiments, analyzing comprises comparing two or more uterine electrical activity characteristics, at least one uterine electrical activity characteristic and at least one maternal characteristic, or at least one uterine electrical activity characteristic and a deformation of a belly region to identify a pattern; a relative increase; a relative decrease; a deviation from a baseline, historical data, community data, a previous position or detected sensor signal, etc.; or any other parameter. In some embodiments, analyzing comprises combining two or more uterine electrical activity characteristics to determine a type of uterine activity.

As shown in FIG. 9, one embodiment of a method 100 for uterine activity monitoring includes block S140, which recites classifying the uterine activity as one of: a preterm labor contraction, a term labor contraction, a Braxton-Hicks contraction, and a state of no contraction. In one non-limiting example, distinguishing a Braxton-Hicks contraction from a term labor contraction may include determining a direction of uterine electrical activity (e.g., disorganized for Braxton-Hicks and top to bottom for true labor), a uterine electrical activity amplitude (e.g., small amplitude for Braxton-Hicks and large amplitude for true labor), and a uterine electrical activity energy density spectrum (e.g. skewed towards low frequencies for Braxton-Hicks, and towards higher frequencies for labor contractions), and a uterine electrical activity regularity (e.g., non regular for Braxton-Hicks and regular for term labor).

In some embodiments, classifying includes comparing the detected, processed, and analyzed uterine activity to a look-up table; historical or community-derived data; literature or published data; personal data from the user; or any other type of data source to determine a type of contraction or a state of no contraction.

Figure 10:
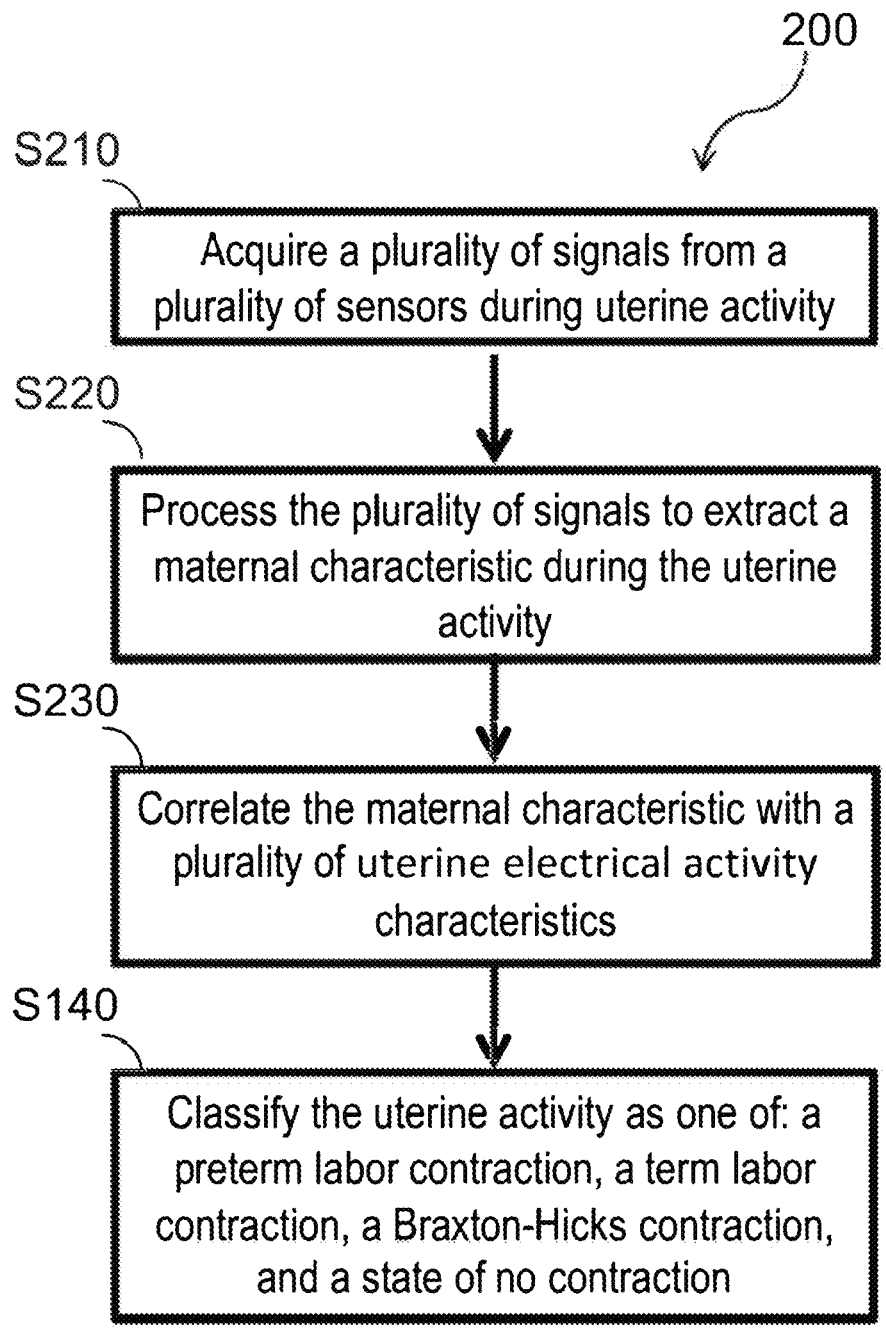
FIG. 10 depicts a flow chart of one embodiment of a method of uterine activity monitoring.

In some embodiments, as shown in FIG. 10, a method 200 for uterine activity monitoring includes: acquiring a plurality of signals from a plurality of sensors during uterine activity S210; processing the plurality of signals to extract a maternal characteristic during the uterine activity S220; correlating the maternal characteristic with a plurality of uterine electrical activity characteristics S230; and classifying the uterine activity as one of: preterm labor contractions, a term labor contraction, a Braxton-Hicks contraction, and a state of no contraction S240.

In some embodiments, as shown in FIG. 10, one embodiment of a method 200 for uterine monitoring includes block S220, which recites processing the plurality of signals to extract a maternal characteristic during the uterine activity. Block S220 functions to measure maternal respiration activity, maternal heart activity, maternal stress responses, and/or maternal autonomic nervous system responses during uterine activity. In some embodiments, a maternal characteristic includes one or more of: a maternal heart rate, a maternal heart rate variability, a maternal respiration rate, a maternal respiration intensity, a maternal galvanic skin response, and/or a maternal skin or body temperature.

In some embodiments, as shown in FIG. 10, one embodiment of a method 200 for uterine activity monitoring includes block S230, which recites correlating the maternal characteristic with the plurality of uterine electrical activity characteristics. The maternal pain response is intimately tied to contraction type and strength. Labor contractions often result in changes in responses controlled by the maternal autonomic nervous system, for example heart rate, heart rate variability, respiration rate, respiration intensity, galvanic skin responses, and/or body or skin temperature. Block S230 functions to compare, combine, or correlate maternal characteristics with uterine electrical activity to more accurately determine a type of contraction or to identify a state of no contraction. In one non-limiting example, distinguishing a Braxton-Hicks contraction from a term labor contraction may include determining a uterine electrical activity amplitude (e.g, small amplitude for Braxton-Hicks and large amplitude for term labor), a uterine electrical activity frequency (e.g., low frequency for Braxton-Hicks and high frequency for term labor), and a maternal heart rate (e.g., slower heart rate for Braxton-Hicks and faster heart rate for term labor). However, in some cases, female heart rate does not significantly respond to pain. In such embodiments, as a non-limiting example, distinguishing Braxton-Hicks from term labor contractions may include determining a uterine electrical activity amplitude (e.g, small amplitude for Braxton-Hicks and large amplitude for term labor), a uterine electrical activity frequency (e.g., low frequency for Braxton-Hicks and high frequency for term labor), and a maternal respiration rate or intensity (e.g., slower respiration rate/intensity for Braxton-Hicks and faster respiration rate/intensity for term labor).

In some embodiments, the method may include analyzing the plurality of uterine electrical activity characteristics over time to identify one or more changes; and correlating the maternal characteristic with the one or more changes in the plurality of uterine electrical activity characteristics. Contractions are characterized by periods of intense uterine electrical activity followed by periods of less uterine electrical activity. Monitoring how the uterine electrical activity changes over time may improve a determination of contraction type. Further, maternal characteristics, such as respiration rate and heart rate, may have periods of intensity followed by periods of slower, less-intense responses, for example tracking with one or more bursts in uterine electrical activity. Aligning these periods of intensity and reduced activity or determining if the periods can be aligned may improve a determination of contraction type. In some embodiments, the plurality of maternal characteristics additionally or alternatively is monitored over time and correlated to the plurality of uterine electrical activity characteristics.

In some embodiments, the method includes analyzing the plurality of uterine electrical activity characteristics over time to identify one or more changes; and correlating the deformation of the belly region with one or more changes in the plurality of uterine electrical activity characteristics. In one non-limiting example, a uterine electrical activity frequency, amplitude, direction of propagation, and/or velocity may be correlated with deformation of a belly region, such that the belly deforms as the uterine electrical activity propagates from a first belly region to a second belly region.

In some embodiments, the method includes generating an alert or notifying a user of the uterine activity. An alert or notification may include an SMS, pop-up, push notification, email, or another type of message displayable on a sensor module or computing device communicatively coupled to the system. In some embodiments, an alert or notification includes an audio (e.g., spoken notification, buzz, beep, a type of music depending on contraction, etc.), visual (e.g., text, picture, video, etc.), or haptic (e.g., vibration changing in frequency or intensity based on contraction types, vibrating during each sensed uterine electrical activity, etc.) notification. In some embodiments, the alert or notification is sent to the user wearing the system. Alternatively, the alert or notification may be sent to another user (other than the pregnant female) of the system, for example a healthcare provider, service provider, family member, friend, doula, partner, etc.

In some embodiments, the method includes displaying on a computing device communicatively coupled to the processor an alert, notification, or visual representation of the uterine activity or a series of uterine activities or a classification of the uterine activity (e.g., preterm labor contraction, true labor contraction, Braxton-Hicks contraction, no contraction). In some embodiments, a user may interact with the alert, notification, or visual representation to input additional information into the system (e.g., emotions; feelings of stress, anxiety, nausea, etc.); dismiss the alert, notification, or visual representation; forward the alert, notification, or visual representation to another user; contact another user; or any other use case.

In some embodiments, the method includes recommending a course of action to the user based on the detected or classified uterine activity. Non-limiting examples of recommendations include: take a warm bath or shower (e.g., to slow labor), perform light exercise (e.g., to progress labor), relax (e.g., to reduce Braxton-Hicks contractions), drink water (e.g., to improve hydration and reduce Braxton-Hicks contractions), eat spicy foods (e.g., to improve labor induction), contact a healthcare provider, go to a hospital, do breathing exercises, etc.

In some embodiments, the method includes determining a probability that the pregnant female is experiencing one of: preterm labor contractions, term labor contractions, Braxton-Hicks contractions, and no contractions, and determining a degree of certainty around the determined probability. In some such embodiments, the method performed by the processor further includes calculating the relevant statistics, such as the probability that the woman is experiencing a certain type of uterine activity, the degree of certainty around the determined probability, and the probability that the type of uterine activity will lead to labor.

Figure 11:
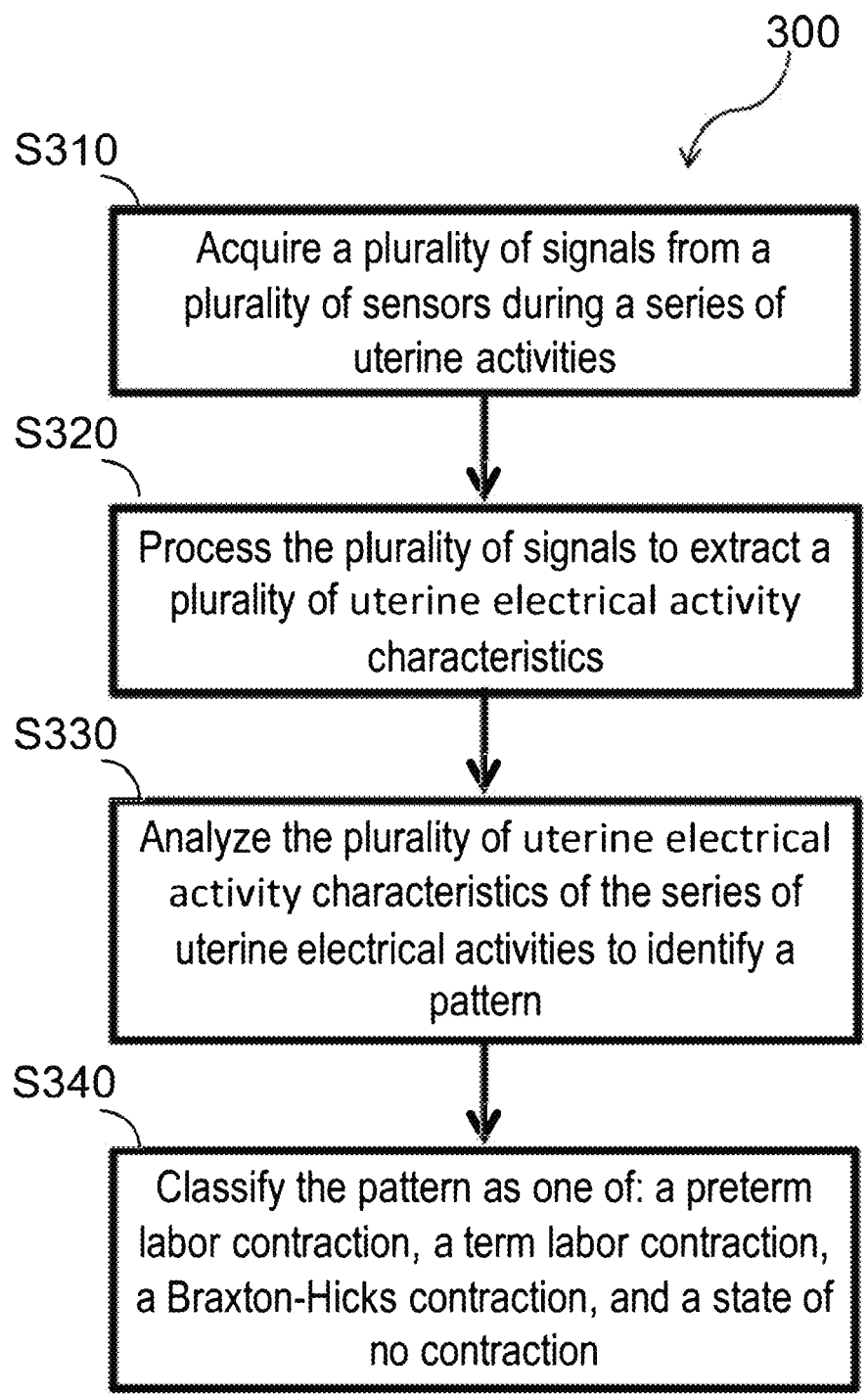
FIG. 11 depicts a flow chart of one embodiment of a method of monitoring a series of uterine activities.

As shown in FIG. 11, one embodiment of a method 300 for uterine activity monitoring includes: acquiring a plurality of signals from a plurality of sensors during a series of uterine activities S310; processing the plurality of signals to extract a plurality of uterine electrical activity characteristics of the series of uterine activities S320; analyzing the plurality of uterine electrical activity characteristics of the series of uterine activities to identify a pattern S330; and classifying the pattern as one of: a preterm labor contraction, a term labor contraction, a Braxton-Hicks contraction, and a state of no contraction S340. The method 300 functions to assess a series of uterine activities to detect a pattern and determine if the pattern is indicative of a type of contraction or labor.

As shown in FIG. 11, one embodiment of a method 300 for uterine activity monitoring includes block S310, which recites acquiring a plurality of signals from a plurality of sensors during a series of uterine activities. Block S310 functions to acquire signals associated with uterine activity over time to detect any patterns in the uterine activity. In some embodiments, the plurality of signals is acquired over ten minutes, twenty minutes, thirty minutes, sixty minutes, two hours, five hours, twelve hours, eighteen hours, twenty-four hours, or any other suitable time period. In some embodiments, the series of uterine activities are stochastic, random, organized, or regular.

As shown in FIG. 11, one embodiment of a method 300 for uterine activity monitoring includes block S320, which recites processing the plurality of signals to extract a plurality of uterine electrical activity characteristics of the series of uterine activities. Block S320 functions to amplify, filter, digitize, or otherwise process the plurality of signals to extract meaningful features or characteristics of uterine electrical activity which may be indicative of a type of contraction. The pattern of the plurality of uterine electrical activity characteristics may include at least one of: a time interval between uterine electrical activities, a change in uterine electrical activity frequency, a change in uterine electrical activity amplitude, a change in uterine electrical activity duration, a change in uterine electrical activity directionality, and a change in uterine electrical activity velocity.

As shown in FIG. 11, one embodiment of a method 300 for uterine activity monitoring includes block S330, which recites analyzing the plurality of uterine electrical activity characteristics of the series of uterine activities to identify a pattern. Block S330 functions to track or monitor uterine activity over time to identify patterns that may indicate a type of contraction. Non-limiting example of patterns include: a series of uterine electrical activities separated by substantially consistent time periods; a series of uterine electrical activities of substantially similar frequency, amplitude, velocity, or propagating in a substantially similar direction; a series of uterine electrical activities substantially aligned or coordinated with a maternal heart rate, maternal heart rate variability, maternal respiration rate, maternal respiration intensity, maternal skin conductance, maternal body or skin temperature, or belly deformation; a change in a maternal characteristic; etc.

As shown in FIG. 11, one embodiment of a method 300 for uterine activity monitoring includes block S340, which recites classifying the pattern as one of: a preterm labor contraction, a term labor contraction, a Braxton-Hicks contraction, and a state of no contraction. In some embodiments, classifying includes automatically comparing the series of uterine activities to a look-up table; historical or community-derived data; literature or published data; personal data from the user; or any other type of data source to determine a type of contraction or identify a state of no contraction.

Figure 12:
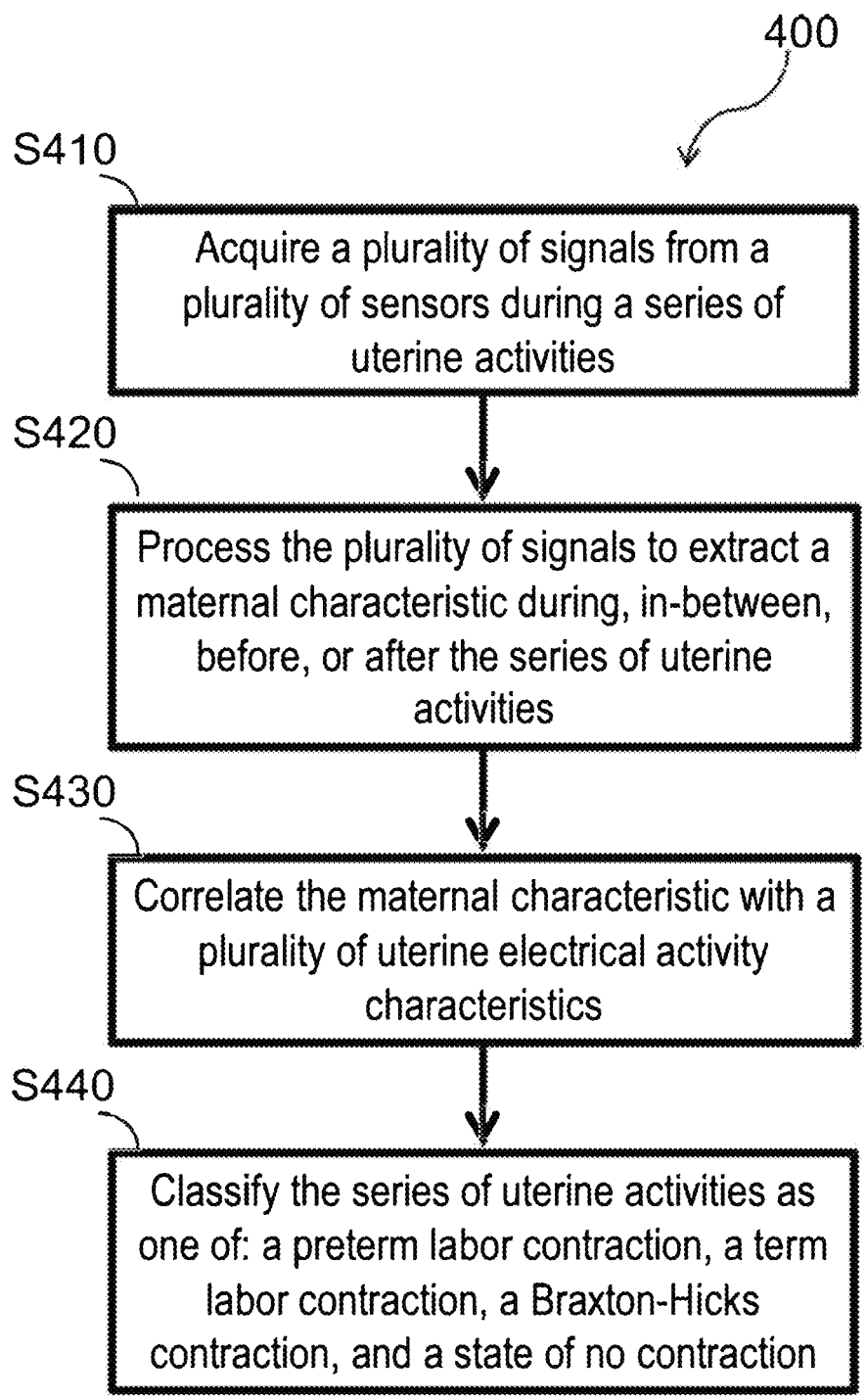
FIG. 12 depicts a flow chart of one embodiment of a method of monitoring a series of uterine activities.

In some embodiments, as shown in FIG. 12, one embodiment of a method 400 of uterine activity monitoring includes acquiring a plurality of signals from a plurality of sensors during a series of uterine activities S410; processing the plurality of signals to extract a maternal characteristic during, in-between, before, or after the series of uterine activities S420; correlating the maternal characteristic with a plurality of uterine electrical activity characteristics S430; and classifying the series of uterine activities as one of: a preterm labor contraction, a term labor contraction, a Braxton-Hicks contraction, and a state of no contraction S440.

In some embodiments of block S420, a change in maternal heart rate, maternal heart rate variability, maternal respiration rate, maternal respiration intensity, maternal skin conductance, maternal body or skin temperature, and/or deformation of a belly region occurs before, during, in between, or after uterine activities. In some such embodiments, the method monitors maternal characteristics over time to align, compare, or correlate maternal characteristics with uterine electrical activity or a series of uterine electrical activities to determine a type of contraction.

Pre-Term Birth Risk Systems, Devices, and Methods

Figure 13:
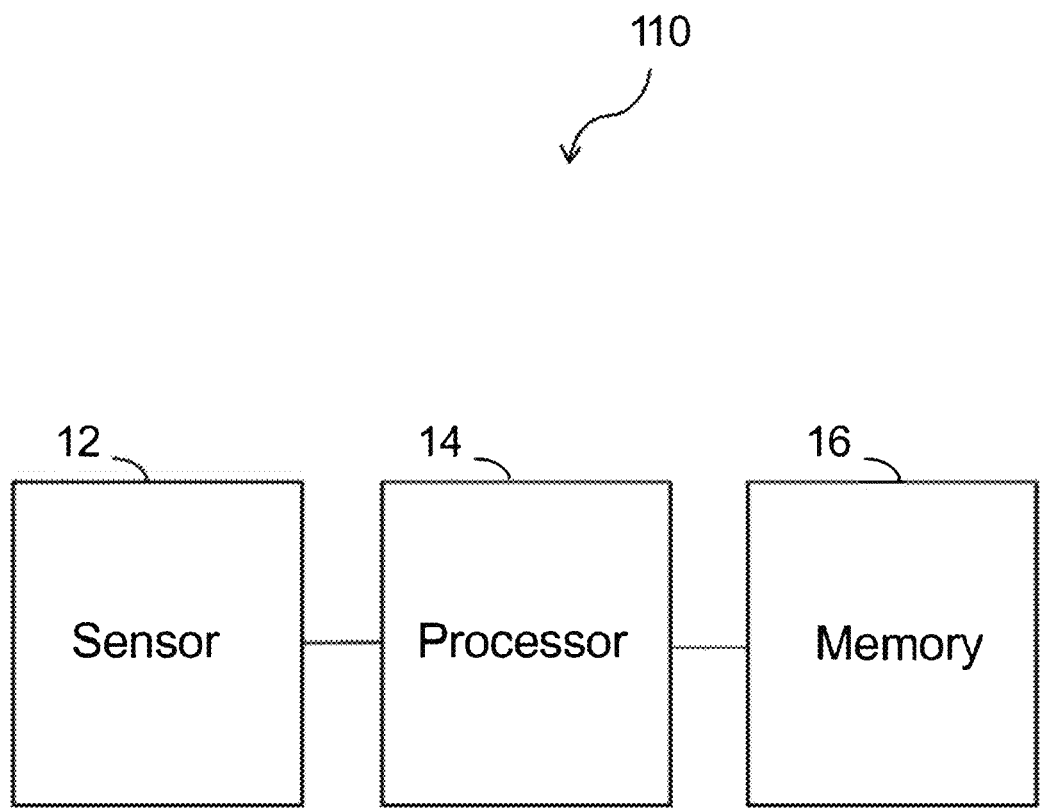
FIG. 13 illustrates a schematic block diagram of one embodiment of a system for assessing pre-term birth risk.

FIG. 13 shows a functional block diagram of one embodiment of a system 110 for assessing pre-term birth risk. The system 110 functions to acquire one or more inputs (e.g., user input, sensor input, biological data input, etc.) and determine a baseline pre-term birth risk factor and/or an instant pre-term birth risk factor. The system 110 includes a sensor 12, a processor 14, and memory 16. Although each component is depicted as a separate element, it may be appreciated by one of skill in the relevant art that each component may not be a separate structural element, for example the processor 14 and memory 16 may reside on one chip or two or more chips.

Figure 14:
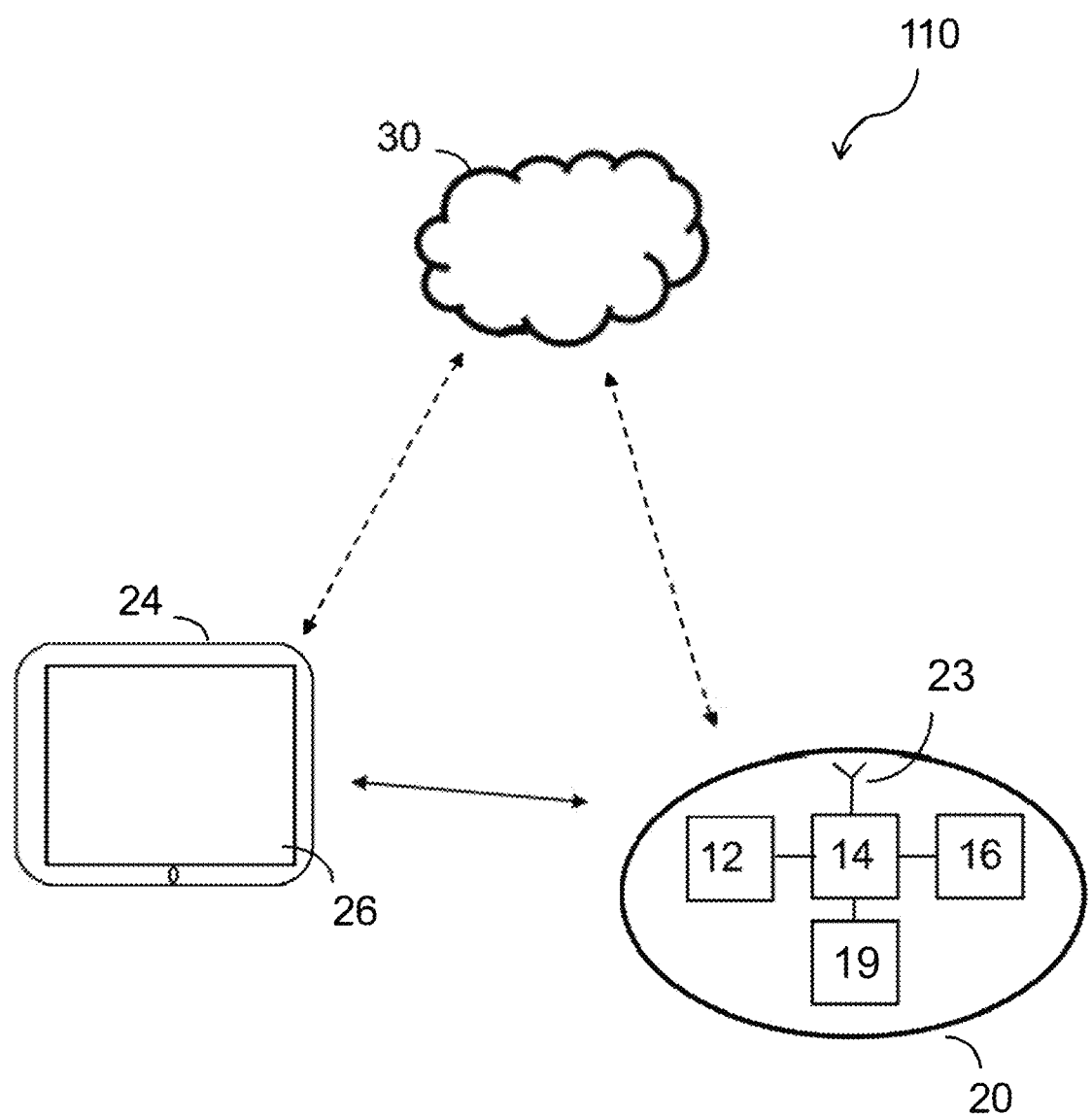
FIG. 14 illustrates a schematic of one embodiment of a system for assessing pre-term birth risk.
Figure 15:
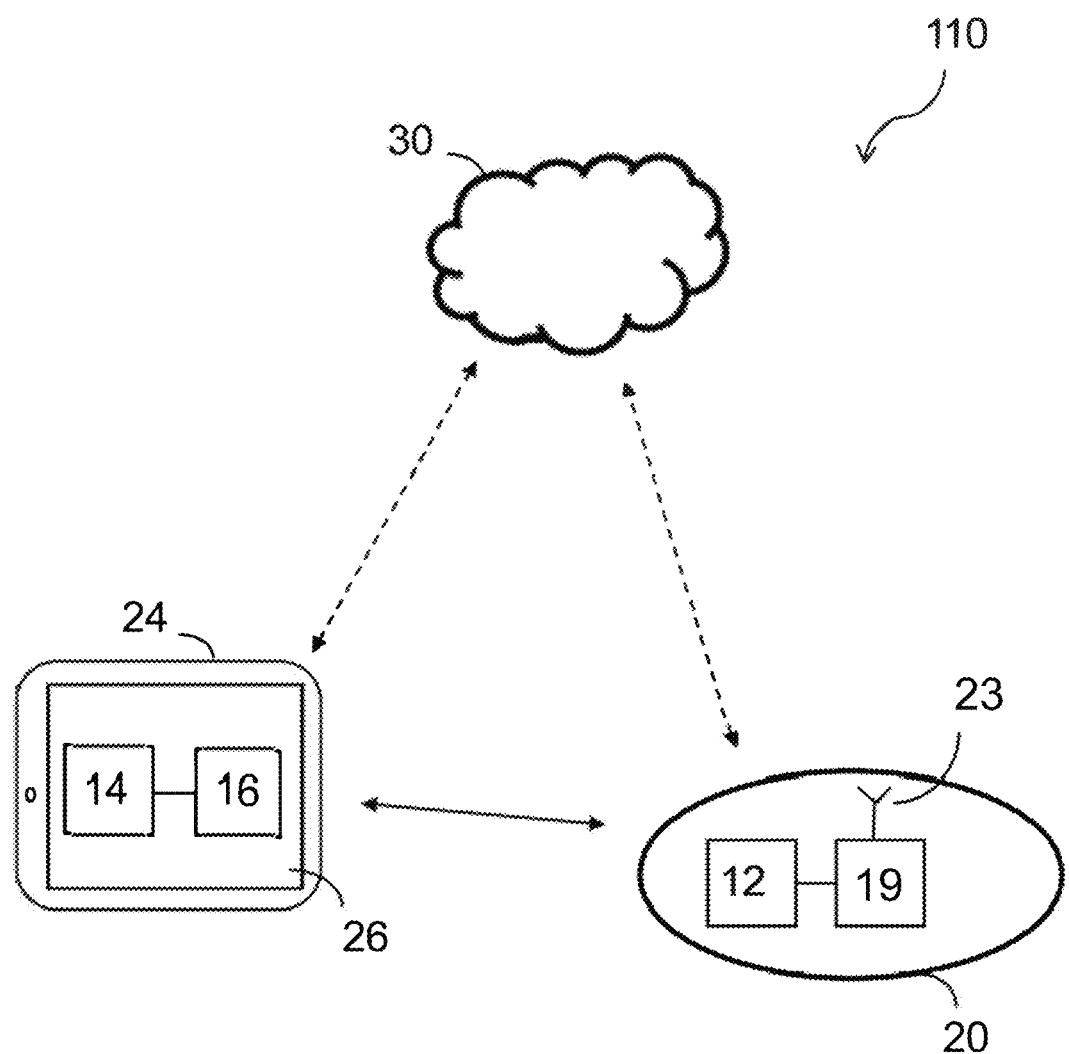
FIG. 15 illustrates a schematic of one embodiment of a system for assessing pre-term birth risk.
Figure 16:
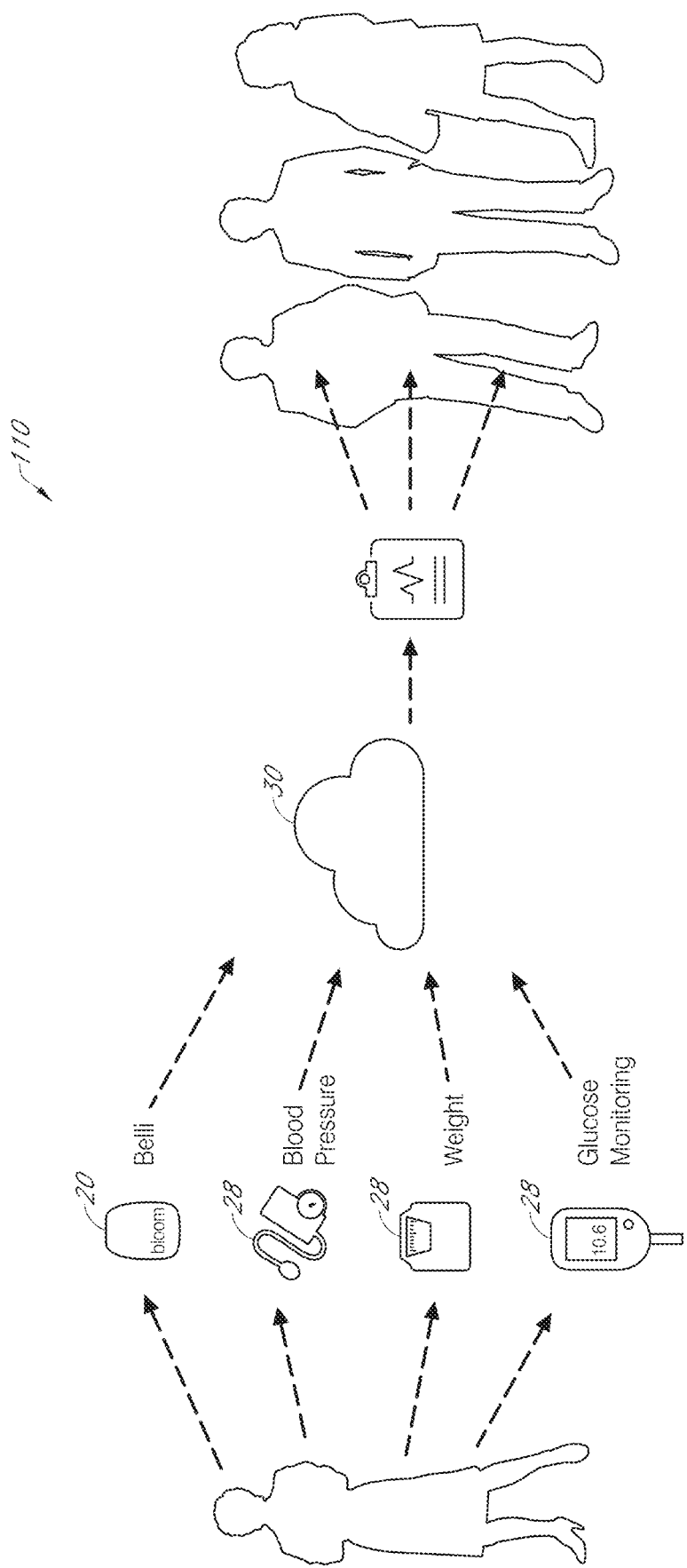
FIG. 16 illustrates schematically one embodiment of a system for assessing pre-term birth risk.
Figure 17:
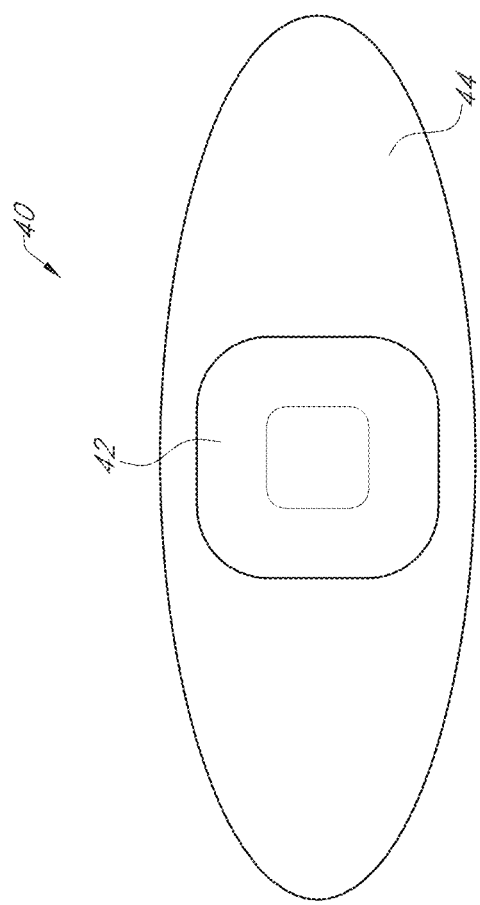
FIG. 17 illustrates one embodiment of a device configured to measure one or more physiological parameters for calculating a pre-term birth risk score based, at least in part, on the one or more physiological parameters.
Figure 18:
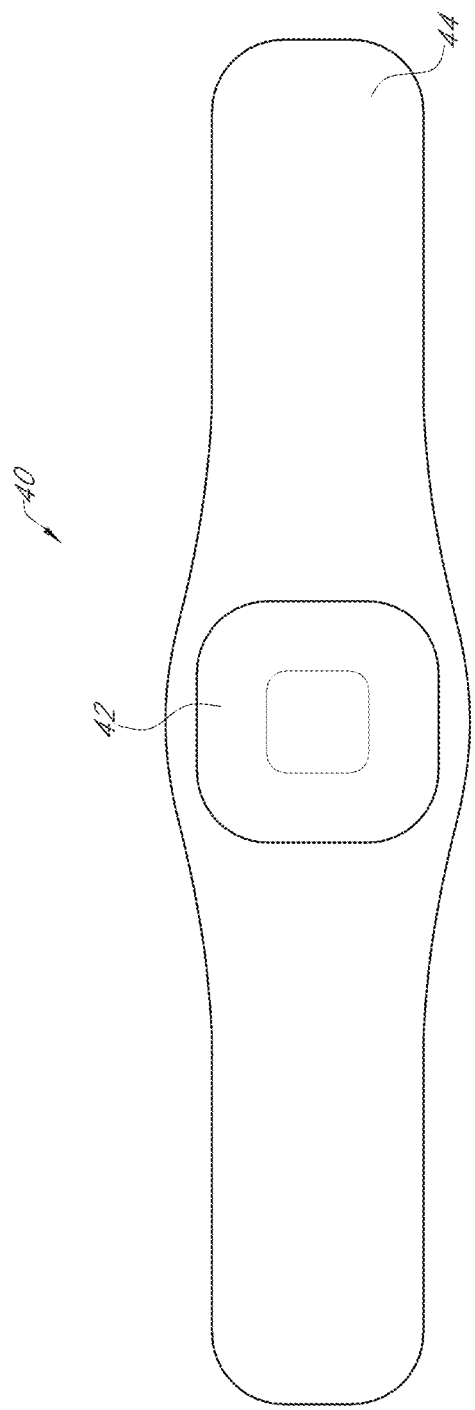
FIG. 18 illustrates one embodiment of a device configured to measure one or more physiological parameters for calculating a pre-term birth risk score based, at least in part, on the one or more physiological parameters.
Figure 19:
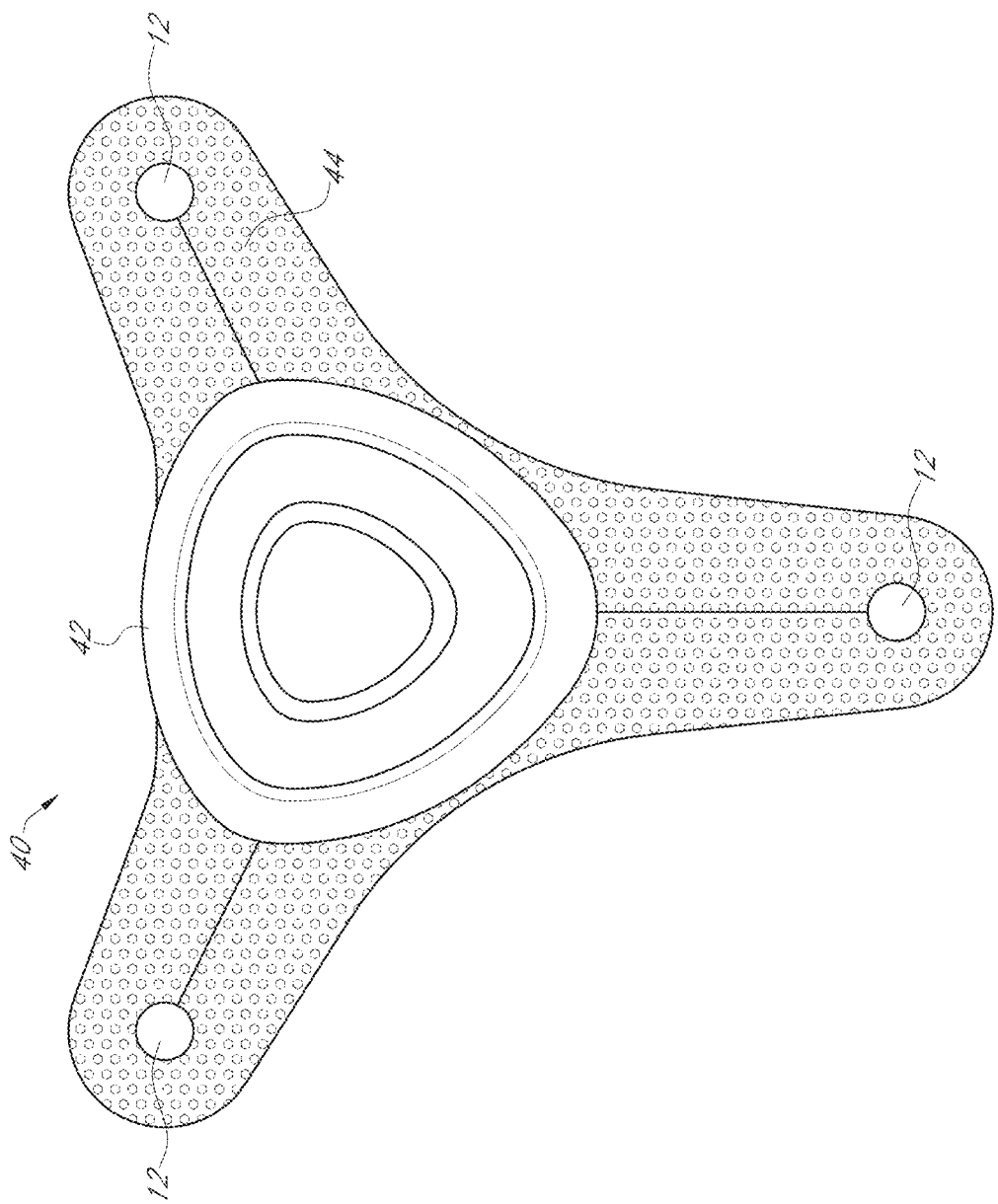
FIG. 19 illustrates one embodiment of a device configured to measure one or more physiological parameters for calculating a pre-term birth risk score based, at least in part, on the one or more physiological parameters.

As shown in FIGS. 13-15, a system 110 for assessing pre-term birth risk includes a sensor 12. The sensor 12 may sense one or more physiological signals. The sensor 12 may sense one or more of: an electrohysterography signal, an electromyography signal, an electrocardiogram signal, a temperature signal, a pulse oximetry signal, a respiration signal, a location signal, a movement signal, a skin conductance signal, and any other signal generated by a body of a pregnant female or a fetus carried therein. In some embodiments, the sensor 12 comprises one sensor; in some embodiments, the sensor 12 comprises a plurality of sensors. In one non-limiting example, the system includes at least two sensors 12, a measurement electrode and a reference electrode. In some embodiments, the system 110 comprises more than three sensors 12, for example four, five, six, or seven sensors. In some such embodiments, the sensors 12 include at least one reference electrode and a plurality of measurement electrodes.

Figure 20:
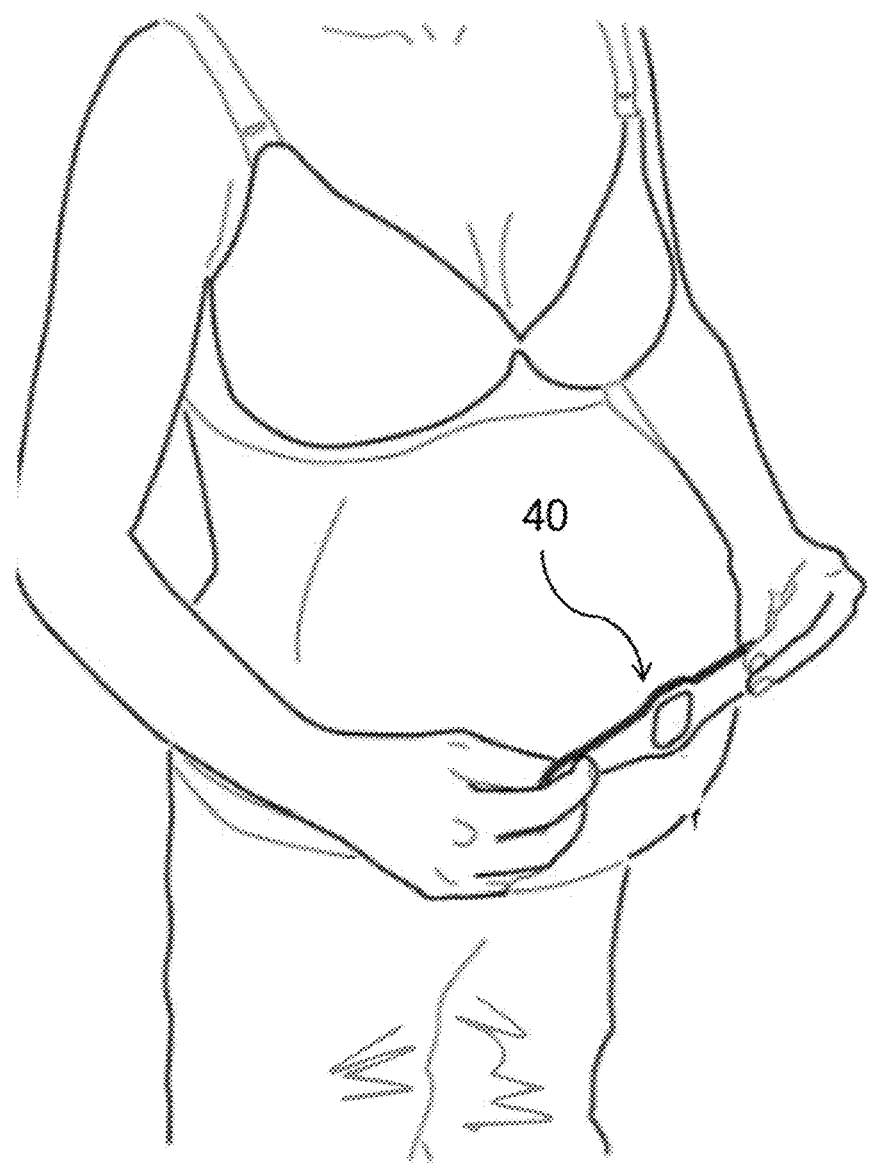
FIG. 20 illustrates one embodiment of a device configured for placement on a belly region of a pregnant female and configured to measure one or more physiological parameters for calculating a pre-term birth risk score based, at least in part, on the one or more physiological parameters.
Figure 21:
FIG. 21 illustrates one embodiment of a device configured for placement on a belly region of a pregnant female and configured to measure one or more physiological parameters for calculating a pre-term birth risk score based, at least in part, on the one or more physiological parameters.

In some embodiments, the sensor 12 is configured to be worn or positioned on a belly region of a pregnant female, as shown in FIGS. 20-21 and as described in further detail elsewhere herein. In some embodiments, the sensor 12 forms a portion of a sensor module 20, as shown in FIGS. 17-21 and as described in further detail elsewhere herein.

As shown in FIGS. 13-15, a system 110 for assessing pre-term birth risk includes a processor 14 and memory 16, as described elsewhere herein. The processor 14 functions to perform a method of assessing pre-term birth risk. The software may be programmed into the memory 16 or downloaded as an application onto the memory 16. The software may include instructions for running an operating system and/or one or more programs or applications. When executed by the processor 14, the programs or applications may cause the processor 14 to perform a method of assessing pre-term birth risk. Some such methods are described in more detail elsewhere herein.

As shown in FIG. 14, in some embodiments, the sensor 12, processor 14, and memory 16 form part of a sensor module 20. Alternatively, in some embodiments, the processor 14 and memory 16 reside in a separate system component, for example a computing device 24 communicatively coupled to the sensor module 20, as shown in FIG. 3 and as described in further detail elsewhere herein. The sensor module 20 of some embodiments functions to sense one or more signals, process and analyze the signals, and transmit the processed signals to a computing device 24 and/or server 30 communicatively coupled to the sensor module 20, as shown in FIG. 14. Alternatively, in some embodiments, the sensor module 20 functions to sense one or more signals and transmit the signals to a computing device 24 for processing and analyzing, as shown in FIG. 15. The sensor module 20 is configured for placement on a belly region of a pregnant female, as shown in FIGS. 20-21.

In some embodiments, the sensor module 20 is configured as a wearable patch 40 as shown in FIGS. 17-20 or as a wearable belt or strap 50 as shown FIG. 21. In some such embodiments, the patch 40 comprises a central region 42 coupled to a peripheral region 44. The central region 42 houses the processor 14, memory 16, antenna 20, one or more sensors 12, and/or one or more electronic circuits 18. In one embodiment, a portion of or all of the central region 42 is configured to be uncoupled or disengaged from the patch 40, as described in further detail in U.S. patent application Ser. No. 15/200,500 to Bloom Technologies NV, the disclosure of which is incorporated by reference in its entirety. In some embodiments, the peripheral region 44 comprises one or more sensors 12 and one or more electronic circuits 18. Further, in some embodiments, the peripheral region 44 includes an adhesive (e.g., pressure sensitive adhesive) for coupling the patch 40 to a skin surface of the user. In some variations, the peripheral region 44 may comprise a disposable material such as acrylate, a synthetic material, hydrogel, or silicone. In one embodiment, the peripheral region 44 comprises silicone. A reusable and/or disposable material may provide complete freedom and/or flexibility of use for the user. For example, the user may elect to move the patch 40 to another location depending on the time of day, activities occurring at a point in time, or based on one or more observations. Further for example, in some embodiments, a wearable belt 50 may comprise a breathable material, such as cotton, a partially or fully synthetic material, and/or elastic. The wearable belt 50 may be coupled to the pregnant female using Velcro, one or more buttons, a zipper, or, in some embodiments, the belt 50 may comprise a continuous elastic loop, such that the elasticity in a material of the belt 50 maintains the belt 50 at a specific location. As can be appreciated by one of skill in the relevant art, the patch 40 and/or belt 50 of FIGS. 17-21 may comprise any size, color, shape, and/or form factor required to achieve the intended function.

In some embodiments, as shown in FIGS. 14-15 a system 110 for assessing pre-term birth risk includes a sensor module 20 comprising an electronic circuit 19. The electronic circuit 19 functions to amplify, filter, digitize, and/or otherwise process the sensed signals for analyzing by the processor 14. In some embodiments, the electronic circuit 19 includes an operational amplifier; a low-pass, high-pass, or band-pass filter; an analog-to-digital (AD) converter; and/or other signal processing circuit components configured to amplify, filter, digitize, and/or otherwise process the signals. The electronic circuit 19 may additionally include a power supply or power storage device, such as a battery or capacitor to provide power to the other electronic components. For example, the electronic circuit 19 may include a rechargeable (e.g., lithium ion) or disposable (e.g., alkaline) battery. In some embodiments, the analyzed data is transmitted via an antenna 23 from the sensor module 20 to a computing device 24 for visualization on a display 26 or interpretation or viewing by a user or to a server 30 for storage or additional remote access, as shown in FIG. 14. Alternatively, in some embodiments, the sensed signals processed by the electronic circuit 19 are transmitted via an antenna 23 to a computing device 24 for further processing and/or analysis by a processor 14, as shown in FIG. 15.

In some embodiments, as shown in FIGS. 14-15, a system 110 for assessing a pre-term birth risk includes a computing device 24 communicatively coupled to a sensor module 20 and/or a server 30. The computing device 24 of some embodiments functions to receive analyzed data from the sensor module 20 in order to visually, audibly, or haptically represent the analyzed data to a user, to store the analyzed data, and/or to provide one or more recommendations or alerts to the user based on the analyzed data. Alternatively, in some embodiments, the computing device 24 functions to receive a processed signal from the sensor module 20 in order to analyze the processed signal and/or to visually, audibly, or haptically represent the analyzed data to a user, to store the analyzed data, and/or to provide one or more recommendations or alerts to the user based on the analyzed data.

In some embodiments, the computing device 24 is a computational device wrapped in a chassis that includes a visual display 26 with or without touch responsive capabilities (e.g., Thin Film Transistor liquid crystal display (LCD), in-place switching LCD, resistive touchscreen LCD, capacitive touchscreen LCD, organic light emitting diode (LED), Active-Matrix organic LED (AMOLED), Super AMOLED, Retina display, Haptic/Tactile touchscreen, or Gorilla Glass), an audio output (e.g., speakers), a central processing unit (e.g., processor or microprocessor), internal storage (e.g., flash drive), n number of components (e.g., specialized chips and/or sensors), and n number of radios (e.g., WLAN, LTE, WiFi, Bluetooth, GPS, etc.). In some embodiments, the computing device 24 comprises a mobile or portable computing device, for example a laptop, netbook, notebook, wearable device, personal digital assistance, cellular or mobile phone, or any other type of mobile or portable computing device. In some embodiments, the computing device 24 comprises a stationary computing device, for example a workstation or desktop computer.

In some embodiments, as shown in FIGS. 14-15, a system 110 for assessing a pre-term birth risk includes a server 30 communicatively coupled to a sensor module 20 and/or a computing device 24. The server 30 functions to receive processed sensor signals and/or analyzed data from one or more system components to remotely store and/or remotely provide access to the processed sensor signals and/or analyzed data. In some embodiments, the server 30 is a database server, application server, Internet server, or other remote server. In some embodiments, the server 30 may store user profile data, references, historical user data, historical community data, algorithms, machine learning models, software updates, or other data. The server 30 may share the information with the computing device 24 or the sensor module 20, and the server 30 may receive newly acquired user data from the sensor module 20 and/or the computing device 24.

In some embodiments, the computing device 24 and/or server 30 further receive acquired user data from a secondary device 28 (e.g., health monitoring device) communicatively coupled to the system 110, as shown in FIG. 15. In some embodiments, as shown in FIG. 15, a system 110 for assessing a pre-term birth risk includes a secondary device 28. The secondary device 28 functions to sense, measure, or otherwise track a health-related parameter of a user. The sensed signals may be processed and analyzed locally on the secondary device 28 or transmitted to a sensor module 20, a computing device 24, and/or server 30 communicatively coupled to the secondary device 28 for signal processing and analysis. For example, a health-related parameter may include blood-pressure, weight, glucose level, temperature, activity level, heart rate, stress level, sleep quality, or any other parameter. In some embodiments, the secondary device 28 is a scale, thermometer, blood pressure monitor or cuff, Fitbit®, Pebble®, Blood or Interstitial Glucose Monitor, Garmin® device, Jawbone® device, Misfit® device, Xiaomi® device, Samsung® device, Apple® Watch, pacemaker, or any other device.

In some embodiments, there is bidirectional communication between system components. The bidirectional communication may comprise wireless (e.g., Bluetooth, low energy Bluetooth, near-field communication, infrared, WLAN, Wi-Fi, CDMA, LTE, other cellular protocol, other radiofrequency, or another wireless protocol) or wired (as IEEE 1394, Thunderbolt, Lightning, DVI, HDMI, Serial, Universal Serial Bus, Parallel, Ethernet, Coaxial, VGA, or PS/2) communication. For example, there may be directional communication between the sensor module 20 and computing device 24, the sensor module 20 and the server 30, the computing device 24 and the server 30, the secondary device 28 and the server 30, the secondary device 28 and the sensor module 20, and/or the secondary device 28 and the computing device 24.

Figure 40:
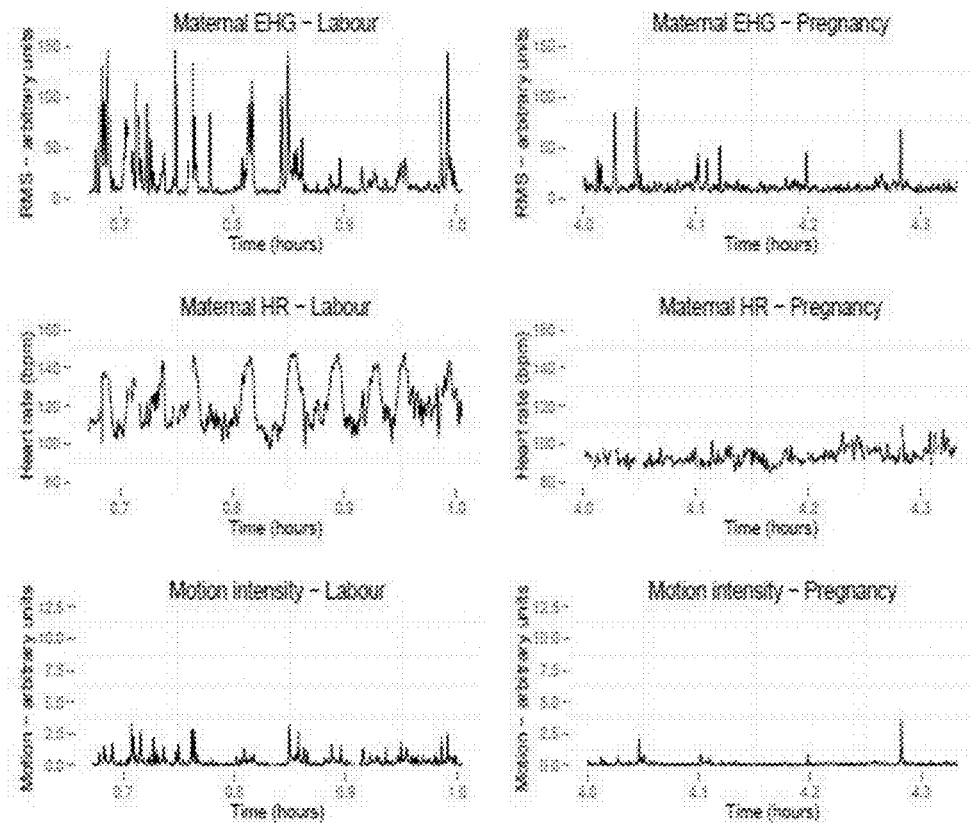
FIG. 40 shows an example of EHG and HR data for comparing two sessions, a pregnant woman in labor and a pregnant woman not in labor

In some embodiments, as shown in FIGS. 17-21, a pregnant woman may wear a wearable device, e.g., patch 40, to detect one or more features, e.g., biopotential signals such as EHG and/or HR. In some instances, the biopotential signals detected may be representative of the rhythmic pattern present in both EHG and HR data as a consequence of increased uterine activity. In some cases, the contractions may not be manually selected, but analyzed over longer periods of time to detect the one or more biopotential signals representative of labor without requiring manual data segmentation. In some embodiments, the detected biopotential signals may be observed over a particular time window, e.g., 20 minutes to 30 minutes, such that the time window is both long enough to capture rhythmic patterns and short enough to exclude noise (which could be present in longer measurements due to maternal movement). FIG. 40 shows an example of EHG and HR data for comparing two sessions, a pregnant woman in labor and a pregnant woman not in labor (i.e., pregnancy). Accelerometer data is shown as context, as all recordings where selected during periods of no or low motion to avoid artifacts. In some embodiments, the patch 40 may be configured to acquire two channels of biopotential signals at 4096 Hz and triaxial accelerometer data at 128 Hz from a single sensor placed on the abdomen. The patch 40 may be placed on the skin of a pregnant woman using a medical grade adhesive patch, as shown in FIGS. 20-21.

Artifacts, as mentioned above, may be talking, coughing, turning to a side, stretching, walking, standing up, playing with a toddler, bending, rubbing the abdomen, and contracting the abdomen and rectum. These activities are representative of daily life and typically interfere with EHG and HR data.

In some embodiments, the EHG may be analyzed by down sampling biopotential data to 16 Hz, as EHG signal energy ranges from 0.1-5 Hz. In some instances, a low-pass Finite Impulse Response (FIR) filter (4 Hz cutoff frequency) and a high-pass FIR filter (0.1 Hz cutoff frequency) may be applied to isolate the main frequency of interest for EHG data. In some instances, HR may be analyzed by a reprocessing step comprising band-pass filtering a first biopotential signal between 2 Hz and 98 Hz to remove all out-of-noise and a notch filter at 50 Hz to remove powerline interference. In some cases, accelerometer data may be bandpass filtered between 1 and 10 Hz to isolate maternal movement.

Figure 30:
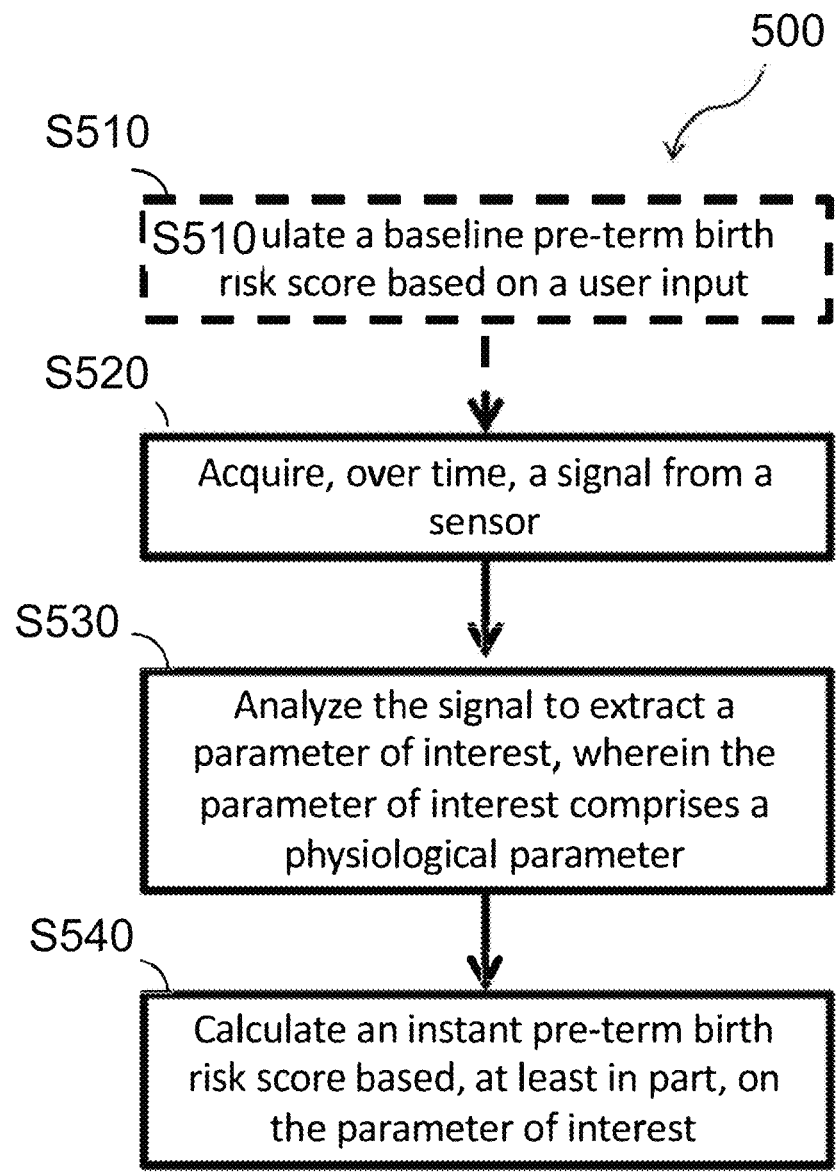
FIG. 30 illustrates a flow chart of one embodiment of a method of assessing a pre-term birth risk.

As shown in FIG. 30, one embodiment of a method 500 for assessing over time a pre-term birth risk of a pregnant female includes: optionally, calculating a baseline pre-term birth risk score based on a user input S510; acquiring, over time, a signal from a sensor S520; analyzing the signal to extract a parameter of interest, wherein the parameter of interest comprises a physiological parameter S530; and calculating an instant pre-term birth risk score based, at least in part, on the parameter of interest S540. The method 500 functions to calculate, over time, an instant pre-term birth risk score, for example to show an improvement or worsening of the instant pre-term birth risk score relative to a baseline pre-term birth risk score.

As shown in FIG. 30, one embodiment of a method 500 for assessing over time a pre-term birth risk of a pregnant female optionally includes block S510, which recites calculating a baseline pre-term birth risk score based on a user input. Block S510 functions to receive user entered data to calculate a baseline pre-term birth risk score. The data may be input into the system using text, speech, or one or more touch-based graphical user interfaces (GUIs). The GUI may include buttons, sliders, toggle buttons, toggle switches, switches, dropdown menus, combo boxes, text input fields, check boxes, radio buttons, picker controls, segmented controls, steppers, and/or any other type of control. The baseline pre-term birth risk score may be calculated using user height metrics, user weight metrics, user background information, previous pregnancy information, user risk factors data, and/or user lifestyle data. In one embodiment, calculating comprises using Bayesian linear regression.

As shown in FIG. 30, one embodiment of a method 500 for assessing over time a pre-term birth risk of a pregnant female includes block S520, which recites acquiring, over time, a signal from a sensor. Block S520 functions to sense one or more signals from a body of the pregnant female or a fetus she is carrying therein. For example, the system may sense a maternal or fetal heart electrical activity signal (e.g., heart rate, heart rate variability), a uterine electrical activity signal (e.g., contractions), a temperature signal, a skin signal (e.g., Galvanic skin response), a maternal or fetal light absorption signal (e.g., blood oxygen saturation), a maternal or fetal positional or acceleration signal (e.g., activity level), or any other signals emanating from a pregnant female's body or a body of one or more fetuses she is carrying. In some embodiments, one or more signals are acquired hourly, daily, weekly, or monthly. In some embodiments, one or more signals are acquired manually or on demand, for example as requested by the pregnant female or a healthcare provider. Alternatively, one or more signals may be acquired automatically, for example according to a pre-set schedule, upon detection of a change or lack thereof in a signal, or randomly. In some embodiments, block S520 is performed by a sensor module or a secondary device communicatively coupled to the system. In one embodiment, block S520 is performed by a sensor module.

As shown in FIG. 30, one embodiment of a method 500 for assessing over time a pre-term birth risk of a pregnant female includes block S530, which recites analyzing the signal to extract a parameter of interest, wherein the parameter of interest comprises a physiological parameter. Block S530 functions to identify and extract a parameter of interest from the sensor signal. In some embodiments, a parameter of interest is extracted based on identifying repetitive features of the sensor signal, identifying one or more changes in the sensor signal indicative of a real event versus background, removing background or noise from the sensor signal, identifying known patterns in the sensor signal, or any other extraction method. In some embodiments, block S130 is performed by a processor housed in a computing device, sensor module, server, or secondary device communicatively coupled to the system. In one embodiment, block S530 is performed by a sensor module. In another embodiment, block S530 is performed by a computing device.

In some embodiments, block S530 may include extracting two sets of data to be used for classification. In some embodiments, features, e.g., biopotential signals, may be extracted over approximately 16 second windows to capture EHG and cardiac properties, e.g., HR. In other embodiments, one or a plurality of data sets may be extracted over 1-10 second, 10-20 second, 20-30 second, 30-40 second, 40-50 second, or 50-60 second windows, or any range or subrange therebetween. As shown in FIG. 40, two features are seen where the Root Mean Square (RMS) of the EHG signal and the mean HR over consecutive 16 second windows are shown. In this case, the extracted features were RMS of the EHG signal, normalized range of the EHG signal $$\left(\frac{\max - \min}{\sigma}\right),$$

mean crossing rate of the EHG signal, power of the EHG signal, and mean HR. The features may then be summarized in terms of mean and standard deviation over 20 minute windows or any length of window that is appropriate. Additionally, computed features may be computed on the entire 20 minute segment, with the aim of capturing more information relative to the rhythmic pattern present during pregnancy. In this instance, power of the EHG and HR signal, frequency, and amplitude of the main peak (EHG and HR), HR quantiles and max autocorrection of the HR signal may be extracted. In some embodiments, a result of each 20 minute segment may be characterized by a set of EHG and HR-derived features, plus GA (gestational age), for a total of two segments per participant, pregnant woman.

In some embodiments, generalized linear models (GLMs) may be developed to estimate artifacts and labor probability using datasets, EHG, HR and GA, with the RMS. Models may be derived and validated using cross-validation and a binary classification problem distinguishing artifacts from non-artifacts and labor from non-labor recordings. In some cases, the GLMs may be defined as $\mu_i = g(\eta_i)$, wherein g is the link function, i.e., the logit function as errors follow a binominal distribution. The transformed expected value $\mu$ is a linear function of the predictors and can be defined as $\mu_i = x_i \beta$, where $x_i$ is the array of EHG, HR, and GA features.

GLMs produce an output probability, and a threshold needs to be selected in order to transform the output into a discrete class. In this instance, the threshold for artifact probability estimation models may be 0.5 so that an artifact is detected when the probabilistic output is greater than 0.5. In this case, as artifacts are analyzed on a window by window basis, e.g., 20 minute segments, each segment may be further analyzed to determine the percentage of the detected artifact. Given the high influence of artifacts on physiological data, e.g., EHG and HR, a conservative threshold may be used, e.g., recordings that were at least 85% artifact free may be considered for high labor probability estimation.

Figure 41:
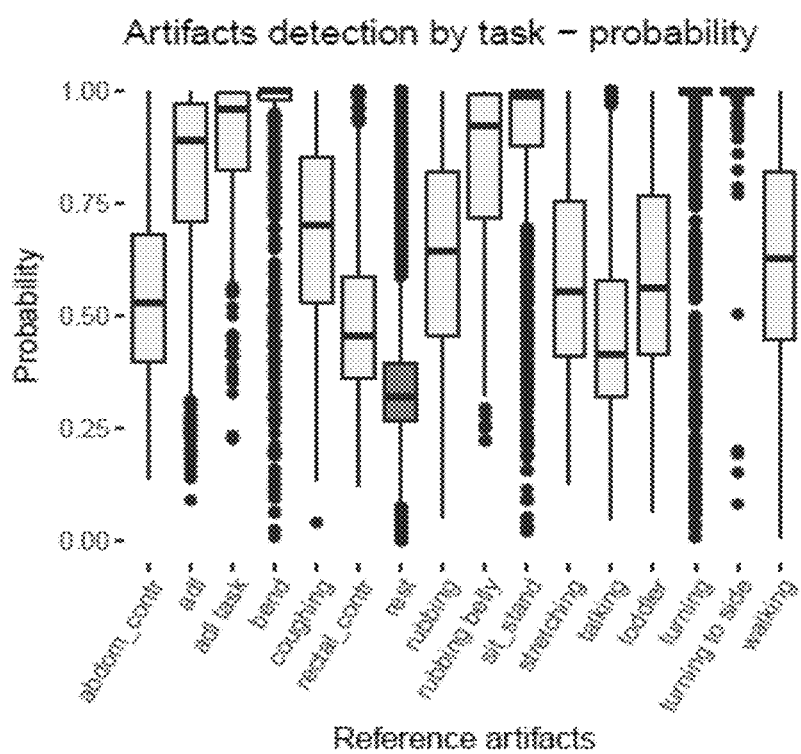
FIG. 41 shows a schematic representation of artifact probability estimation results.
Figure 42:
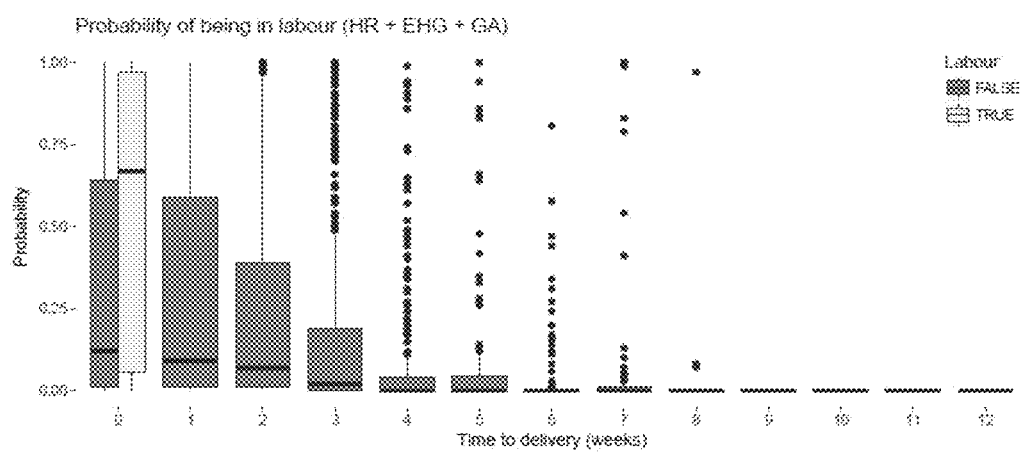
FIG. 42 shows a schematic representation of labor probability for reference labor recordings.
Figure 43:
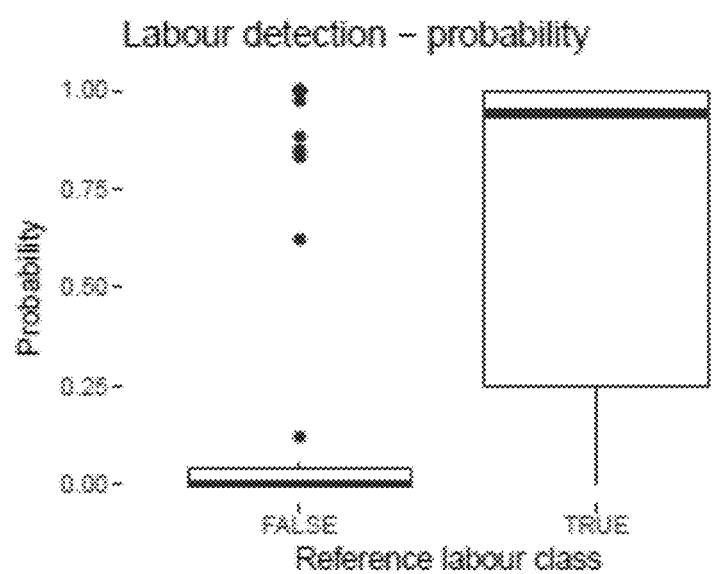
FIG. 43 shows a schematic representation of actual labor probability.

In a particular example, artifact probability estimation results are shown in FIG. 41, for a dataset and a series of activities (e.g., bending, coughing, stretching, etc.). In these cases, rest includes both periods of actual rest and clean labor recordings. The average artifacts probability for reference artifacts was 63% while it was 32% for reference rest and labor data (medians were 62% and 31%, respectively). As shown in FIG. 41, some activities elicit high artifacts probability, e.g. sit to stand, while others have less impact on signal quality, e.g., talking. In this case, labor probability, as shown in FIG. 42, for reference labor recordings was 67% while it was 20% for reference pregnancy recordings collected outside of free living environments (medians were 94% and 0%, respectively). Actual labor probability is shown in FIG. 43.

As shown in FIG. 30, one embodiment of a method 500 for assessing over time a pre-term birth risk of a pregnant female includes block S540, which recites calculating an instant pre-term birth risk score based, at least in part, on the parameter of interest. Block S540 functions to determine an instant pre-term birth risk score of the user. For example, the instant pre-term birth risk score may be calculated on demand upon request by the pregnant female, a healthcare provider, or other user of the system. Alternatively or additionally, the instant pre-term birth risk score may be calculated automatically, at a pre-determined interval, randomly, or upon detection of a change or lack thereof in one or more factors that comprise the instant pre-term birth risk score. In one embodiment, calculating comprises using Bayesian linear regression. In one embodiment, calculating is performed using machine learning techniques, for example, linear regression, logistic regression, decision tree, support vector machine, random forest, etc.

In some embodiments, as shown in block S540, calculating may include choosing random forests as classifiers and not performing feature selection as during training random forests (e.g., picking a subset of the available features in iteration). In some cases, random forests may be fed seven different feature sets, in order to analyze differences in accuracy for EHG, HR, combined EHG and HR, and also GA as an additional feature, which is inputted by the user, starting from a lower bound on accuracy provided by using only GA as a predictor. In this instance, features may be computed over 20 minute segments or any relevant segment of time.

In some variations, the method 500 includes receiving a user input, and calculating the instant pre-term birth risk score based, at least in part, on the parameter of interest and the user input. In such variations, receiving the user input may include receiving user entered information, as described elsewhere herein. Alternatively or additionally, receiving the user input may include receiving user data from a server, computing device, or secondary device communicatively coupled to the system. In another embodiment, receiving the user input may include receiving user data from a healthcare provider or a system managed by a healthcare provider, for example an electronic patient record or electronic medical record.

In some embodiments, the method includes comparing the parameter of interest to an individual baseline for the parameter of interest; and calculating the instant pre-term birth risk score based, at least in part, on a deviation between the parameter of interest and the individual baseline for the parameter of interest.

Figure 22:
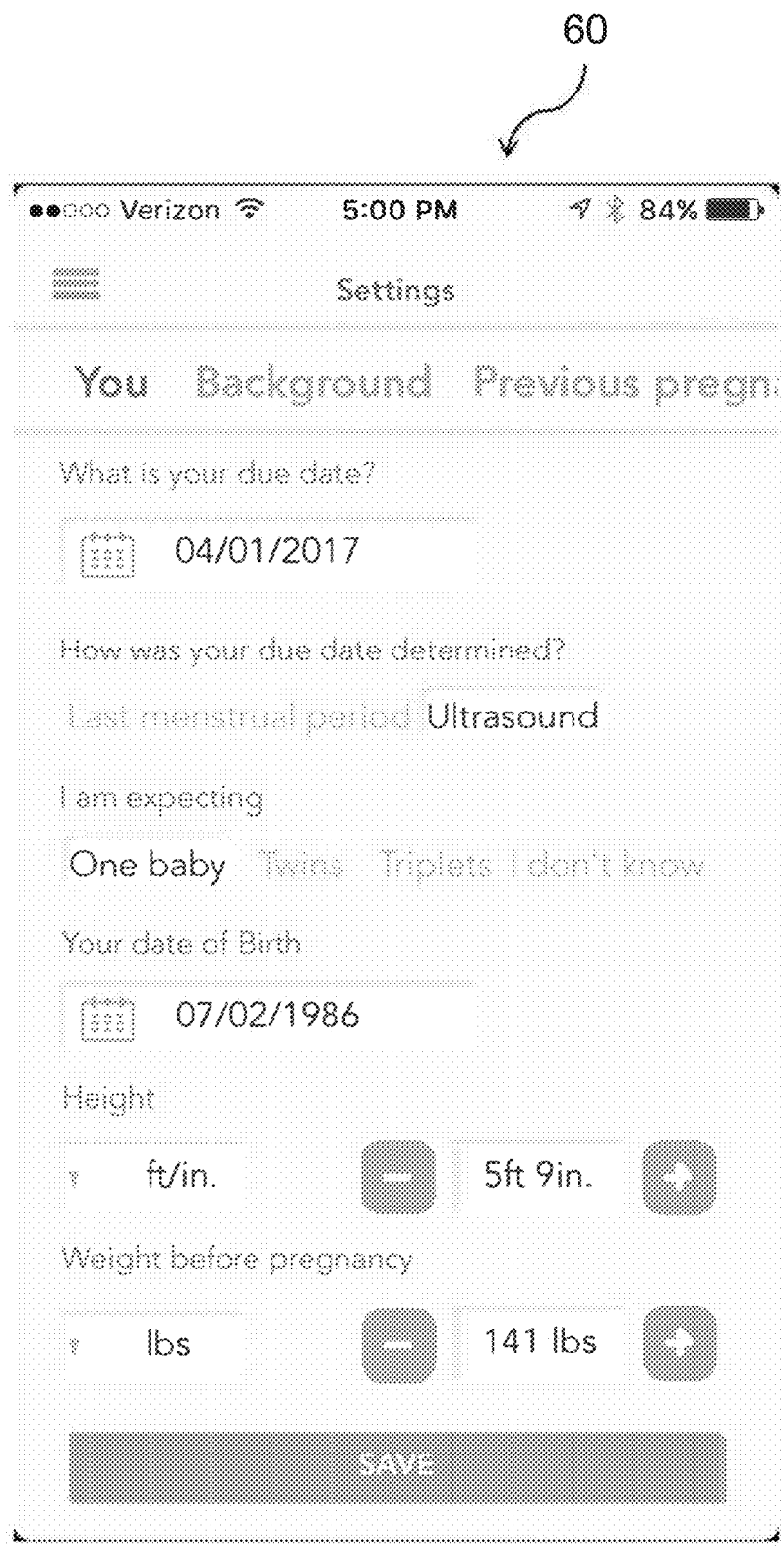
FIG. 22 illustrates one embodiment of a graphical user interface for receiving user input to calculate a pre-term birth risk score based, at least in part, on the user input.

In one non-limiting example, as shown in FIG. 22, a GUI 60 may be configured to receive user input data related to due date, number of babies that the user is carrying, a date of birth of the user, a height of the user, and a weight of the user.

Figure 23:
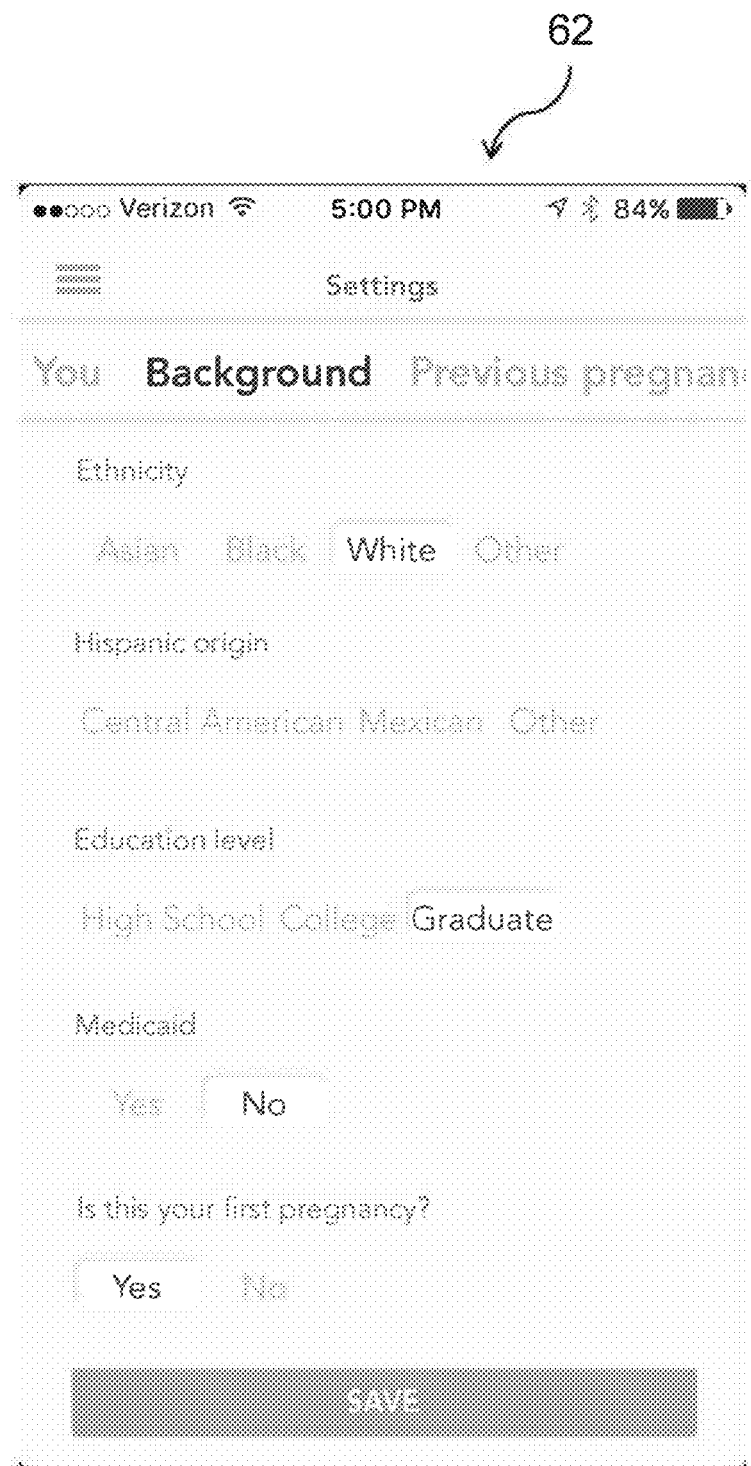
FIG. 23 illustrates one embodiment of a graphical user interface for receiving user input to calculate a pre-term birth risk score based, at least in part, on the user input.

In another non-limiting example, as shown in FIG. 23, a GUI 62 may be configured to receive user input data related to a background or demographic (e.g., ethnicity, education level, use of Medicaid, and a number of pregnancies that the user had previously) of the user.

Figure 24:
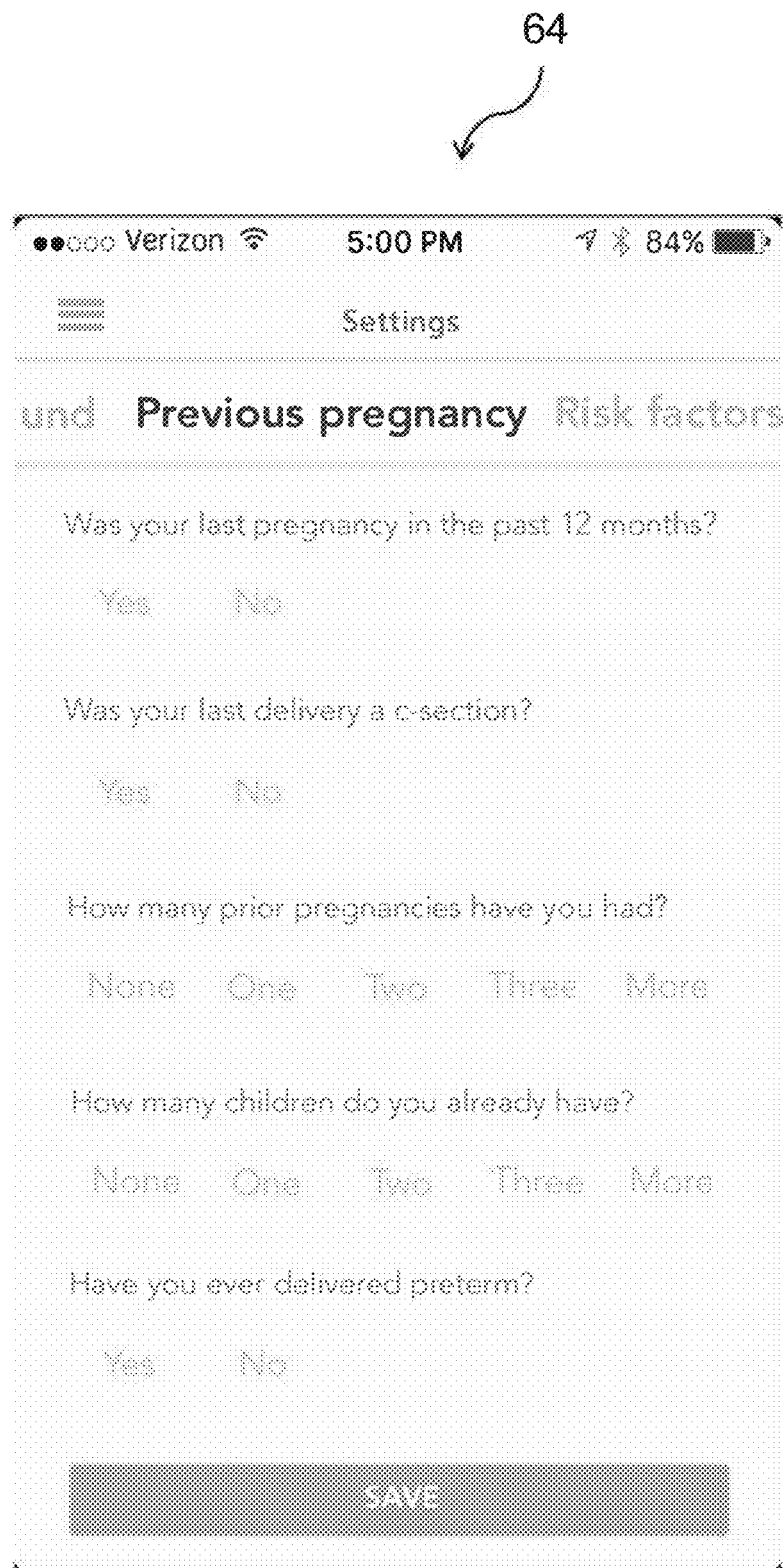
FIG. 24 illustrates one embodiment of a graphical user interface for receiving user input to calculate a pre-term birth risk score based, at least in part, on the user input.

In another non-limiting example, as shown in FIG. 24, a GUI 64 may be configured to receive user input data related to one or more previous pregnancies of the user, for example a timeline of a previous pregnancy (e.g., date of delivery, date of conception, number of months between delivery and conception, etc.), a type of delivery (i.e., vaginal or C-section), a number of previous pregnancies, a number of current children, a number of previous pre-term deliveries, etc.

Figure 25:
FIG. 25 illustrates one embodiment of a graphical user interface for receiving user input to calculate a pre-term birth risk score based, at least in part, on the user input.

In another non-limiting example, as shown in FIG. 25, a GUI 66 may be configured to receive user input data related to risk factors of the user, for example hypertension pre-pregnancy, diabetes pre-pregnancy, gestational diabetes, gestational hypertension, preeclampsia, eclampsia, receipt of infertility treatments, etc.

Figure 26:
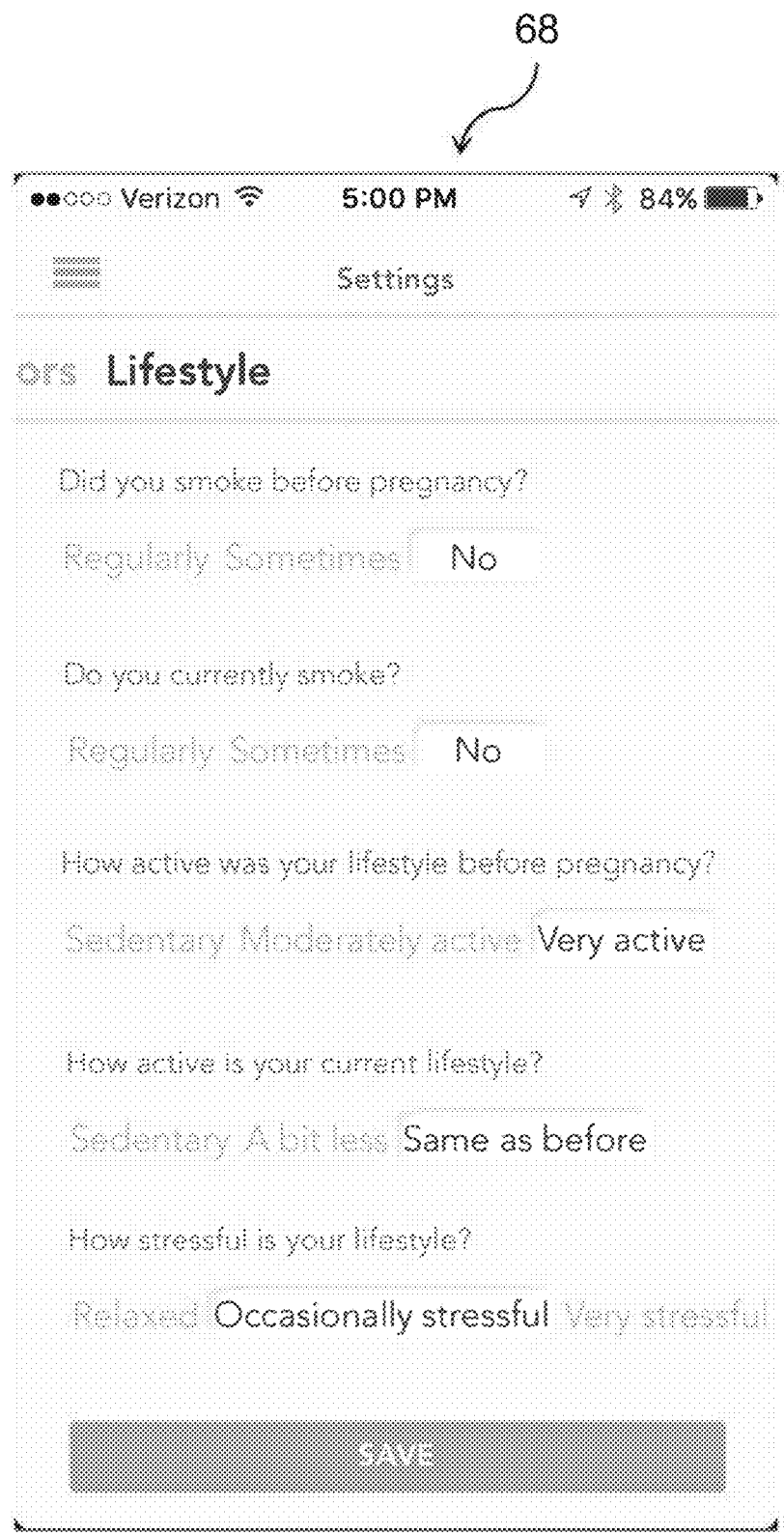
FIG. 26 illustrates one embodiment of a graphical user interface for receiving user input to calculate a pre-term birth risk score based, at least in part, on the user input.

In another non-limiting example, as shown in FIG. 26, a GUI 68 may be configured to receive user input data related to a lifestyle of the user, for example smoking frequency, activity level pre-pregnancy, activity level during pregnancy, stressfulness of lifestyle, an alcohol consumption metric, a recreational drug use frequency, a coitus frequency, an eating frequency and/or quality, a frequency of traveling, etc.

In some embodiments, the method 500 includes: comparing the instant pre-term birth risk score to a baseline pre-term birth risk score; and when the instant pre-term birth risk score differs from the baseline pre-term birth risk score, updating the baseline pre-term birth risk score with the instant pre-term birth risk score. In such embodiments, the system provides the user, for example pregnant female or healthcare provider, with an accurate, up-to-date pre-term birth risk score. As such, the pregnant female may make changes to her lifestyle, eating habits, exercise schedule, or other habits or activities to positively affect or at least maintain her pre-term birth risk score. Further, the healthcare provider may make changes to a therapy or medication regimen, a consultation or office visit schedule, or other recommendations to encourage the pregnant female to positively affect or at least maintain her pre-term birth risk score.

In some embodiments, the method 500 includes providing one or more of: a baseline pre-term birth risk score and an instant pre-term birth risk score to a user, for example a healthcare provider. In some such embodiments, the user may receive the baseline or instant pre-term birth risk score via a computing device or server communicatively coupled to the system. The baseline and/or instant pre-term birth risk scores may be viewable together with additional user information, for example one or more factors that comprise the baseline and/or instant pre-term birth risk score. In some embodiments, the system provides one or more recommendations to the user about activities, medications, habits, foods, etc. that the user, for example healthcare provider, may suggest to the pregnant female to improve her instant pre-term birth risk score. In some embodiments, the system connects the user with additional resources, for example specialists or publications, that may improve the care of the pregnant female and ultimately her instant pre-term birth risk score.

In some embodiments, the method 500 includes: categorizing a group of pregnant females according to one or more of: their baseline pre-term birth risk score and their instant pre-term birth risk score. In such embodiments, categorizing pregnant females according to their pre-term birth risk score may improve care, provide a community through which ideas can be shared, for example how to reduce pre-term birth risk and/or identify new factors or characteristics associated with pre-term birth. Further, categorizing pregnant females according to their pre-term birth risk score may improve a functionality of the system to locate references or datasets that include features or characteristics in common with a given cohort of pregnant females that may be used in additional methods described elsewhere herein.

In some embodiments, the method 500 includes: varying a treatment, adapting prenatal care, and/or varying a frequency of consultation based on one or more of: the baseline pre-term birth risk score and the instant pre-term birth risk score. For example, if a pregnant female has a high baseline pre-term birth risk score and/or an instant pre-term birth risk score that is, in general, increasing over time, the system may provide a recommendation that a treatment course, dose, and/or type be varied. The system may recommend starting or increasing a dose of an antenatal corticosteroid, an antibiotic, a tocolytic, progesterone, or another medication. Alternatively or additionally, the system may recommend cerclage and/or bed rest.

In some embodiments, the method 500 includes: displaying one or more of: the baseline pre-term birth risk score and the instant pre-term birth risk score to the pregnant female, a healthcare provider, a family member, or another user. Alternatively or additionally, the method 500 includes: displaying a series of factors that influence one or more of: the baseline pre-term birth risk score and the instant pre-term birth risk score to the pregnant female or another user.

For example, a GUI of the system may display a baseline pre-term birth risk score; an instant pre-term birth risk score; a change over time in the pre-term birth risk score; a breakdown of one or more factors affecting the pre-term birth risk score; a percent of pregnant females with a higher, lower, or similar pre-term birth risk score; a percent of pregnant females with a similar or same condition or feature as the pregnant female; or any other parameter in a schematic, graphic, text, alert, recommendation, or any other visual, audible, or tactile display.

Figure 27:
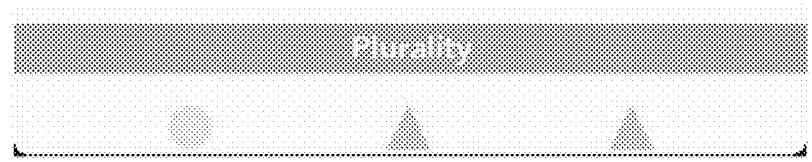
FIG. 27 illustrates one embodiment of a graphical user interface configured to display a breakdown of a user's pre-term birth risk score.

In one non-limiting embodiment, as shown in FIG. 27, a GUI 72 may be configured to display a risk breakdown, for example a percent of women, with characteristics similar to the pregnant female, that delivered pre-term.

In another non-limiting embodiment, as shown in FIG. 28, a GUI 74 may be configured to display a percent of women in a specific region or country that were diagnosed with a similar or same condition as the pregnant female and a percent of women with characteristics or features similar to the pregnant female that were also diagnosed with a condition similar to or the same as the pregnant female.

In another non-limiting embodiment, as shown in FIG. 29, a GUI 76 may be configured to display a breakdown of a baseline or instant pre-term birth risk. For example, the GUI 76 may display a percent of pregnant females with an increased or decreased risk of pre-term birth relative to the pregnant female. In one embodiment, an up pointed symbol or arrow indicates pregnant females with a higher risk of pre-term birth compared to the pregnant female and a down pointed symbol, arrow indicates pregnant females with a lower risk of pre-term birth compared to the pregnant female, and a circle or other shape indicates a present position or pre-term birth risk of the pregnant female using the system.

Figure 31:
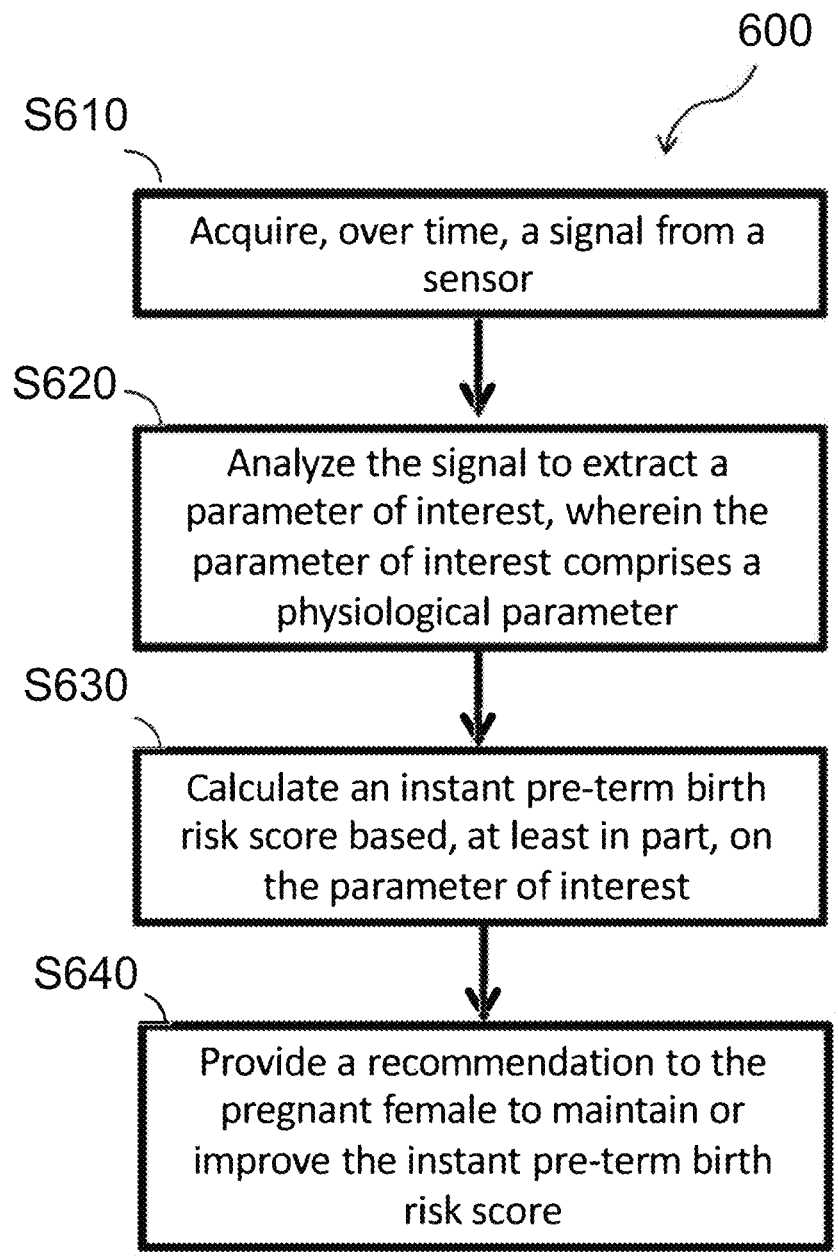
FIG. 31 illustrates a flow chart of one embodiment of a method of assessing a pre-term birth risk.

As shown in FIG. 31, one embodiment of a method 600 for assessing over time a pre-term birth risk of a pregnant female includes acquiring, over time, a signal from a sensor S210; analyzing the signal to extract a parameter of interest, wherein the parameter of interest comprises a physiological parameter S620; calculating an instant pre-term birth risk score based, at least in part, on the parameter of interest S630; and providing a recommendation to the pregnant female to maintain or improve the instant pre-term birth risk score S640. The method 600 functions to enable and/or empower the pregnant female to adapt or change her lifestyle, eating habits, exercise habits, stress load, sleeping habits, or other choices to improve her pre-term birth risk score. In some embodiments, block S640 includes: changing an activity level, reducing or stopping smoking, reducing or stopping alcohol consumption, increasing an amount of rest, decreasing a stress level (e.g., breathing exercise, meditation, mindfulness session, etc.), drinking more water, increasing an amount of sleep, increasing an amount of healthy foods consumed, reducing or stopping drug use, changing a caloric intake, changing a medication regimen, changing a frequency of consultation, changing a prenatal care regimen, consulting a healthcare provider, contacting an emergency service provider, or another recommendation.

Figure 32:
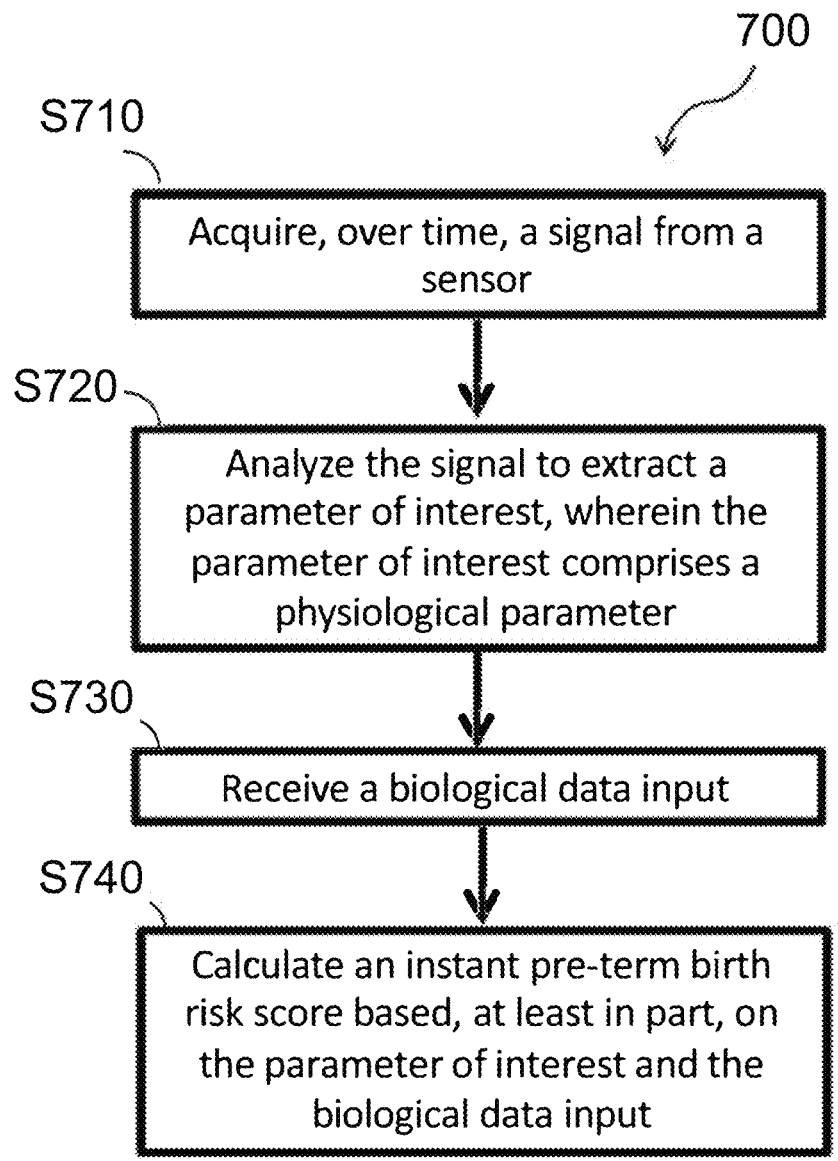
FIG. 32 illustrates a flow chart of one embodiment of a method of assessing a pre-term birth risk.

As shown in FIG. 32, one embodiment of a method 700 for assessing over time a pre-term birth risk of a pregnant female includes acquiring, over time, a signal from a sensor S310; analyzing the signal to extract a parameter of interest, wherein the parameter of interest comprises a physiological parameter S720; receiving a biological data input S730; and calculating an instant pre-term birth risk score based, at least in part, on the parameter of interest and the biological data input S740. The method 700 functions to include relevant biological data or test results into the calculation of the baseline and/or instant pre-term birth risk score. Non-limiting examples of biological data inputs include: a biological test result, a blood test result (e.g., alpha-fetoprotein, estriol, human chorionic gonadotropin, inhibin, etc.), an ultrasound screening result, a vaccination record (e.g., seasonal influenza, tetanus, diphtheria, pertussis, etc.), proteomics data, genetic data (e.g., DNA mutations, etc.), serum test results, and an amniocentesis result (e.g., birth defects, chromosomal abnormalities, etc.). In some embodiments, the biological data input is entered into a GUI of a computing device communicatively coupled to the system by a user, for example a pregnant female or healthcare provider. In some embodiments, the biological data input is automatically or manually transmitted to a computing device communicatively coupled to the system via a server or another computing device via a wired connection or wirelessly.

Figure 33:
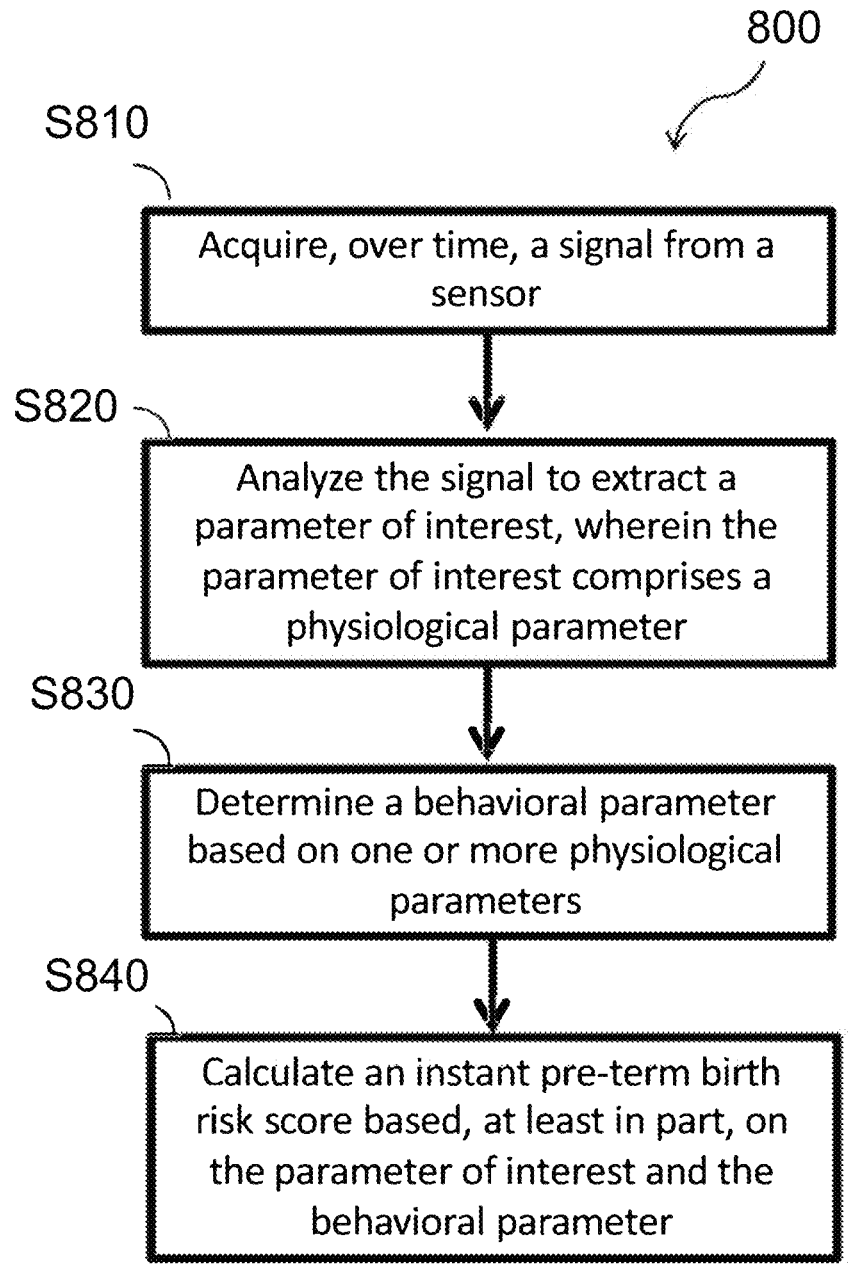
FIG. 33 illustrates a flow chart of one embodiment of a method of assessing a pre-term birth risk.

As shown in FIG. 33, one embodiment of a method 800 for assessing over time a pre-term birth risk of a pregnant female includes acquiring, over time, a signal from a sensor S410; analyzing the signal to extract a parameter of interest, wherein the parameter of interest comprises a physiological parameter S820; determining a behavioral parameter based on one or more physiological parameters S830; and calculating an instant pre-term birth risk score based, at least in part, on the parameter of interest and the behavioral parameter S840. The method 800 functions to use one or more physiological parameters to calculate one or more behavioral parameters and to incorporate the one or more behavioral parameters into a calculation of the instant pre-term birth risk score.

FIGS. 35-39 show graphical user interface (GUI) outputs of the probability of birth that day, after a session of a predetermined time interval. In each case, the user's input information such as due date, number of babies that the user is carrying, a date of birth of the user, a height of the user, a weight of the user, a background or demographic (e.g., ethnicity, education level, use of Medicaid, and a number of pregnancies that the user had previously) of the user, one or more previous pregnancies of the user, for example a timeline of a previous pregnancy (e.g., date of delivery, date of conception, number of months between delivery and conception, etc.), a type of delivery (i.e., vaginal or C-section), a number of previous pregnancies, a number of current children, a number of previous pre-term deliveries, etc., risk factors of the user, for example hypertension pre-pregnancy, diabetes pre-pregnancy, gestational diabetes, gestational hypertension, preeclampsia, eclampsia, receipt of infertility treatments, etc., a lifestyle of the user, for example smoking frequency, activity level pre-pregnancy, activity level during pregnancy, stressfulness of lifestyle, an alcohol consumption metric, a recreational drug use frequency, a coitus frequency, an eating frequency and/or quality, a frequency of traveling, etc., the detected EHG and HR and the detected artifacts are combined to display a probability of birth.

Figure 35:
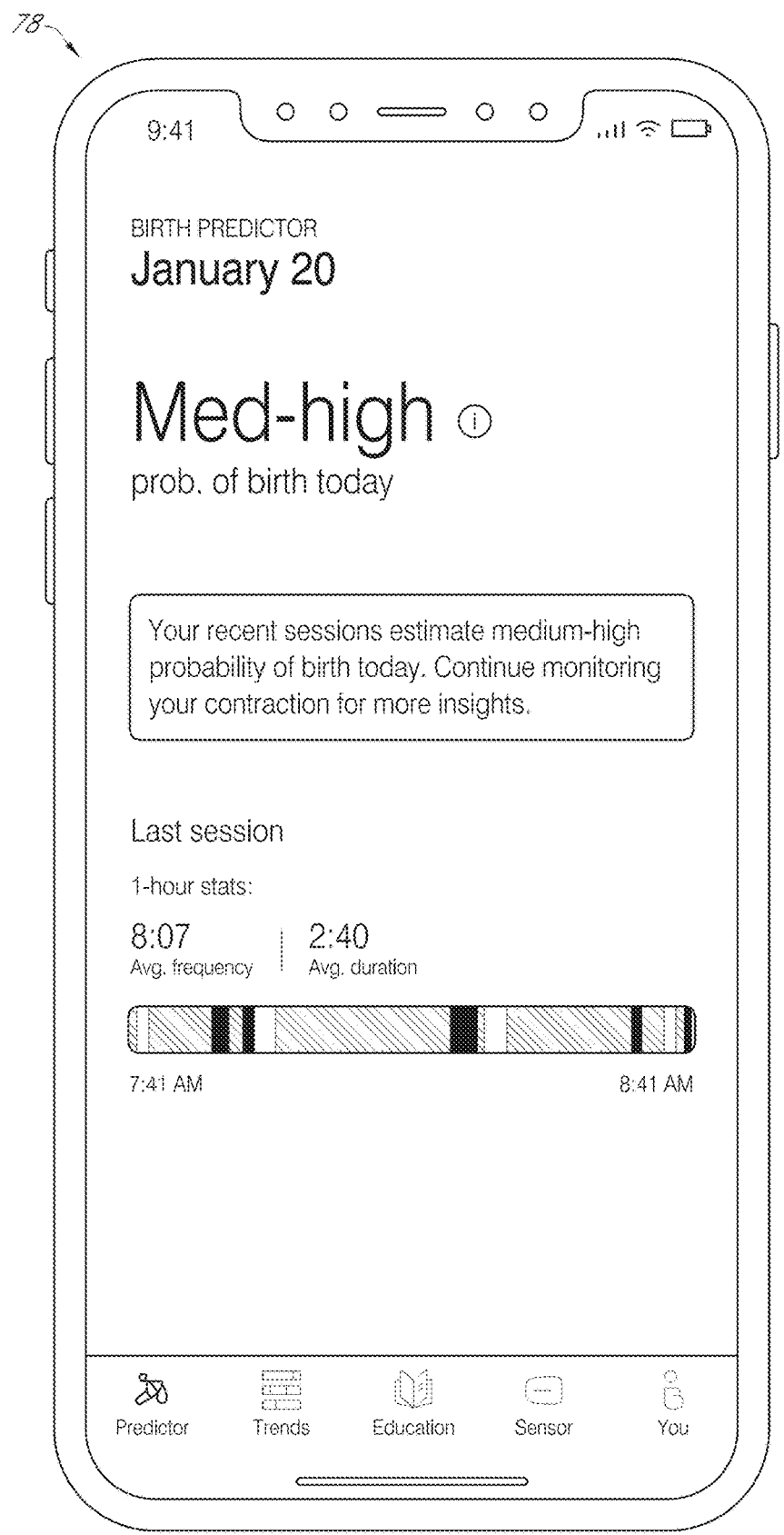
FIG. 35 illustrates one embodiment of a graphical user interface for displaying the probability of birth based, at least in part, on a monitoring session.

As shown in FIG. 35, GUI 78 may display the combined data inputted by the user and the EHG and HR, after removal of artifacts detected by the sensor, as a probability of birth on a given day, for example a med-high probability of birth. In some embodiments, the system has determined that the probability of birth is between 0% to 35% for low risk, 36% to 70% for medium risk, and 71% to 100% for high risk or any range or subrange therebetween. In some embodiments, these ranges are adjustable depending on the mom's risk profile, by the mom herself, or by the care team or health provider.

The length of the session may be displayed on the GUI, along with the average frequency of contractions and the average duration of the contraction. The GUI further displays the time the session started and the ending time of the session, therefore, giving the time window of the session, e.g., 10 minutes.

Figure 36:
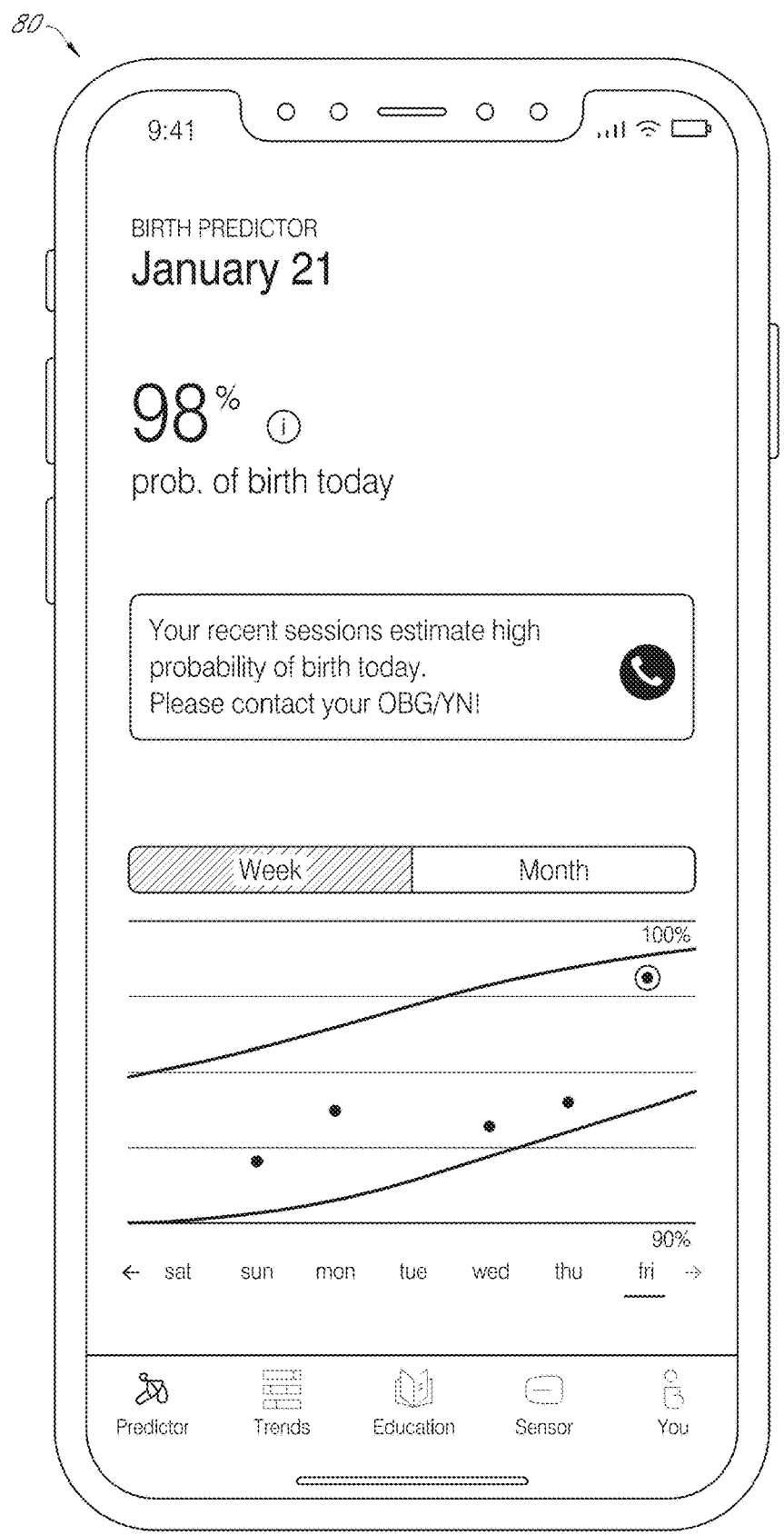
FIG. 36 illustrates one embodiment of a graphical user interface for displaying the probability of birth based, at least in part, on a monitoring session.

As shown in FIG. 36, GUI 86 may display the combined data inputted by the user and the EHG and HR, after removal of artifacts detected by the sensor, a probability of birth on a given day, for example a percentage, e.g., 98%. The GUI may display the level of probability, i.e. low, medium, med-high, or high and display an alert, for example to contact a health provider. Along with the described display features, GUI 86 may display multiple sessions across a determined time frame, e.g., week or month, and a graph that outlines a decrease, increase, or no change in probability, based on each session across the determined time frame.

Figure 37:
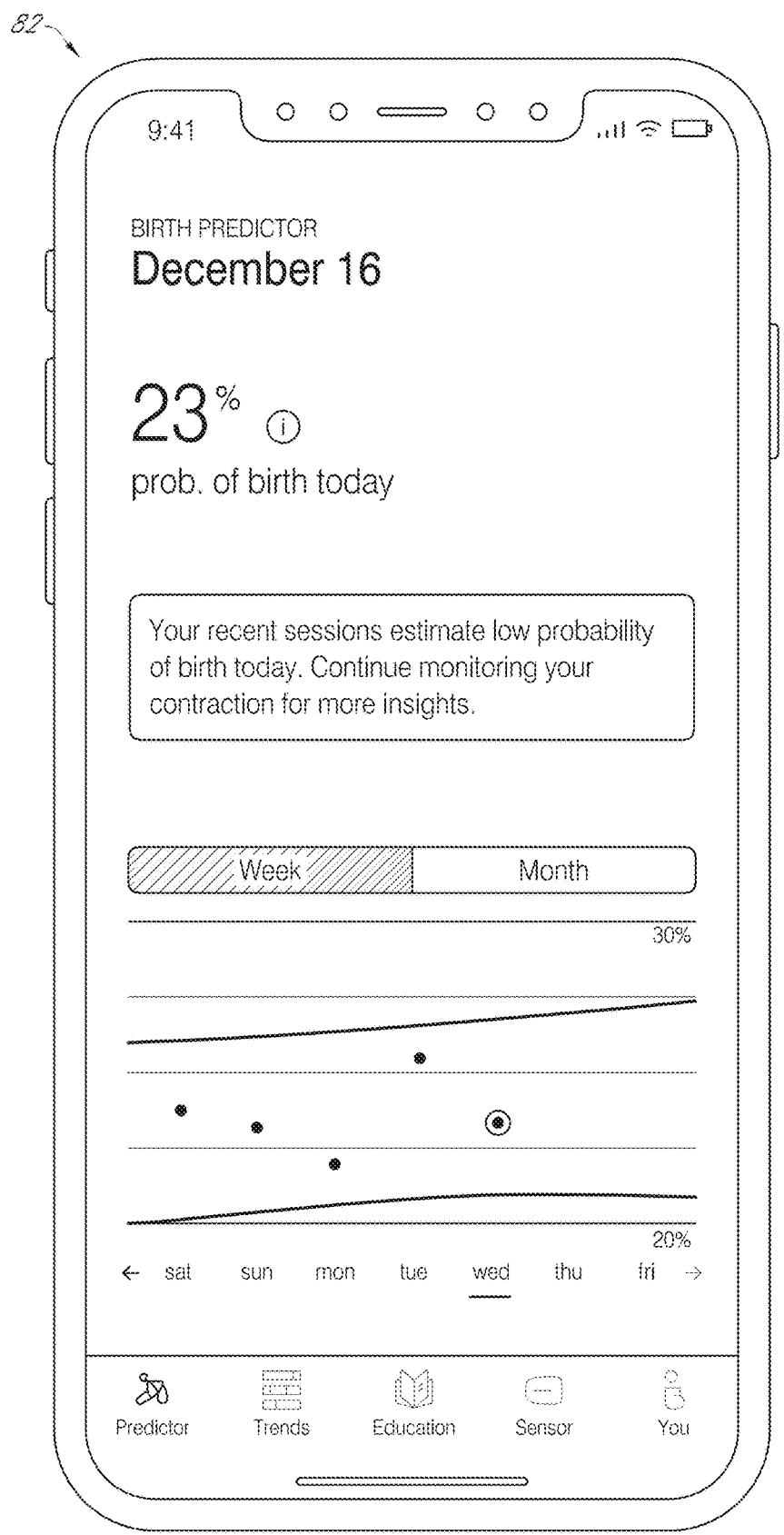
FIG. 37 illustrates one embodiment of a graphical user interface for displaying the probability of birth based, at least in part, on a monitoring session.
Figure 38:
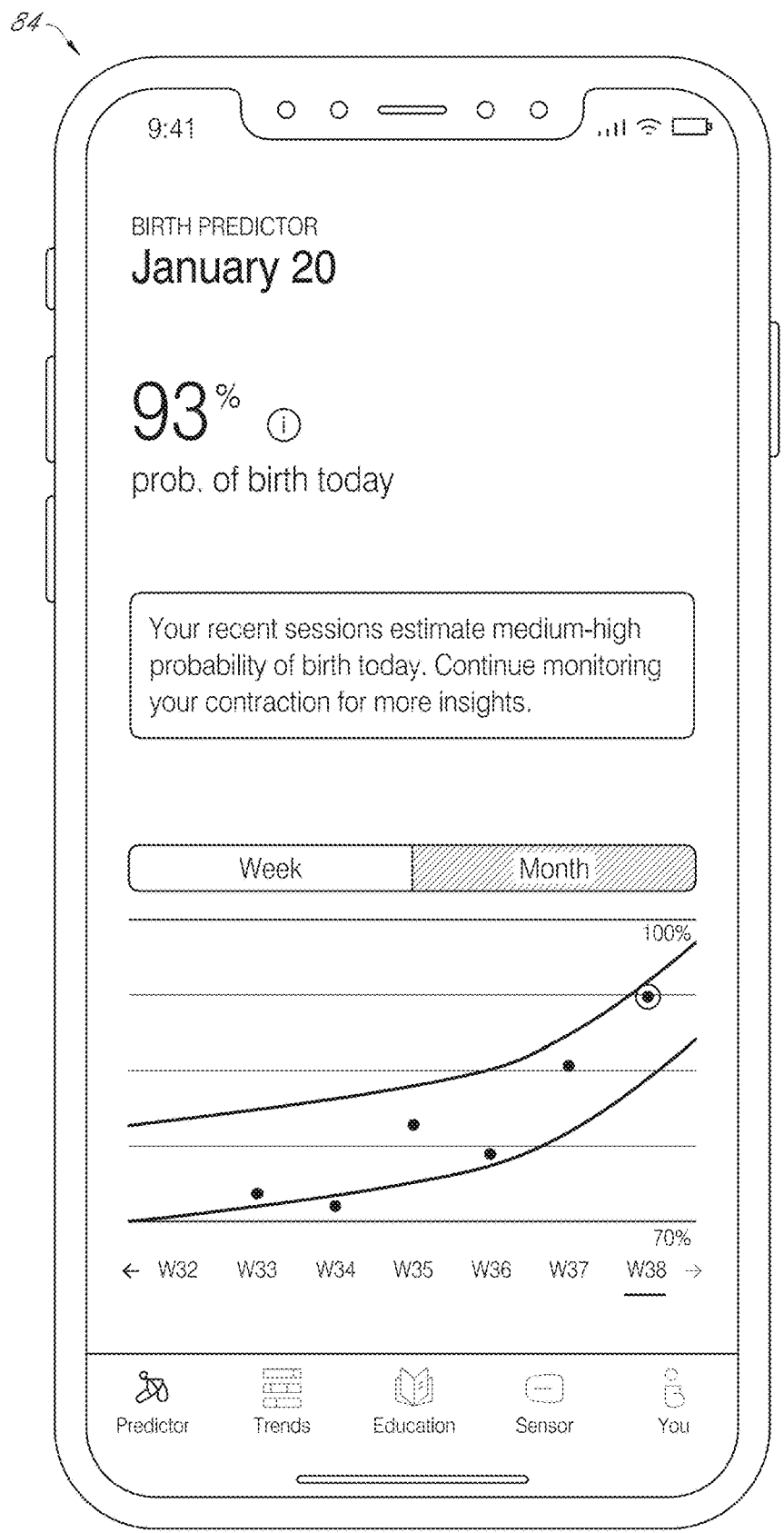
FIG. 38 illustrates one embodiment of a graphical user interface for displaying the probability of birth based, at least in part, on a monitoring session.

As shown in FIGS. 37-38, GUIs 82, 84 may display the combined data inputted by the user and the EHG and HR, after removal of artifacts detected by the sensor, a probability of birth on a given day, for example a probability percentage, e.g., 23% or 93%, respectively. GUIs 37-38 may display a level of probability, e.g., low, medium, med-high, or high and an alert, e.g., to contact a health provider. Along with the described display features, the GUI may display multiple sessions across a determined time frame, e.g., week or month, and a graph that outlines a decrease, increase, or no change in probability, based on each session across the determined time frame.

Figure 39:
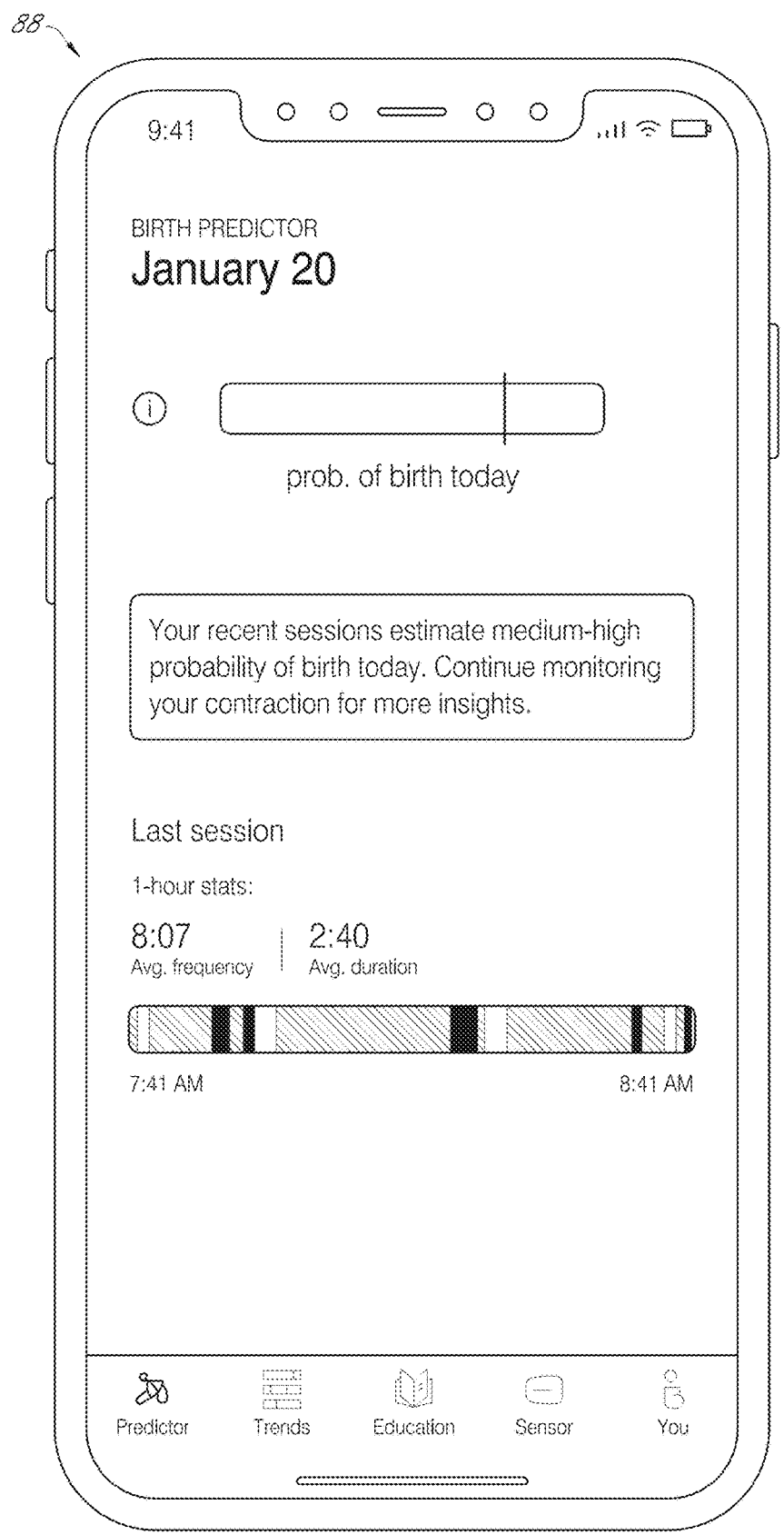
FIG. 39 illustrates one embodiment of a graphical user interface for displaying the probability of birth based, at least in part, on a monitoring session.

As shown in FIG. 39, GUI 88 may display the combined data inputted by the user the EHG and HR, after removal of artifacts detected by the sensor, a probability of birth on a given day, for example a med-high probability. The length of the session may be displayed on the GUI, along with the average frequency of contractions and the average duration of the contraction. In some embodiments, the GUI further displays the time the session started and the ending time of the session, therefore, giving the time window of the session, e.g., 10 minutes.

In one non-limiting example, the system may use heart rate, heart rate variability, and/or Galvanic skin response parameters to calculate a stress level of the pregnant female.

In another non-limiting example, the system may use one or more acceleration parameters (e.g., using an accelerometer) to calculate a sleep quality, activity level, and/or calorie expenditure of the pregnant female.

In another non-limiting example, the system may use one or more electrohysterography parameters to calculate uterine activity (e.g., labor contractions, Braxton-Hicks contractions, etc.) of the pregnant female.

In another non-limiting example, the system may use a blood oxygen saturation parameter (e.g., photoplethysmography) and one or more acceleration parameters to calculate a cardiorespiratory fitness level of the pregnant female.

In another non-limiting embodiment, the system may use one or more electrocardiogram parameters to calculate a heart rate or heart rate variability of the pregnant female and/or one or more fetuses she is carrying.

In another non-limiting example, the system may use one or more acceleration parameters (e.g., using an accelerometer) to calculate an activity level of a fetus.

In some embodiments, the method 800 includes: displaying the behavioral parameter to a user, for example the pregnant female. For example, a GUI of the system may be configured to display one or more behavioral parameters graphically, schematically, haptically, using text, audio, or using any visual, audible, or tactile display means.

Figure 34:
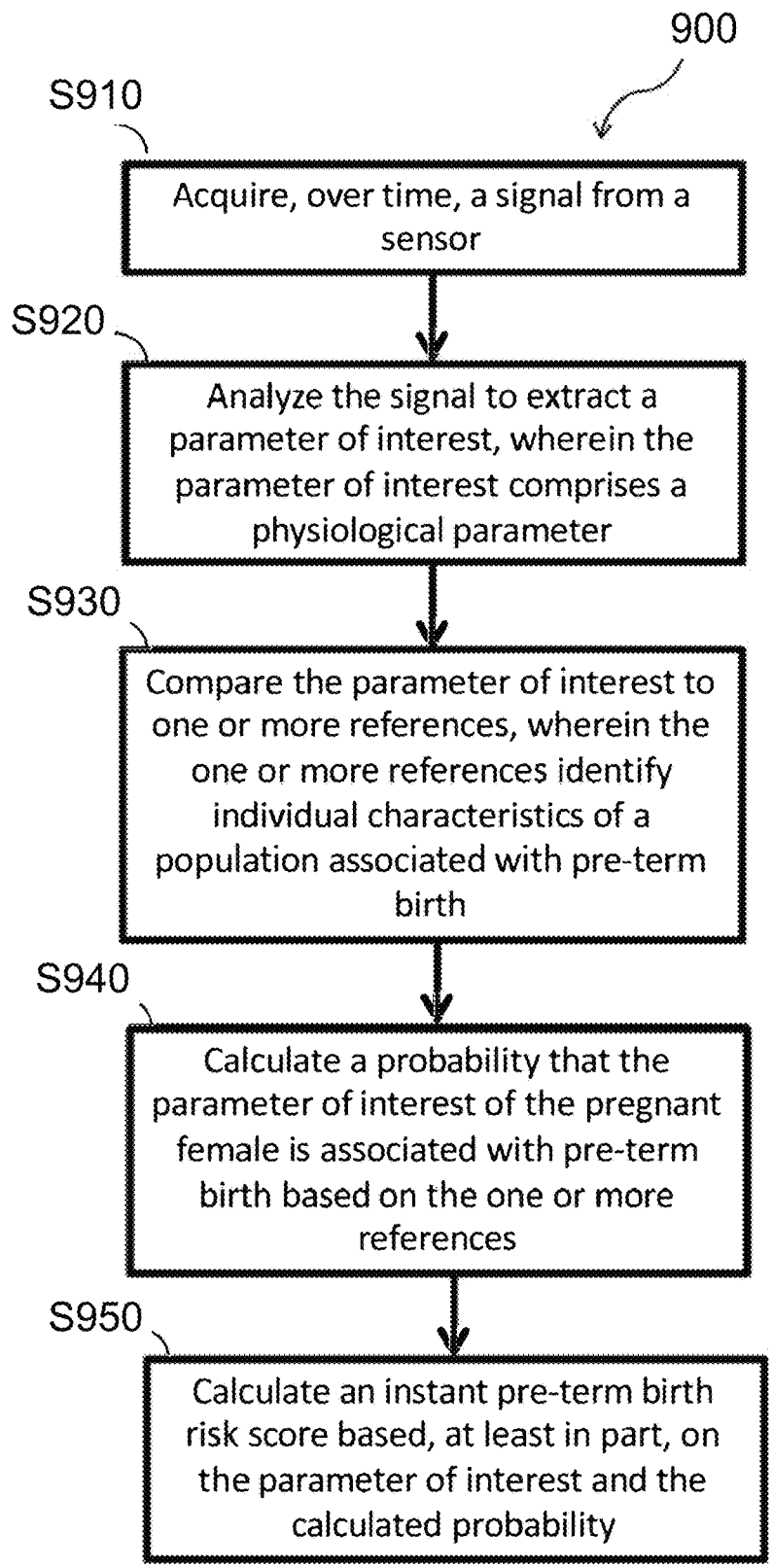
FIG. 34 illustrates a flow chart of one embodiment of a method of assessing a pre-term birth risk.

As shown in FIG. 34, one embodiment of a method 900 for assessing over time a pre-term birth risk of a pregnant female includes acquiring, over time, a signal from a sensor S510; analyzing the signal to extract a parameter of interest, wherein the parameter of interest comprises a physiological parameter S920; comparing the parameters of interest to one or more references, wherein the one or more references identify individual characteristics of a population associated with pre-term birth S930; calculating a probability that the parameter of interest of the pregnant female is associated with pre-term birth based on the one or more references S940; and calculating an instant pre-term birth risk score based, at least in part, on the parameter of interest and the calculated probability. The method 900 functions to compare one or more features, characteristics, or conditions of the pregnant female to one or more populations to improve or enhance a calculation of her pre-term birth risk score.

In some embodiments, the one or more references include one or more of: a database, a publication, a presentation, and a website. The one or more references may be derived from data from a health department, government agency, crowd-sourced data (e.g., users using the system described herein or other systems), a clinical trial, a scientific study, a retrospective study, or another source.

In some variations, analyzing the deviation is performed by a machine learning algorithm. Machine learning algorithms identify patterns, employ computational learning (e.g., learning without being explicitly programmed), and make predictions on data, for example personalized data, community data, and/or population-level data. Non-limiting examples of machine learning algorithms include a generalized linear model, support vector machines, and random forests.

As used in the description and claims, the singular form "a", "an" and "the" include both singular and plural references unless the context clearly dictates otherwise. For example, the term "sensor" may include, and is contemplated to include, a plurality of sensors. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

In the block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, notwithstanding use of the singular term "medium," the instructions may be distributed on different storage devices associated with different computing devices, for instance, with each computing device having a different subset of the instructions, an implementation consistent with usage of the singular term "medium" herein. In some cases, third party content delivery networks may host some or all of the information conveyed over networks, in which case, to the extent information (e.g., content) is said to be supplied or otherwise provided, the information may be provided by sending instructions to retrieve that information from a content delivery network.

The reader should appreciate that the present application describes several independently useful techniques. Rather than separating those techniques into multiple isolated patent applications, applicants have grouped these techniques into a single document because their related subject matter lends itself to economics in the application process. But the distinct advantages and aspects of such techniques should not be conflated. In some cases, embodiments address all of the deficiencies noted herein, but it should be understood that the techniques are independently useful, and some embodiments address only a subset of such problems or offer other, unmentioned benefits that will be apparent to those of skill in the art reviewing the present disclosure. Due to cost constraints, some techniques disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such techniques or all aspects of such techniques.

It should be understood that the description and the drawings are not intended to limit the present techniques to the particular form disclosed, but to the contrary, the intention is to cover all modifications, equivalents, and alternatives falling within the spirit and scope of the present techniques as defined by the appended claims. Further modifications and alternative embodiments of various aspects of the techniques will be apparent to those skilled in the art in view of this description. Accordingly, this description and the drawings are to be construed as illustrative only and are for the purpose of teaching those skilled in the art the general manner of carrying out the present techniques. It is to be understood that the forms of the present techniques shown and described herein are to be taken as examples of embodiments. Elements and materials may be substituted for those illustrated and described herein, parts and processes may be reversed or omitted, and certain features of the present techniques may be utilized independently, all as would be apparent to one skilled in the art after having the benefit of this description of the present techniques. Changes may be made in the elements described herein without departing from the spirit and scope of the present techniques as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include, "including", and "includes" and the like meaning including, but not limited to. As used throughout this application, the singular forms "a", "an", and "the" include plural referents unless the content explicitly indicates otherwise. Thus, for example, reference to "an element" or "a element" includes a combination of two or more elements, notwithstanding use of other terms and phrases for one or more elements, such as "one or more". The term "or" is, unless indicated otherwise, non-exclusive, i.e., encompassing both "and" and "or". Terms describing conditional relationships, e.g., "in response to X, Y," "upon X, Y," "if X, Y," "when X, Y," and the like, encompass casual relationships in which the antecedent is a necessary casual condition, the antecedent is a sufficient casual condition, or the antecedent is a contributory casual condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "as least Z of A, B, and C," and the like (e.g., "at least Z of A, B, or C"), refer to at least Z of the listed categories (A, B, and C_ and do not require at least Z units in each category. Unless specifically stated otherwise, as apparent from the discussion, it is appreciated that through this specification discussions utilizing terms such as "processing," "computing," "calculating," "determining" or the like refer to actions or processes of a specific apparatus, such as a special purpose computer or a similar special purpose electronic processing/computing device.

As used herein, the term "comprising" or "comprises" is intended to mean that the systems and methods include the recited elements, and may additionally include any other elements. "Consisting essentially of" shall mean that the systems and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed invention. "Consisting of" shall mean that the systems and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The present technique will be better understood with reference to the following enumerated embodiments:

1. A system for uterine activity monitoring, the system comprising: a plurality of sensors coupled to a belly region of a pregnant female; a processor communicatively coupled to the plurality of sensors; and a computer-readable medium having non-transitory, processor-executable instructions stored thereon, wherein execution of the instructions causes the processor to perform a method comprising: acquiring a plurality of signals from the plurality of sensors during uterine activity, processing the plurality of signals to extract a plurality of uterine electrical activity characteristics, analyzing the plurality of uterine electrical activity characteristics, and classifying the uterine activity as one of: a preterm labor contraction, a labor contraction, a Braxton-Hicks contraction, and a state of no contraction, based at least in part on the plurality of uterine electrical activity characteristics.

2. The system of embodiment 1, wherein the plurality of uterine electrical activity characteristics includes at least two of: a uterine electrical activity frequency, a uterine electrical activity amplitude over time, a uterine electrical activity duration over time, a directionality of uterine electrical activity, and a velocity of uterine electrical activity.

3. The system of any one of embodiments 1-2, wherein the directionality or velocity of uterine electrical activity is determined by sensing a uterine electrical activity movement or propagation over time between at least three sensors.

4. The system of any one of embodiments 1-3, wherein analyzing the plurality of uterine electrical activity characteristics is performed using machine learning techniques.
5. The system of any one of embodiments 1-4, wherein the method performed by the processor further comprises: processing the plurality of signals to extract a maternal characteristic during the uterine activity; and correlating the maternal characteristic with the plurality of uterine electrical activity characteristics, wherein the uterine activity is classified as one of: a preterm labor contraction, a labor contraction, a Braxton-Hicks contraction, or a state of no contraction, based at least in part on the plurality of uterine electrical activity characteristics and the maternal characteristic.
6. The system of embodiment 5, wherein the maternal characteristic includes one or more of: a maternal heart rate, a maternal heart rate variability, a maternal respiration rate, a maternal respiration intensity, a maternal galvanic skin response, and a maternal skin or body temperature.
7. The system of any one of embodiments 5-6, wherein the method performed by the processor further comprises: analyzing the plurality of uterine electrical activity characteristics over time to identify one or more changes; and correlating the maternal characteristic with the one or more changes in the plurality of uterine electrical activity characteristics.
8. The system of any one of embodiments 1-7, wherein the method performed by the processor further comprises: processing the plurality of signals to extract a deformation of the belly region of the pregnant female; and correlating the deformation of the belly region with the plurality of uterine electrical activity characteristics, wherein the uterine activity is classified as one of: a preterm labor contraction, a labor contraction, a Braxton-Hicks contraction, and a state of no contraction, based at least in part on the plurality of uterine electrical activity characteristics and the deformation of the belly region.
9. The system of embodiment 8, wherein the deformation of the belly region is measured by one of: an inertial sensor, a piezo-electric sensor, a piezo-resistive sensor, a capacitive sensor, a pressure sensor, and a stretch sensor.
10. The system of embodiment 8, wherein the method performed by the processor further includes: analyzing the plurality of uterine electrical activity characteristics over time to identify one or more changes; and correlating the deformation of the belly region with one or more changes in the plurality of uterine electrical activity characteristics.
11. The system of any one of embodiments 1-10, wherein the plurality of sensors is coupled to a wearable accessory.
12. The system of any one of embodiments 1-11, wherein the wearable accessory is one of: a belly patch and a belly belt.
13. The system of any one of embodiments 1-12, wherein the plurality of sensors is positioned on or in a portable and wearable sensor module, the sensor module further comprising an electronic circuit and a wireless antenna, and wherein the sensor module is in wireless communication with a computing device comprising the processor and the computer-readable medium.
14. The system of embodiment 13, wherein the computing device is a mobile computing device.
15. The system of embodiments 13-14, wherein the mobile computing device is selected from a group consisting of: a smartphone, a smart watch, smart glasses, smart contact lenses, other wearable computer, a tablet, a laptop, and a personal computer.
16. The system of any one of embodiments 1-15, wherein the method performed by the processor further comprises: generating an alert.
17. The system of any one of embodiments 1-16, wherein the method performed by the processor further comprises: notifying a user of the uterine activity or a classification of the uterine activity as one of: the preterm labor contraction, the labor contraction, the Braxton-Hicks contraction, and the state of no contraction.
18. The system of any one of embodiments 1-17, wherein the method performed by the processor further comprises: recommending a course of action to a user based on the detected uterine activity and a classification of the uterine activity.
19. The system of any one of embodiments 1-18, wherein the user is one or more of: a partner, the pregnant female, a healthcare provider, a doula, a midwife, a friend, a family member, an emergency service provider, and a transportation service provider.
20. The system of any one of embodiments 1-19, wherein the method performed by the processor further comprises: determining a probability that the pregnant female is experiencing one of: preterm labor contractions, term labor contractions, Braxton-Hicks contractions, and no contractions.
21. The system of embodiment 20, wherein the method performed by the processor further comprises: determining a degree of certainty around the determined probability.
22. The system of any one of embodiments 1-21, wherein the method performed by the processor further comprises: displaying on a computing device communicatively coupled to the processor a visual representation of the uterine activity or a series of uterine activities.
23. A system for uterine activity monitoring, the system comprising: a plurality of sensors coupled to a belly region of a pregnant female; a processor communicatively coupled to the plurality of sensors; and a computer-readable medium having non-transitory, processor-executable instructions stored thereon, wherein execution of the instructions causes the processor to perform a method comprising: acquiring a plurality of signals from the plurality of sensors during a series of uterine activities, processing the plurality of signals to extract a plurality of uterine electrical activity characteristics of the series of uterine activities, analyzing the plurality of uterine electrical activity characteristics of the series of uterine activities to identify a pattern, and classifying the pattern as one of: a preterm labor contraction, a labor contraction, a Braxton-Hicks contraction, and a state of no contraction.
24. The system of embodiment 23, wherein the pattern of the plurality of uterine electrical activity characteristics includes at least one of: a time interval between uterine electrical activities, a change in uterine electrical activity frequency, a change in uterine electrical activity amplitude, a change in uterine electrical activity duration, a change in uterine electrical activity directionality, and a change in uterine electrical activity velocity.
25. The system of any one of embodiments 23-24, wherein the method performed by the processor further comprises: processing the plurality of signals to extract a maternal characteristic during, in-between, before, or after the series of uterine activities; and correlating the maternal characteristic with the plurality of uterine electrical activity characteristics, wherein the uterine activity is classified as one of: a preterm labor contraction, a labor contraction, a Braxton-Hicks contraction, and a state of no contraction, based at least in part on the plurality of uterine electrical activity characteristics and the maternal characteristic.

26. A method of uterine activity monitoring, the method comprising: acquiring a plurality of signals from a plurality of sensors during uterine activity, wherein the plurality of sensors is coupled to a belly region of a pregnant female; processing the plurality of signals to extract a plurality of uterine electrical activity characteristics; analyzing the plurality of uterine electrical activity characteristics; and classifying the uterine activity as one of: a preterm labor contraction, a labor contraction, a Braxton-Hicks contraction, and a state of no contraction, based at least in part on the plurality of uterine electrical activity characteristics.

27. The method of embodiment 26, further comprising: processing the plurality of signals to extract a maternal characteristic during, before, or after the uterine activity.

28. The method of any one of embodiments 26-27, further comprising: correlating the maternal characteristic with the plurality of uterine electrical activity characteristics to identify the uterine activity as one of: a preterm labor contraction, a labor contraction, a Braxton-Hicks contraction, and a state of no contraction.

29. The method of any one of embodiments 27-28, further comprising: analyzing the plurality of uterine electrical activity characteristics over time to identify one or more changes; and correlating the maternal characteristic with the one or more changes in the plurality of uterine electrical activity characteristics.

30. The method of any one of embodiments 27-29, wherein the maternal characteristic includes one or more of: a maternal heart rate, a maternal heart rate variability, a maternal respiration rate, a maternal respiration intensity, a maternal galvanic skin response, and a maternal skin or body temperature.

31. The method of any one of embodiments 26-30, wherein the plurality of uterine electrical activity characteristics includes at least two of: a uterine electrical activity frequency, a uterine electrical activity amplitude over time, a uterine electrical activity duration over time, a directionality of uterine electrical activity, and a velocity of uterine electrical activity.

32. The method of any one of embodiments 26-31, further comprising: processing the plurality of signals to extract a deformation of the belly region of the pregnant female.

33. The method of embodiment 32, further comprising: analyzing the plurality of uterine electrical activity characteristics over time to identify one or more changes; and correlating the deformation of the belly region with one or more changes in the plurality of uterine electrical activity characteristics.

34. The method of any one of embodiments 26-33, wherein the uterine activity comprises a series of uterine activities.

35. The method of embodiment 34, further comprising analyzing the plurality of uterine electrical activity characteristics of the series of uterine activities to identify a pattern, and classifying the pattern as one of: a preterm labor contraction, a labor contraction, a Braxton-Hicks contraction, and a state of no contraction.

36. A system for assessing over time a pre-term birth risk of a pregnant female, the system comprising a sensor configured to be worn on a belly region of the pregnant female; a processor communicatively coupled to the sensor; and a computer-readable medium having non-transitory, processor-executable instructions stored thereon, wherein execution of the instructions causes the processor to perform a method comprising: calculating a baseline pre-term birth risk score based on a user input; acquiring, over time, a signal from a sensor; analyzing the signal to extract a parameter of interest, wherein the parameter of interest comprises a physiological parameter; and calculating an instant pre-term birth risk score based, at least in part, on the parameter of interest and the user input.

37. The system of embodiment 36, further comprising a computing device communicatively coupled to the processor, wherein the method performed by the processor further comprises: receiving the user input with the computing device.

38. The system of embodiment 37, wherein the computing device is one of: a laptop, a desktop, a netbook, a notebook, a mobile device, a personal digital assistant, a smart phone, a smart watch, and a wearable device.

39. The system of any one of embodiments 36-38, further comprising an antenna, wherein the antenna functions as a receiver to receive the user input from a computing device communicatively coupled to the processor.

40. The system of any one of embodiments 36-38, further comprising an antenna, wherein the antenna functions as a transmitter to transmit one or more of the baseline pre-term birth risk score and the instant pre-term birth risk score to a computing device communicatively coupled to the system.

41. The system of any one of embodiments 36-38, wherein the method performed by the processor further comprises: receiving the user input, wherein the user input comprises of one or more of: a health history of the pregnant female, one or more demographics of the pregnant female, a lifestyle of the pregnant female, and a number of fetuses being carried by the pregnant female.

42. The system of embodiment 41, wherein the lifestyle of the pregnant female comprises one or more of: an exercise schedule of the pregnant female, a medical drug regimen of the pregnant female, an alcohol consumption metric of the pregnant female, a smoking habit of the pregnant female, a recreational drug use habit of the pregnant female, a coitus schedule of the pregnant female, an eating habit of the pregnant female, and a frequency of traveling of the pregnant female.

43. The system of any one of embodiments 36-42, wherein the method performed by the processor further comprises: providing a recommendation to the pregnant female to maintain or improve the instant pre-term birth risk score.

44. The system of embodiment 43, wherein the recommendation comprises one or more of: a change in an activity level, reduce or stop smoking, reduce or stop alcohol consumption, increase an amount of rest, decrease a stress level, drink more water, increase an amount of sleep, increase an amount of healthy foods consumed, reduce or stop drug use, a change in caloric intake, and a change in a medication regimen.

45. The system of any one of embodiments 36-44, wherein the method performed by the processor further comprises: providing one or more of: the baseline pre-term birth risk score and the instant pre-term birth risk score to a healthcare provider.

46. The system of embodiment 45, wherein the method performed by the processor further comprises: categorizing a group of pregnant females according to one or more of: their baseline pre-term birth risk score and their instant pre-term birth risk score.

47. The system of any one of embodiments 45-46, wherein the method performed by the processor further comprises: varying a treatment based on one or more of: the baseline pre-term birth risk score and the instant pre-term birth risk score.

48. The system of any one of embodiments 45-47, wherein the method performed by the processor further comprises: adapting prenatal care based on one or more of: the baseline pre-term birth risk score and the instant pre-term birth risk score.

49. The system of any one of embodiments 36-48, wherein the method performed by the processor further comprises: receiving a biological data input; and calculating the instant pre-term birth risk score based, at least in part, on the biological data input.

50. The system of embodiment 49, wherein the biological data input comprises one or more of: a biological test result, a blood test result, an ultrasound screening result, a vaccination record, proteomics data, genetic data, serum test results, and an amniocentesis result.

51. The system of any one of embodiments 36-50, wherein calculating comprises using Bayesian linear regression.

52. The system of any one of embodiments 36-51, wherein calculating is performed using machine learning techniques.

53. The system of any one of embodiments 36-52, wherein the physiological parameters comprise one or more of: a contraction wave amplitude, a contraction wave frequency over time, a directionality of a contraction wave, a velocity of contraction wave propagation, a contraction wave duration over time, a resting heart rate, a resting heart rate variability, a blood pressure level, a blood glucose level, an oxygen saturation level, a weight, a heartbeat of a fetus, a heart rate of a fetus, a heart rate variability of a fetus, a position of a fetus, and a weight of a fetus.

54. The system of any one of embodiments 36-53, wherein the method performed by the processor further comprises: comparing the parameter of interest to one or more references, wherein the one or more references identify individual characteristics of a population associated with pre-term birth; calculating a probability that the parameter of interest of the pregnant female is associated with pre-term birth based on the one or more references; and calculating the instant pre-term birth risk score based, at least in part, on the calculated probability.

55. The system of embodiment 54, wherein the one or more references include one or more of: a database, a publication, a presentation, and a website.

56. The system of any one of embodiments 36-55, wherein the method performed by the processor further comprises: displaying one or more of: the baseline pre-term birth risk score and the instant pre-term birth risk score to the pregnant female or another user.

57. The system of embodiment 56, wherein the method performed by the processor further comprises: displaying a series of factors that influence one or more of: the baseline pre-term birth risk score and the instant pre-term birth risk score to the pregnant female.

58. The system of any one of embodiments 36-57, wherein the signal comprises a plurality of signals.

59. The system of any one of embodiments 36-58, wherein the sensor comprises a plurality of sensors.

60. The system of any one of embodiments 36-59, wherein the parameter of interest comprises a plurality of parameters of interest.

61. The system of any one of embodiments 36-60, wherein the physiological parameters comprise a plurality of physiological parameters.

62. The system of any one of embodiments 36-61, wherein the method performed by the processor further comprises: determining a behavioral parameter based one or more physiological parameters; calculating the instant pre-term birth risk score based, at least in part, on the behavioral parameter.

63. The system of embodiment 62, wherein the behavioral parameter comprises one or more of: a stress level of the pregnant female, a sleep quality of the pregnant female, an activity level of the pregnant female, a calorie expenditure of the pregnant female, a cardiorespiratory fitness level of the pregnant female, an activity level of a fetus, and a wellbeing of a fetus.

64. The system of any one of embodiments 62-63, wherein the method performed by the processor further comprises: displaying the behavioral parameter to the pregnant female or another user.

65. The system of any one of embodiments 36-64, wherein the method performed by the processor further comprises: when the instant pre-term birth risk score differs from the baseline pre-term birth risk score, updating the baseline pre-term birth risk score with the instant pre-term birth risk score.

66. The system of any one of embodiments 36-65, further comprising a patch or belt coupled to the sensor and configured to position the sensor against a skin surface of the belly region of the pregnant female.

67. A method of assessing over time a pre-term birth risk of a pregnant female, the method comprising: calculating a baseline pre-term birth risk score based on a user input; acquiring, over time, a signal from a sensor; analyzing the signal to extract a parameter of interest, wherein the parameter of interest comprises a physiological parameter; and calculating an instant pre-term birth risk score based, at least in part, on the parameter of interest and the user input.

68. The method of embodiment 67, further comprising: receiving the user input, wherein the user input comprises of one or more of: a health history of the pregnant female, one or more demographics of the pregnant female, a lifestyle of the pregnant female, and a number of fetuses being carried by the pregnant female.

69. The method of any one of embodiments 67-68, wherein the lifestyle of the pregnant female comprises one or more of: an exercise schedule of the pregnant female, a medical drug regimen of the pregnant female, an alcohol consumption metric of the pregnant female, a smoking habit of the pregnant female, a recreational drug use habit of the pregnant female, a coitus schedule of the pregnant female, an eating habit of the pregnant female, and a frequency of traveling of the pregnant female.

70. The method of any one of embodiments 67-69, further comprising: providing a recommendation to the pregnant female to maintain or improve the instant pre-term birth risk score.

71. The method of embodiment 70, wherein the recommendation comprises one or more of: a change in an activity level, reduce or stop smoking, reduce or stop alcohol consumption, increase an amount of rest, decrease a stress level, drink more water, increase an amount of sleep, increase an amount of healthy foods consumed, reduce or stop drug use, a change in caloric intake, and a change in a medication regimen.

72. The method of any one of embodiments 67-71, further comprising: providing one or more of: the baseline pre-term birth risk score and the instant pre-term birth risk score to a healthcare provider.
73. The method of embodiment 72, further comprising: categorizing a group of pregnant females according to one or more of: their baseline pre-term birth risk score and their instant pre-term birth risk score.
74. The method of any one of embodiments 72-73, further comprising: varying a treatment based on one or more of: the baseline pre-term birth risk score and the instant pre-term birth risk score.
75. The method of any one of embodiments 72-74, further comprising: adapting prenatal care based on one or more of: the baseline pre-term birth risk score and the instant pre-term birth risk score.
76. The method of any one of embodiments 67-75, further comprising: receiving a biological data input; and calculating the instant pre-term birth risk score based, at least in part, on the biological data input.
77. The method of embodiment 76, wherein the biological data input comprises one or more of: a biological test result, a blood test result, an ultrasound screening result, a vaccination record, proteomics data, genetic data, serum test results, and an amniocentesis result.
78. The method of any one of embodiments 67-77, wherein calculating comprises using Bayesian linear regression.
79. The method of any one of embodiments 67-78, wherein calculating is performed using machine learning techniques.
80. The method of any one of embodiments 67-79, wherein the physiological parameters comprise one or more of: a contraction wave amplitude, a contraction wave frequency over time, a directionality of a contraction wave, a velocity of contraction wave propagation, a contraction wave duration over time, a resting heart rate, a resting heart rate variability, a blood pressure level, a blood glucose level, an oxygen saturation level, a weight, a heartbeat of a fetus, a heart rate of a fetus, a heart rate variability of a fetus, a position of a fetus, and a weight of a fetus.
81. The method of any one of embodiments 67-80, further comprising: comparing the parameter of interest to one or more references, wherein the one or more references identify individual characteristics of a population associated with pre-term birth; calculating a probability that the parameter of interest of the pregnant female is associated with pre-term birth based on the one or more references; and calculating the instant pre-term birth risk score based, at least in part, on the calculated probability.
82. The method of embodiment 81, wherein the one or more references include one or more of: a database, a publication, a presentation, and a website.
83. The method of any one of embodiments 67-82, further comprising: displaying one or more of: the baseline pre-term birth risk score and the instant pre-term birth risk score to the pregnant female or another user.
84. The method of embodiment 83, further comprising: displaying a series of factors that influence one or more of: the baseline pre-term birth risk score and the instant pre-term birth risk score to the pregnant female.
85. The method of any one of embodiments 67-84, wherein the signal comprises a plurality of signals.
86. The method of any one of embodiments 67-85, wherein the sensor comprises a plurality of sensors.
87. The method of any one of embodiments 67-86, wherein the parameter of interest comprises a plurality of parameters of interest.
88. The method of any one of embodiments 67-87, wherein the physiological parameters comprise a plurality of physiological parameters.
89. The method of any one of embodiments 67-88, further comprising: determining a behavioral parameter based one or more physiological parameters; calculating the instant pre-term birth risk score based, at least in part, on the behavioral parameter.
90. The method of embodiment 89, wherein the behavioral parameter comprises one or more of: a stress level of the pregnant female, a sleep quality of the pregnant female, an activity level of the pregnant female, a calorie expenditure of the pregnant female, a cardiorespiratory fitness level of the pregnant female, an activity level of a fetus, and a wellbeing of a fetus.
91. The method of any one of embodiments 89-90, further comprising: displaying the behavioral parameter to the pregnant female or another user.
92. The method of any one of embodiments 67-91, further comprising: when the instant pre-term birth risk score differs from the baseline pre-term birth risk score, updating the baseline pre-term birth risk score with the instant pre-term birth risk score.
93. A system for assessing over time a pre-term birth risk of a pregnant female, the system comprising: a first sensor configured to be worn on a belly region of the pregnant female; a second sensor coupled to or housed within a health monitoring device; a processor communicatively coupled to the first and second sensors; and a computer-readable medium having non-transitory, processor-executable instructions stored thereon, wherein execution of the instructions causes the processor to perform a method comprising: acquiring, over time, a first signal from the first sensor and a second signal from the second sensor; analyzing the first and second signals to extract one or more parameters of interest, wherein the one or more parameters of interest comprise one or more physiological parameters; and calculating an instant pre-term birth risk score based, at least in part, on the one or more parameters of interest.
94. The system of embodiment 93, wherein the health monitoring device is one of: an activity tracker, a weight scale, a blood pressure monitor, a blood glucose monitor, a thermometer, and a pacemaker.

What is claimed is:
1. A non-invasive system for assessing over time a pre-term birth risk of a pregnant female, the system comprising:
a sensor configured to be worn on a belly region of the pregnant female;
a processor communicatively coupled to the sensor; and
a computer-readable medium having non-transitory, processor-executable instructions stored thereon, wherein execution of the instructions causes the processor to perform a method comprising:
calculating a baseline pre-term birth risk score based on a user input;
acquiring a signal from a sensor over a first window of time;
extracting, from the signal, data corresponding to at least two parameters of interest, wherein the at least two parameters comprise uterine electrical activity of the pregnant female and heart electrical activity of the pregnant female corresponding to signal characteristics including determined changes in uterine electrical activity directionality, determined changes in uterine electrical activity velocity, and determined changes in a heart rate of the pregnant female; and calculating, over a second window of time and based on the extracted data, a statistical measure of each of the at least two parameters of interest, wherein said calculating includes:

comparing the signal characteristics of the extracted data to a plurality of predefined patterns to determine a likelihood that a portion of the extracted data exhibits signal activity that substantially matches at least one of the plurality of predefined patterns, wherein the plurality of predefined patterns comprise preterm labor contractions, term labor contractions, Braxton-Hicks contractions, and a lack of contractions;

determining a probabilistic degree of certainty in which the portion of the extracted data matches at least one of the plurality of predefined patterns; and determining, based on the probabilistic degree of certainty of the match, a probability that the portion of the extracted data includes signal activity indicating progression to an early labor phase, an active labor phase, or a transition labor phase; and determining an instant pre-term birth risk score based, at least in part, on the calculated statistical measures and the user input.

2. The system of claim 1, further comprising a computing device communicatively coupled to the processor, wherein the method performed by the processor further comprises:

receiving the user input with the computing device, wherein the user input comprises two or more of: a user height, a user weight, a user background information, previous pregnancy information, and user risk factor data.

3. The system of claim 2, wherein the user input further comprises user lifestyle data, the user lifestyle data including one or more of: an exercise schedule of the pregnant female, a medical drug regimen of the pregnant female, an alcohol consumption metric of the pregnant female, a smoking habit of the pregnant female, a recreational drug use habit of the pregnant female, a coitus schedule of the pregnant female, an eating habit of the pregnant female, and a frequency of traveling of the pregnant female.

4. The system of claim 1, wherein the method performed by the processor further comprises:

providing a recommendation to the pregnant female to maintain or improve the instant pre-term birth risk score.

5. The system of claim 4, wherein the recommendation comprises one or more of: a change in an activity level, reduce or stop smoking, reduce or stop alcohol consumption, increase an amount of rest, decrease a stress level, drink more water, increase an amount of sleep, increase an amount of healthy foods consumed, reduce or stop drug use, a change in caloric intake, and a change in a medication regimen.

6. The system of claim 1, wherein the method performed by the processor further comprises:

providing one or more of: the baseline pre-term birth risk score and the instant pre-term birth risk score to a healthcare provider; and categorizing a group of pregnant females according to one or more of: their baseline pre-term birth risk score and their instant pre-term birth risk score.

7. The system of claim 6, wherein the method performed by the processor further comprises:

adapting prenatal care based on one or more of: the baseline pre-term birth risk score and the instant pre-term birth risk score.

8. The system of claim 1, wherein the method performed by the processor further comprises:

receiving a biological data input, wherein the biological data input comprises one or more of: a biological test result, a blood test result, an ultrasound screening result, a vaccination record, proteomics data, genetic data, serum test results, and an amniocentesis result; and calculating the instant pre-term birth risk score based, at least in part, on the biological data input.

9. The system of claim 1, wherein the parameters of interest further comprise two or more of:

a contraction wave amplitude, a contraction wave frequency over time, a directionality of a contraction wave, a velocity of contraction wave propagation, a contraction wave duration over time, a resting heart rate, a resting heart rate variability, a blood pressure level, a blood glucose level, an oxygen saturation level, a weight, a heartbeat of a fetus, a heart rate of a fetus, a heart rate variability of a fetus, a position of a fetus, and a weight of a fetus.

10. The system of claim 1, wherein the method performed by the processor further comprises:

comparing the at least two parameters of interest to one or more references, wherein the one or more references identify individual characteristics of a population associated with pre-term birth, and wherein the one or more references include one or more of: a database, a publication, a presentation, and a website;

calculating a probability that the at least two parameters of interest of the pregnant female are associated with pre-term birth based on the one or more references; and calculating the instant pre-term birth risk score based, at least in part, on the calculated probability.

11. The system of claim 1, wherein the method performed by the processor further comprises:

comparing the at least two parameters of interest to an individual baseline for each of the parameters of interest; and calculating the instant pre-term birth risk score based, at least in part, on a deviation between at least one of the at least two parameters of interest and the individual baseline for the respective at least one parameter of interest.

12. The system of claim 1, wherein the method performed by the processor further comprises:

displaying to the pregnant female a series of factors specific to the pregnant female that influence one or more of: the baseline pre-term birth risk score and the instant pre-term birth risk score.

13. The system of claim 1, wherein the method performed by the processor further comprises:

determining a behavioral parameter based on one or more of the parameters of interest associated with a respective parameter of interest, wherein the behavioral parameter comprises one or more of: a stress level of the pregnant female, an energy state of the pregnant female, a sleep quality of the pregnant female, an activity level of the pregnant female, a calorie expenditure of the pregnant female, a cardiorespiratory fitness level of the pregnant female, an activity level of a fetus, and a wellbeing of a fetus; and calculating the instant pre-term birth risk score based, at least in part, on the behavioral parameter.

14. The system of claim 1, further comprising a patch, belt, or clothing accessory coupled to the sensor and configured to position the sensor against a skin surface of the belly region of the pregnant female.

15. The system of claim 1, wherein calculating the instant pre-term birth risk score performed by the processor further comprises using a machine learning model and performing feature selection during training of the machine learning model.

16. The system of claim 15, wherein the method performed by the processor further comprises:
feeding into the machine learning model the at least two parameters of interest and a user input gestational age; and
calculating an accuracy of the machine learning model for predicting the instant pre-term birth risk, starting from a lower bound on accuracy provided by using only the user input gestational age as a predictor.

17. The system of claim 1, wherein the method performed by the processor further comprises:
estimating artifacts over each window of the plurality of windows of time to distinguish artifacts from non-artifacts; and
selecting one or more windows of the plurality of windows of time for extracting the at least two parameters of interest when a percentage of artifact free signal surpasses a threshold.

18. The system of claim 1, wherein calculating the statistical measure further comprises correlating the at least two parameters of interest, the correlating including:
detecting, in the portion of the extracted data and for each parameter of interest, a change in signal amplitude;
determining whether the change in signal amplitude for a first of the at least two parameters of interest and the change in signal amplitude for a second of the at least two parameters of interest occur in an overlapping time period within the second window of time; and
modifying the instant pre-term birth risk score based on the determination.

19. A non-invasive system for assessing over time a pre-term birth risk of a pregnant female, the system comprising:
a sensor configured to be worn on a belly region of the pregnant female;
a processor communicatively coupled to the sensor; and
a computer-readable medium having non-transitory, processor-executable instructions stored thereon, wherein execution of the instructions causes the processor to perform a method comprising:
calculating a baseline pre-term birth risk score based on a user input;
acquiring a signal from a sensor over a first window of time;
extracting, from the signal, data corresponding to at least one parameter of interest, wherein the at least one parameter of interest comprises uterine electrical activity of the pregnant female corresponding to signal characteristics including determined time intervals between uterine electrical activities, determined changes in uterine electrical activity amplitude, and determined changes in uterine electrical activity duration; and
calculating, over a second window of time and based on the extracted data, a statistical measure of the at least one parameter of interest, wherein said calculating includes:
comparing the signal characteristics of the extracted data to a plurality of predefined patterns to determine a likelihood that a portion of the extracted data exhibits signal activity that substantially matches at least one of the plurality of predefined patterns, wherein the plurality of predefined patterns comprise preterm labor contractions, term labor contractions, Braxton-Hicks contractions, and a lack of contractions;
determining a probabilistic degree of certainty in which the portion of the extracted data matches at least one of the plurality of predefined patterns; and
determining, based on the probabilistic degree of certainty of the match, a probability that the portion of the extracted data includes signal activity indicating progression to an early labor phase, an active labor phase, or a transition labor phase; and
determining an instant pre-term birth risk score based, at least in part, on the calculated statistical measures and the user input.

20. The system of claim 19, wherein the method performed by the processor further comprises:
determining a behavioral parameter based on the at least one parameter of interest, wherein the behavioral parameter comprises one or more of: a stress level of the pregnant female, an energy state of the pregnant female, a sleep quality of the pregnant female, an activity level of the pregnant female, a calorie expenditure of the pregnant female, a cardiorespiratory fitness level of the pregnant female, an activity level of a fetus, and a wellbeing of a fetus; and
calculating the instant pre-term birth risk score based, at least in part, on the behavioral parameter.

21. The system of claim 19, wherein the method performed by the processor further comprises:
comparing the at least one parameter of interest to an individual baseline; and
calculating the instant pre-term birth risk score based, at least in part, on a deviation between the at least one parameter of interest and the individual baseline.

* * * * *